United States Patent [19]
Peterson, Jr. et al.

[11] Patent Number: 5,948,780
[45] Date of Patent: Sep. 7, 1999

[54] METHOD FOR TREATING AND PREVENTING HEART FAILURE AND VENTRICULAR DILATATION

[75] Inventors: Joseph Thomas Peterson, Jr., Brighton; Milton Lethan Pressler, Saline, both of Mich.

[73] Assignee: Warner-Lambert Company, Morris Plains, N.J.

[21] Appl. No.: 08/987,167

[22] Filed: Dec. 8, 1997

Related U.S. Application Data

[60] Provisional application No. 60/032,631, Dec. 9, 1996.
[51] Int. Cl.$^6$ ...................... A61K 31/495; A61K 31/445; A61K 31/195; A61K 31/35
[52] U.S. Cl. .......................... 514/255; 514/317; 514/562; 514/561; 514/454
[58] Field of Search ..................................... 514/255, 317, 514/562, 561, 454

[56] References Cited

PUBLICATIONS

Stetler–Stevenson, "Dynamics of Matrix . . . " AJP, May 1996, vol. 148, No. 5, pp. 1345–1350.
Caulfield et al., "Myocardial Conn . . . " Tox Path., vol. 18, No. 4 (Part 1), 1990, pp. 488–496.
Boluyt et al., "Alterations in Cardiac Gene . . . ", Circul. Res., vol. 75, No. 1, Jul. 1994, pp. 23–32.
Klappacher et al., "Measuring Extracellular . . . ", Amer. J. Cardiology, vol. 75, May 1995, pp. 913–918.
Reddy et al., "Activated Myocard . . . ", Clin. Res., vol. 41, No. 3, 1993, p. 660A.
Reddy et al., "Myocardial Coll . . . ", Clin. Res., vol. 41, No. 3, 1993, p. 681.
Spinale, et al., "Diff. Effects . . . ", Abstracts from 67th Scien. Sess., 1994, p. 0590.
Webb, et al., "Time Dep. Chgs . . . ", Circ. vol. 92, No. 8, 1995, p. 3433.
Weber et al., "Inadequate Coll. Tethers . . . " Amer. Heart J., vol. 116, No. 6, Part 1, pp. 1641–1646.
Tyagi et al., "Role of Extracellular . . . " Dept. Int. Med., 1995, pp. 73–80.
Armstrong et al., "Struc. Remodel . . . ", Can J Cardiol, vol. 10, No. 2, 1994, pp. 214–220.
Janicki et al., "Myocard. Coll. Remod . . . ", Brazil J Med Biol Res., vol. 25, No. 10, 1992, pp. 975–982.

*Primary Examiner*—Raymond Henley, III
*Attorney, Agent, or Firm*—Charles W. Ashbrook

[57] ABSTRACT

Matrix metalloproteinase inhibitors are useful for preventing and treating heart failure, and ventricular dilatation in mammals.

21 Claims, No Drawings

METHOD FOR TREATING AND PREVENTING HEART FAILURE AND VENTRICULAR DILATATION

This application claims benefits under 35 USC 119(e) over provisional application No. 60/032,631 filed Dec. 9, 1996.

FIELD OF THE INVENTION

This invention concerns a method for treating and preventing heart failure and ventricular dilatation by administering a chemical compound which inhibits one or more matrix metalloproteinase enzymes.

BACKGROUND OF THE INVENTION

Congestive heart failure (CHF) is a significant health care problem which currently accounts for 7% of total health care expenditures in the USA. Approximately 400,000 new cases of heart failure are identified annually. The primary cause for development of heart failure is ischemic heart disease, and most new cases occur after myocardial infarction. The number of hospital discharges for heart failure has increased from 377,000 in 1979 to 875,000 in 1993, and the number of deaths during the same period has risen 82.5%. The average mortality rate 8 years following initial diagnosis is 85% for men and 65% for women.

The development of CHF begins as an injurious process to the myocardium that reduces cardiac function (especially contractile or pump function) either in a specific region(s) or throughout its entire extent (i.e., globally). Heart failure is said to exist whenever the myocardial injury is of sufficient severity to reduce the heart's capacity to pump an adequate output of blood to satisfy the body's tissue requirements either at rest or during exercise. The disease state of heart failure is not a static situation, but instead progressively worsens until death occurs either suddenly (e.g., by cardiac arrhythmia or embolism to the brain or lung) or gradually from pump failure per se. The progressive decline in heart function in patients with CHF is characterized by progressive enlargement of the ventricular chambers (i.e., ventricular dilatation) and thinning and fibrosis of the ventricular muscle. The progressive ventricular enlargement and accompanying histologic changes in the ventricular muscle are termed "remodeling", a process that involves changes in myocardiocyte structure as well as changes in the amount and composition of the surrounding interstitial connective tissue. An important constituent of the interstitial connective tissue is a matrix of fibrillar collagen, the "tissue scaffolding" that contributes to the maintenance of proper ventricular geometry and structural alignment of adjoining cardiomyocytes. The interstitial collagen matrix is subject to increased dissolution and repair during "remodeling" that leads to ventricular enlargement and progressive heart failure. The deterioration of the collagen matrix is effected by increased activity of matrix metalloproteases, the inhibition of which is a new treatment for heart failure and ventricular dilatation. Ventricular dilatation, the severity of which is measured by the end-diastolic and end-systolic volumes, is a prognostic marker of the probability of subsequent morbidity and mortality. The larger the ventricular chamber dimensions, the greater the likelihood of subsequent morbid events. Not only is pump function impaired by remodeling and ventricular dilation, but the enlarged chambers are prone to formation of clots, which can lead to stroke or embolism to other major organs (e.g., kidney, legs, intestinal tract).

Standard treatment for heart failure utilizes diuretics to decrease fluid retention, angiotensin converting enzyme inhibitors (ACE-Is) to reduce cardiac workload on the failing heart via vasodilation, and in the final stages of failure the positive inotrope digitalis to maintain cardiac output. Although ACE-Is have the benefit of increasing longevity unlike diuretics or positive inotropes, the beneficial effect of ACE-Is is limited to delaying death by only about 18 months. Clinical trials with $\beta$-adrenergic blockers were recently conducted based on the hypothesis that reducing sympathetic drive would decrease the metabolic load on heart muscle cells. Unfortunately, this class of compounds was also found to not have a substantial effect on the progression of heart failure. The failure or limited success of previous heart failure therapies clearly shows that the controlling mechanism(s) mediating heart failure has not been targeted.

Drug development of the treatment of heart failure since the 1960s has focussed on cardiac muscle cells. The goal has been to reduce the workload on the cells, improve bloodflow to the cells, increase the contraction of the muscle, decrease the metabolic demand on cardiac myocytes, or some combination of these by various means. Focus on cardiac myocytes may have served to focus attention too far downstream. Overt heart failure may be caused by the breakdown of cardiac connective tissue. The breakdown in cardiac connective tissue proteins thus mediates cardiac dilation, one of the earliest characteristics of heart failure.

We have now discovered that compounds which inhibit the enzymes that mediate the breakdown of connective tissues are useful for treating heart failure and associated ventricular dilatation. Such enzymes are known as native matrix metalloproteinases, which are classes of naturally occurring enzymes found in most mammals. They are zinc proteases that hydrolyze collagens, proteoglycans, and glycoproteins. The classes include gelatinase A and B, stromelysin-1 and -2, fibroblast collagenase, neutrophil collagenase, matrilysin, metalloelastase, and interstitial collagenase. These enzymes are implicated with a number of diseases which result from breakdown of connective tissues, such as rheumatoid arthritis, osteoarthritis, osteoporosis, multiple sclerosis, and even tumor metastasis. To date, inhibitors of matrix metalloproteinases have not been utilized to treat heart failure or prevent ventricular dilatation. An object of this invention is to provide a method for treating and preventing heart failure and ventricular dilatation by administering a matrix metalloproteinase inhibitor.

SUMMARY OF THE INVENTION

This invention provides a method of treating and preventing heart failure in a mammal comprising administering an effective amount of a matrix metalloproteinase inhibitor. The invention also provides a method for treating and preventing ventricular dilatation comprising administering an effective amount of a matrix metalloproteinase inhibitor.

The methods can be practiced by administering any chemical compound that is effective in inhibiting the biological activity of a matrix metalloproteinase such as collagenase, stromelysin, gelatinase or elastase. Numerous compounds are known to be matrix metallo-proteinase inhibitors, and any of such compounds can be utilized in the method of this invention.

In a preferred embodiment, the matrix metalloproteinase inhibitor to be utilized is a substituted bicyclic compound of the formula

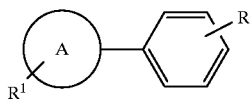

wherein:

A is phenyl or

where Y is CH or N;

$R^1$ is a substituent such as alkyl, aryl, halo, amino, substituted and disubstituted amino, and alkoxy;

$R^2$ is carboxyalkyl ketone or oxime, or a carboxyalkyl sulfonamide such as

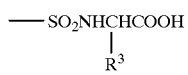

where $R^3$ is alkyl, substituted alkyl, amino, substituted and disubstituted amino, and aryl. Preferred alkyl and alkoxy groups are $C_1$–$C_{10}$ alkyl and $C_1$–$C_{10}$ alkoxy, which can be straight chain or branched, and optionally substituted by halo, amino, nitro, carboxy, hydroxy, aryl, and heteroaryl.

A particularly preferred embodiment is a method of treating and preventing heart failure and ventricular dilatation by administering a biphenylsulfonamide (compounds of the above formula when A is phenyl) such as

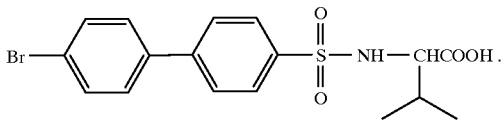

In another embodiment, CHF and ventricular dilatation is treated or prevented by administering a matrix metalloproteinase which is a substituted fused tricyclic compound of the formula

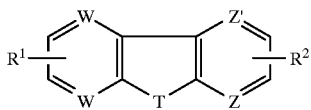

where $R^1$ and $R^2$ are as defined above, T is O, $CH_2$, $SQ(O)_{0,1\ or\ 2}$, C=O, $NR^3$, or

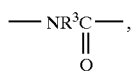

and W, $W^1$, Z, and $Z^1$ are each the same or different and each is $CR^3$, where $R^3$ is alkyl, halo, alkoxy, acyl, and aryl. A preferred method utilizes dibenzofurans and fluorenes of the above formula, for instance compounds such as

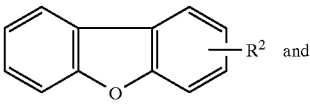

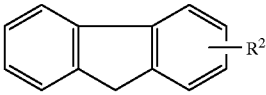

where $R^2$ is, for instance,

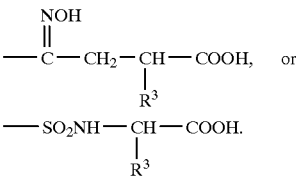

All of the matrix metalloproteinase inhibitors to be utilized in the method of this invention are either known or are readily available by common synthetic processes.

DETAILED DESCRIPTION OF THE INVENTION

All that is required to practice this invention is to administer to a mammal suffering from heart failure or at risk of developing heart failure (e.g., post myocardial infarction) an effective amount of a matrix metalloproteinase inhibitor.

A "matrix metalloproteinase inhibitor" as used herein is any chemical compound that inhibits by at least five percent the hydrolytic activity of at least one matrix metalloproteinase enzyme that is naturally occurring in a mammal. Such compounds are also referred to as "MMP inhibitors". Numerous matrix metalloproteinase inhibitors are known, and all are useful in the method of this invention. For example, 4-biarylbutyric and 5-biarylpentanoic acid derivatives are described in WO 96/15096, which is incorporated herein by reference. The compounds are defined generally as $(T)_x$A-B-D-E-G. Over 400 specific compounds are named, and each is incorporated herein and can be employed in this invention. Especially preferred compounds to be utilized include the following:

[1,1'-Biphenyl]-4-butanoic acid, 4'-chloro-α-(2-methylpropyl)-γ-oxo-;

[1,1'-Biphenyl]-4-butanoic acid, 4'-chloro-α-(2-methylpropyl)-γ-oxo-, (S)-;

[1,1'-Biphenyl]-4-butanoic acid, 4'-chloro-α-(2-methylpropyl)-γ-oxo-, (R)-;

[1,1'-Biphenyl]-4-butanoic acid, 4'-chloro-β-(2-methylpropyl)-γ-oxo-, (S);

[1,1'-Biphenyl]-4-butanoic acid, 4'-chloro-β-(2-methylpropyl)-γ-oxo-, (R)-;

[1,1'-Biphenyl]-4-butanoic acid, 4'-chloro-γ-oxo-;

[1,1'-Biphenyl]-4-butanoic acid, 4'-bromo-γ-oxo-;

[1,1'-Biphenyl]-4-butanoic acid, 4'-fluoro-γ-oxo-;

[1,1'-Biphenyl]-4-butanoic acid, 2'-fluoro-γ-oxo-;

[1,1'-Biphenyl]-4-butanoic acid, 2'-chloro-γ-oxo-;

[1,1'-Biphenyl]-4-butanoic acid, 2',4'-difluoro-γ-oxo-;

[1,1'-Biphenyl]-4-butanoic acid, 3'-chloro-γ-oxo-;

[1,1'-Biphenyl]-4-butanoic acid, α-(2-methylpropyl)-γ-oxo-;

[1,1'-Biphenyl]-4-butanoic acid, 4'-bromo-α-(2-methylpropyl)-γ-oxo-;

[1,1'-Biphenyl]-4-butanoic acid, 4'-fluoro-α-(2-methylpropyl)-γ-oxo-;

[1,1'-Biphenyl]-4-butanoic acid, 4'-ethyl-α-(2-methylpropyl)-γ-oxo-;

[1,1'-Biphenyl]-4-butanoic acid, 2'-fluoro-α-(2-methylpropyl)-γ-oxo-;

[1,1'-Biphenyl]-4-butanoic acid, 2'-chloro-α-(2-methylpropyl)-γ-oxo-;

[1,1'-Biphenyl]-4-butanoic acid, 4'-methoxy-α-(2-methylpropyl)-γ-oxo-;

[1,1'-Biphenyl]-4-butanoic acid, 2',4'-difluoro-α-(2-methylpropyl)-γ-oxo-;

[1,1'-Biphenyl]-4-butanoic acid, 4'-methyl-α-(2-methylpropyl)-γ-oxo-;

[1,1'-Biphenyl]-4-butanoic acid, α-(2-methylpropyl)-γ-oxo-4'-pentyl-;

[1,1'-Biphenyl]-4-butanoic acid, 4'-chloro-α-methylene-γ-oxo-;

[1,1'-Biphenyl]-4-butanoic acid, 2'-chloro-α-methylene-γ-oxo-;

[1,1'-Biphenyl]-4-butanoic acid, 4'-chloro-α-methyl-γ-oxo-;

[1,1'-Biphenyl]-4-butanoic acid, 4'-chloro-γ-oxo-α-pentyl-;

Benzenebutanoic acid, 4-chloro-α-(2-methylpropyl)-γ-oxo-;

Benzenebutanoic acid, 4-methyl-α-methylene-γ-oxo-;

2-Butenoic acid, 4-(4'-chloro[1,1'-biphenyl]-4-yl)-4-oxo-, (E)-;

2-Butenoic acid, 4-[4-(4-chlorophenyoxy)-phenyl]-4-oxo, (E)-;

[1,1'-Biphenyl]-4-butanoic acid, 4'-hydroxy-α-(2-methylpropyl)-γ-oxo-;

[1,1'-Biphenyl]-4-butanoic acid, 4'-chloro-β-methylene-γ-oxo-;

[1,1'-Biphenyl]-4-butanoic acid, 4'-chloro-γ-hydroxy-α-(2-methylpropyl)-;

[1,1'-Biphenyl]-4-butanoic acid, 4'-chloro-γ-hydroxy-α-(2-methylpropyl)-;

2(3H)-Furanone, 5-(4'-chloro[1,1'-biphenyl]-4-yl) dihydro-3-(2-methylpropyl)-;

2(3H)-Furanone, 5-(4'-chloro[1,1'-biphenyl]-4-yl) dihydro-3-(2-methylpropyl)-;

[1,1'-Biphenyl]-4-butanoic acid, 3',4'-dichloro-γ-oxo-α-(3-phenylpropyl)-;

[1,1'-Biphenyl]-4-butanoic acid, 3',5'-dichloro-γ-oxo-α-(3-phenylpropyl)-;

[1,1'-Biphenyl]-4-butanoic acid, 4'-(acetyloxy)-γ-oxo-α-(3-phenylpropyl)-;

Benzenepentanoic acid, α-[2-[4-(5-chloro-2-thienyl) phenyl]-2-oxoethyl]-;

2-Furancarboxylic acid, 5-[4-(3-carboxy-1-oxo-6-phenylhexyl)phenyl]-;

Benzenepentanoic acid, α-[2-oxo-2-[4-(3-pyridinyl) phenyl]ethyl]-;

Benzenepentanoic acid, α-[2-oxo-2-[4-[6-(pentyloxy)-3-pyridinyl]phenyl]ethyl]-;

[1,1'-Biphenyl]-4-butanoic acid, γ-oxo-4'-(pentylthio)-α-(3-phenylpropyl)-;

[1,1'-Biphenyl]-4-butanoic acid, 4'-methoxy-γ-oxo-α-(3-phenylpropyl)-;

[1,1'-Biphenyl]-4-butanoic acid, 3'-chloro-4'-fluoro-γ-oxo-α-(3-phenylpropyl)-;

[1,1'-Biphenyl]-4-butanoic acid, 4'-ethoxy-γ-oxo-α-(3-phenylpropyl)-;

Benzenepentanoic acid, α-[2-oxo-2-[4-(3-thienyl)phenyl] ethyl]-;

[1,1'-Biphenyl]-4-butanoic acid, 2',4'-dichloro-γ-oxo-α-(3-phenylpropyl)-;

[1,1'-Biphenyl]-4-butanoic acid, 4'-formyl-γ-oxo-α-(3-phenylpropyl)-;

[1,1'-Biphenyl]-4-butanoic acid, γ-oxo-α-(3-phenylpropyl)-3',5'-bis(trifluoromethyl)-;

Benzenepentanoic acid, α-[2-oxo-2-[4-(2-thienyl)phenyl] ethyl]-;

[1,1'-Biphenyl]-4-butanoic acid, γ-oxo-α-(3-phenylpropyl)-3'-(trifluoromethyl)-;

[1,1'-Biphenyl]-4-butanoic acid, 2'-formyl-γ-oxo-α-(3-phenylpropyl)-;

[1,1'-Biphenyl]-4-butanoic acid, 4-hydroxy-γ-oxo-α-(3-phenylpropyl)-;

[1,1'-Biphenyl]-4-butanoic acid, γ-oxo-α-(3-phenylpropyl)-4'-propoxy-;

[1,1'-Biphenyl]-4-butanoic acid, γ-oxo-4'-(pentyloxy)-α-(3-phenylpropyl)-;

[1,1'-Biphenyl]-4-butanoic acid, γ-oxo-4'-(pentyloxy)-α-(3-phenylpropyl)-, (S)-;

[1,1'-Biphenyl]-4-butanoic acid, γ-oxo-4'-(pentyloxy)-α-(3-phenylpropyl)-, (R)-;

[1,1'-Biphenyl]-4-butanoic acid, 4'-(hexyloxy)-γ-oxo-α-(3-phenylpropyl)-;

[1,1'-Biphenyl]-4-butanoic acid, 4'-butoxy-γ-oxo-α-(3-phenylpropyl)-;

[1,1'-Biphenyl]-4-butanoic acid, γ-oxo-4'-(3-phenylpropoxy)-α-(3-phenylpropyl)-;

[1,1'-Biphenyl]-4-butanoic acid, 4'-(1-methylethoxy)-γ-oxo-α-(3-phenylpropyl)-;

[1,1'-Biphenyl]-4-butanoic acid, 4'-(heptyloxy)-γ-oxo-α-(3-phenylpropyl)-;

[1,1'-Biphenyl]-4-butanoic acid, 4'-(cyclohexylmethoxy)-γ-oxo-α-(3-phenylpropyl)-;

[1,1'-Biphenyl]-4-butanoic acid, 4'-(2-methylpropoxy)-γ-oxo-α-(3-phenylpropyl)-;

[1,1'-Biphenyl]-4-butanoic acid, γ-oxo-α-(3-phenylpropyl)-4'-(2-propenyloxy)-;

[1,1'-Biphenyl]-4-butanoic acid, 4'-chloro-α-heptyl-γ-oxo-;

[1,1'-Biphenyl]-4-butanoic acid, 4'-chloro-α-decyl-γ-oxo-;

[1,1'-Biphenyl]-4-butanoic acid, 4'-nitro-γ-oxo-α-(2-phenylethyl)-;

[1,1'-Biphenyl]-4-butanoic acid, 4'-cyano-γ-oxo-α-(2-phenylethyl)-;

[1,1'-Biphenyl]-4-butanoic acid, 4'-chloro-α-[2-(2-iodophenyl)ethyl]-γ-oxo-;

[1,1'-Biphenyl]-4-butanoic acid, 4'-chloro-α-[2-(3-iodophenyl)ethyl]-γ-oxo-;

[1,1'-Biphenyl]-4-butanoic acid, 4'-chloro-α-[2-(4-iodophenyl)ethyl]-γ-oxo-;

[1,1'-Biphenyl]-4-butanoic acid, 4'-chloro-α-[2-(3,5-dimethoxyphenyl)ethyl]-γ-oxo-;

[1,1'-Biphenyl]-4-butanoic acid, 4'-chloro-γ-oxo-α-phenyl-;

[1,1'-Biphenyl]-4-butanoic acid, 4'-chloro-γ-oxo-α-(phenylmethyl)-;

[1,1'-Biphenyl]-4-butanoic acid, 4'-chloro-γ-oxo-α-(2-phenylethyl)-;

[1,1'-Biphenyl]-4-butanoic acid, 4'-chloro-γ-oxo-α-[(trimethylsilyl)methyl]-;

[1,1'-Biphenyl]-4-butanoic acid, 4'-bromo-γ-oxo-α-(3-phenylpropyl)-;

[1,1'-Biphenyl]-4-butanoic acid, -γ-oxo-α-(3-phenylpropyl)-;

[1,1'-Biphenyl]-4-butanoic acid, 4'-amino-γ-oxo-α-(2-phenylethyl)-;

[1,1'-Biphenyl]-4-butanoic acid, γ-oxo-α-(2-phenylethyl)-4'-[[(phenylmethoxy)carbonyl]amino]-;

[1,1'-Biphenyl]-4-butanoic acid, 4'-[[(1,1-dimethylethoxy)carbonyl]amino]-γ-oxo-α-(2-phenylethyl)-;

[1,1'-Biphenyl]-4-butanoic acid, 4'-(acetylamino) γ-oxo-α-(2-phenylethyl)-;

[1,1'-Biphenyl]-4-butanoic acid, γ-oxo-4'-[(1-oxopentyl)amino]-α-(2-phenylethyl)-;

[1,1'-Biphenyl]-4-butanoic acid, 4'-[(3,3-dimethyl-1-oxobutyl)amino]-γ-oxo-α-(2-phenylethyl)-;

[1,1'-Biphenyl]-4-butanoic acid, 4'-chloro-α-[2-[2-(methoxycarbonyl)phenyl]ethyl]-γ-oxo-;

[1,1'-Biphenyl]-4-butanoic acid, α-[2-(2-carboxyphenyl)ethyl]-4'-chloro-γ-oxo-;

[1,1'-Biphenyl]-4-butanoic acid, 4'-chloro-α-[2-[2-[(diethylamino)carbonyl]phenyl]ethyl]-γ-oxo-;

[1,1'-Biphenyl]-4-butanoic acid, 4'-chloro-α-[2-[3-[(diethylamino)carbonyl]phenyl]ethyl]-γ-oxo-, (S)-;

[1,1'-Biphenyl]-4-butanoic acid, 4'-chloro-α-[2-[3-[(diethylamino)carbonyl]phenyl]ethyl]-γ-oxo-, (R)-;

Cyclopentanecarboxylic acid, 2-[(4'-chloro[1,1'-biphenyl]-4-yl)carbonyl]-5-[(phenylmethoxy)methyl]-, (1α,2β,5β)-;

Cyclopentanecarboxylic acid, 2-[(4'-chloro[1,1'-biphenyl]-4-yl)carbonyl]-5-(phenoxymethyl)-, (1α,2β,5β)-;

Cyclopentanecarboxylic acid, 2-[(benzoyloxy)-methyl]-5-[(4'-chloro[1,1'-biphenyl]-4-yl)carbonyl]-, (1α,2β,5β)-;

1,2-Benzenedicarboxylic acid, 1-[[2-carboxy-3-[(4'-chloro[1,1'-biphenyl]-4-yl)carbonyl]cyclopentyl]-methyl]-2-methyl ester, (1α,2β,3α)-;

Cyclopentanecarboxylic acid, 2-[(4'-chloro[1,1'-biphenyl]-4-yl)carbonyl]-5-[(2-thienylthio)methyl]-, (1α,2β,5β)-;

Cyclopentanecarboxylic acid, 2-[(benzoylamino)-methyl]-5-[(4'-chloro[1,1'-biphenyl]-4-yl)carbonyl]-, (1α,2β,5β)-;

Cyclopentanecarboxylic acid, 2-[(4'-chloro[1,1'-biphenyl]-4-yl)carbonyl]-5-[[(2-methoxyethoxy)methoxy]methyl]-, (1α,2β,5β)-;

Cyclopentanecarboxylic acid, 2-[(4'-chloro[1,1'-biphenyl]-4-yl)carbonyl]-5-[[(phenylmethyl)thio]-methyl]-, (1α,2β,5β)-;

Cyclopentanecarboxylic acid, 2-[(4'-chloro[1,1'-biphenyl]-4-yl)carbonyl]-5-[(phenylthio)methyl]-, (1α,2β,5β)-;

Cyclopentanecarboxylic acid, 2-[(4'-chloro[1,1'-biphenyl]-4-yl)carbonyl]-5-[(propylthio)methyl]-, (1α,2β,5β)-;

Cyclopentanecarboxylic acid, 2-[(2-benzothiazolylthio)methyl]-5-[(4'-chloro[1,1'-biphenyl]-4-yl)carbonyl]-, (1α,2β,5β)-;

Benzoic acid, 2-[[[2-carboxy-3-[(4'-chloro[1,1'-biphenyl]-4-yl)carbonyl]cyclopentyl]methyl]thio]-, 1-methyl ester, (1α,2β,3α)-;

Cyclopentanecarboxylic acid, 2-[(4'-chloro[1,1'-biphenyl]-4-yl)carbonyl]-5-[[[(phenylmethoxy)carbonyl]amino]methyl]-, (1α,2β5β)-;

Benzoic acid, 2-methyl-, [2-carboxy-3-[(4'-chloro[1,1'-biphenyl]-4-yl)carbonyl]cyclopentyl]methyl ester, (1α,2β,3α)-;

Benzoic acid, 3-methyl-, [2-carboxy-3-[(4'-chloro[1,1'-biphenyl]-4-yl)carbonyl]cyclopentyl]methyl ester, (1α,2β,3α)-;

Benzoic acid, 4-methyl-, [2-carboxy-3-[(4'-chloro[1,1'-biphenyl]-4-yl)carbonyl]cyclopentyl]methyl ester, (1α,2β,3α)-;

Benzoic acid, 2-methoxy-, [2-carboxy-3-[(4'-chloro[1,1'-biphenyl]-4-yl)carbonyl]cyclopentyl]methyl ester, (1α,2β,3α)-;

Benzoic acid, 3-methoxy-, [2-carboxy-3-[(4'-chloro[1,1'-biphenyl]-4-yl)carbonyl]cyclopentyl]methyl ester, (1α,2β,3α)-;

Benzoic acid, 4-methoxy-, [2-carboxy-3-[(4'-chloro[1,1'-biphenyl]-4-yl)carbonyl]cyclopentyl]methyl ester, (1α,2β,3α)-;

Cyclopentanecarboxylic acid, 2-[(2-benzoxazolylthio)methyl]-5-[(4'-chloro[1,1'-biphenyl]-4-yl)carbonyl]-, (1α,2β,5β)-;

Cyclopentanecarboxylic acid, 2-[(4'-chloro[1,1'-biphenyl]-4-yl)carbonyl]-5-[(1,3-dihydro-4-nitro-1,3-dioxo-2H-isoindol-2-yl)methyl]-, (1α,2β,5β)-;

Cyclopentanecarboxylic acid, 2-[(4'-chloro[1,1'-biphenyl]-4-yl)carbonyl]-5-[(1,3-dihydro-5-nitro-1,3-dioxo-2H-isoindol-2-yl)methyl]-, (1α,2β,5β)-;

2H-Benz[f]isoindole-2-butanoic acid, α-[2-(4'-ethoxy[1,1'-biphenyl]-4-yl)-2-oxoethyl]-1,3-dihydro-1,3-dioxo-;

[1,1'-Biphenyl]-4-butanoic acid, α-(acetylamino)-4'-chloro-γ-oxo-;

2H-Isoindole-2-hexanoic acid, α-[2-(4'-chloro[1,1'-biphenyl]-4-yl)-2-oxoethyl]-1,3-dihydro-1,3-dioxo-;

[1,1'-Biphenyl]-4-butanoic acid, 4'-chloro-α-[[[3-(methoxycarbonyl)phenyl]thio]methyl]-γ-oxo-;

[1,1'-Biphenyl]-4-butanoic acid, 4'-chloro-α-[[(2,6-dimethylphenyl)thio]methyl]-γ-oxo-;

[1,1'-Biphenyl]-4-butanoic acid, 4'-chloro-α-[[[4-fluoro-2-(methoxycarbonyl)phenyl]thio]methyl]-γ-oxo-;

[1,1'-Biphenyl]-4-butanoic acid, 4'-chloro-α-[[[3-[(diethylamino)carbonyl]phenyl]thio]methyl]-γ-oxo-;

[1,1'-Biphenyl]-4-butanoic acid, 4'-chloro-α-[[[2-[(dimethylamino)carbonyl]phenyl]thio]methyl]-γ-oxo-;

[1,1'-Biphenyl]-4-butanoic acid, 4'-chloro-α-[[[3-[(dimethylamino)carbonyl]phenyl]thio]methyl-]γ-oxo-;

Bicyclo[2.2.1]hept-5-ene-2-carboxylic acid, 3-[[4'-(pentyloxy)[1,1'-biphenyl]-4-yl]carbonyl]-, (2-endo, 3-exo)-;

1-Cyclopentene-1-carboxylic acid, 5-[(4'-chloro[1,1'-biphenyl]-4-yl)carbonyl]-;

Cyclopentanecarboxylic acid, 2-[(4'-chloro[1,1'-biphenyl]-4-yl)carbonyl]-5-[(phenylmethyl)thio]-, (1α,2β,5α)-;

Cyclopentanecarboxylic acid, 2-[(4'-chloro[1,1'-biphenyl-4-yl)carbonyl]-5-[(phenylmethyl)thio]-, (1α,2β,5β)-;

1-Cyclopentene-1-carboxylic acid, 5-[[4'-(pentyloxy)[1,1'-biphenyl]-4-yl]carbonyl]-;

1-Cyclopentene-1-carboxylic acid, 5-[[4'-(hexyloxy)[1,1'-biphenyl]-4-yl)]carbonyl]-;

[1,1'-Biphenyl]-4-butanoic acid, 4'-hydroxy-γ-oxo-α-[(phenylthio)methyl]-;

[1,1'-Biphenyl]-4-butanoic acid, α-[2-[2-[(butylamino)carbonyl]phenyl]ethyl]-4'-chloro-γ-oxo-;

[1,1'-Biphenyl]-4-butanoic acid, α-[2-(3-carboxyphenyl)ethyl]-4'-chloro-γ-oxo-;

[1,1'-Biphenyl]-4-butanoic acid, 4'-chloro-α-[2-[3-[(diethylamino)carbonyl]phenyl]ethyl]-γ-oxo-;

[1,1'-Biphenyl]-4-butanoic acid, α-[2-[3-[(butylamino)carbonyl]phenyl]ethyl]-4'-chloro-γ-oxo-;

[1,1'-Biphenyl]-4-butanoic acid, 4'-chloro-α-[2-[4-[(diethylamino)carbonyl]phenyl]ethyl]-γ-oxo-;

[1,1'-Biphenyl]-4-butanoic acid, α-[2-[4-[(butylamino)carbonyl]phenyl]ethyl]-4'-chloro-γ-oxo-;

[1,1'-Biphenyl]-4-butanoic acid, α-[2-(4-carboxyphenyl)ethyl]-4'-chloro-γ-oxo-;

[1,1'-Biphenyl]-4-butanoic acid, 4'-methoxy-γ-oxo-α-(2-phenylethyl)-;

[1,1'-Biphenyl]-4-butanoic acid, 4'-hydroxy-γ-oxo-α-(2-phenylethyl)-;

[1,1'-Biphenyl]-4-butanoic acid, 4'-ethoxy-γ-oxo-α-(2-phenylethyl)-;

[1,1'-Biphenyl]-4-butanoic acid, γ-oxo-α-(2-phenylethyl)-4'-propoxy-;

[1,1'-Biphenyl]-4-butanoic acid, γ-oxo-4'-(pentyloxy)-α-(2-phenylethyl)-;

[1,1'-Biphenyl]-4-butanoic acid, 4'-(hexyloxy)-γ-oxo-α-(2-phenylethyl)-;

[1,1'-Biphenyl]-4-butanoic acid, 4'-butoxy-γ-oxo-α-(2-phenylethyl)-;

[1,1'-Biphenyl]-4-butanoic acid, γ-oxo-α-(2-phenylethyl)-4'-(phenylmethoxy)-;

[1,1'-Biphenyl]-4-butanoic acid, α-[2-(3-iodophenyl)ethyl]-γ-oxo-4'-(pentyloxy)-;

[1,1'-Biphenyl]-4-butanoic acid, α-[2-(3-iodophenyl)ethyl]-γ-oxo-4'-(phenylmethoxy)-;

[1,1'-Biphenyl]-4-butanoic acid, α-[2-(3-[(diethylamino)carbonyl]phenyl]ethyl]-γ-oxo-4'-(pentyloxy)-;

[1,1'-Biphenyl]-4-butanoic acid, α-[2-(3-[(diethylamino)carbonyl]phenyl]ethyl]-γ-oxo-4'-(phenylmethoxy)-;

1,2-Pyrrolidinedicarboxylic acid, 3-[(4'-chloro[1,1'-biphenyl]-4-yl)carbonyl]-, 1-(phenylmethyl) ester, (2S-trans)-;

1,2-Pyrrolidinedicarboxylic acid, 3-[(4'-chloro[1,1'-biphenyl]-4-yl)carbonyl]-, 1-(phenylmethyl) ester, (2'R-trans)-;

L-Proline, 3-[(4'-chloro[1,1'-biphenyl]-4-yl)carbonyl]-1-[[(phenylmethyl)amino]carbonyl]-, trans-;

L-Proline, 3-[(4'-chloro[1,1'-biphenyl]-4-yl)carbonyl]-1-(1-oxo-3-phenylpropyl)-, trans-;

L-Proline, 3-[(4'-chloro[1,1'-biphenyl]-4-yl)carbonyl]-1-(phenylacetyl)-, trans-;

L-Proline, 3-[(4'-chloro[1,1'-biphenyl]-4-yl)carbonyl]-1-(3,3-dimethyl-1-oxobutyl)-, trans-;

[1,1'-Biphenyl]-4-butanoic acid, 4'-chloro-α-heptyl-γ-oxo-;

[1,1'-Biphenyl]-4-butanoic acid, 4'-chloro-α-decyl-γ-oxo-;

[1,1'-Biphenyl]-4-butanoic acid, 4'-nitro-γ-oxo-α-(2-phenylethyl)-;

[1,1'-Biphenyl]-4-butanoic acid, 4'-cyano-γ-oxo-α-(2-phenylethyl)-;

[1,1'-Biphenyl]-4-butanoic acid, 4'-chloro-α-[2-(2-iodophenyl)ethyl]-γ-oxo-;

[1,1'-Biphenyl]-4-butanoic acid, 4'-chloro-α-[2-(3-iodophenyl)ethyl]-γ-oxo-;

[1,1'-Biphenyl]-4-butanoic acid, 4'-chloro-α-[2-(4-iodophenyl)ethyl]-γ-oxo-;

[1,1'-Biphenyl]-4-butanoic acid, 4'-chloro-α-[2-(3,5-dimethoxyphenyl)ethyl]-γ-oxo-;

[1,1'-Biphenyl]-4-butanoic acid, 4'-chloro-γ-oxo-α-phenyl-;

[1,1'-Biphenyl]-4-butanoic acid, 4'-chloro-γ-oxo-α-(phenylmethyl)-;

[1,1'-Biphenyl]-4-butanoic acid, 4'-chloro-γ-oxo-α-(2-phenylethyl)-;

[1,1'-Biphenyl]-4-butanoic acid, 4'-chloro-γ-oxo-α-[(trimethylsilyl)methyl]-;

[1,1'-Biphenyl]-4-butanoic acid, 4'-bromo-γ-oxo-α-(3-phenylpropyl)-;

[1,1'-Biphenyl]-4-butanoic acid, γ-oxo-α-(3-phenylpropyl)-;

[1,1'-Biphenyl]-4-butanoic acid, 4'-amino-γ-oxo-α-(2-phenylethyl)-;

[1,1'-Biphenyl]-4-butanoic acid, γ-oxo-α-(2-phenylethyl)-4'-[[(phenylmethoxy)carbonyl]amino]-;

[1,1'-Biphenyl]-4-butanoic acid, 4'-[[(1,1-dimethylethoxy)carbonyl]amino]-γ-oxo-α-(2-phenylethyl)-;

[1,1'-Biphenyl]-4-butanoic acid, 4'-(acetylamino)-γ-oxo-α-(2-phenylethyl)-;

[1,1'-Biphenyl]-4-butanoic acid, γ-oxo-4'-[(1-oxopentyl)amino]-α-(2-phenylethyl)-;

[1,1'-Biphenyl]-4-butanoic acid, 4'-[(3,3-dimethyl-1-oxobutyl)amino]-γ-oxo-α-(2-phenylethyl)-;

[1,1'-Biphenyl]-4-butanoic acid, 4'-chloro-α-[2-[2-methoxycarbonyl)phenyl]ethyl]-γ-oxo-;

[1,1'-Biphenyl]-4-butanoic acid, α-[2-(2-carboxyphenyl)ethyl]-4'-chloro-γ-oxo-;

[1,1'-Biphenyl]-4-butanoic acid, 4'-chloro-α-[2-[2-[(diethylamino)carbonyl)phenyl]ethyl]-γ-oxo-;

[1,1'-Biphenyl]-4-butanoic acid, 4'-chloro-α-[2-[3-[(diethylamino)carbonyl)phenyl]ethyl]-γ-oxo-, (S)-; and

[1,1'-Biphenyl]-4-butanoic acid, 4'-chloro-α-[2-[3-[(diethylamino)carbonyl)phenyl]ethyl]-γ-oxo-, (R)-.

Fenbufen and compounds related to fenbufen can be utilized. Such compounds are described in U.S. Pat. No. 3,784,701 and by Child, et al., *J. Pharm. Sci.*, 1977;66:466–476, and Arzneim-Forsch, 1980;30(4A):695–702, all of which are incorporated herein by reference. Preferred compounds from the fenbufen series to be utilized in this invention have the formula

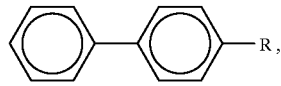

where R is $$\underset{\text{CCH}_2\text{CH}_2\text{COOH (fenbufen)}}{\overset{\text{O}}{\|}},$$

COCH=CHCOOH, SO$_2$NH$_2$,

COCH$_2$CHCOOH, COCH$_2$CH—COOH,
          |
          CH$_3$

—COCH$_2$CH$_2$SO$_3$Na,

CH(OH)CH$_2$CH$_2$COOH,  —COCH$_2$CHCOOH,
                                    |
                                    OH

COCH$_2$CH$_2$CONHOH, C(=NOH)CH$_2$CH$_2$COOH, and
—COCH$_2$SCH$_2$COOH.

Numerous peptides are known matrix metalloproteinase inhibitors. Typical of such peptides are those described in U.S. Pat. Nos. 5,300,501; 5,530,128; 5,455,258; 5,552,419; WO 95/13289; and WO 96/11209, all of which are incorporated herein by reference. Such compounds are illustrated by the formula $$R^7S \underset{R^8}{\overset{O}{\diagdown}} \underset{H}{N} \underset{O}{\overset{R^1}{\diagdown}} \underset{O}{\overset{R^2}{N}} \underset{R^3}{\overset{O}{\diagdown}} NR^4R^5$$

where each of the variable groups can include hydrogen alkyl, aryl, heteroaryl, alkenyl, alkynyl, carboxy, and the like. Preferred compounds from within this class which can be utilized in the method of this invention include the following:

N-[2,3-bis-Acetylmercaptopropanoyl]-L-leucyl-L-phenylalanine N-methylamide;
N-[2-acetylmercapto-3-methoxycarbonylpropanoyl]-L-leucyl-L-phenylalanine N-methylamide;
N-[2-acetylmercapto-4-methoxycarbonylbutanoyl]-L-leucyl-L-phenylalanine N-methylamide;
N-[2-acetylmercapto-5-methoxycarbonylpentanoyl]-L-leucyl-L-phenylalanine N-methylamide;
N-[2-acetylmercapto-6-methoxycarbonylhexanoyl]-L-leucyl-L-phenylalanine N-methylamide;
N-[2-acetylmercapto-4-phthalimidobutanoyl]-L-leucyl-L-phenylalanine N-methylamide;
N-[2-acetylmercapto-5-phthalimidopentanoyl]-L-leucyl-L-phenylalanine N-methylamide;
N-[2-acetylmercapto-6-phthalimidohexanoyl]-L-leucyl-L-phenylalanine N-methylamide;
N-[2,3-bis-mercaptopropanoyl]-L-leucyl-L-phenylalanine N-methylamide;
N-[2-mercapto-3-methoxycarbonylpropanoyl]-L-leucyl-L-phenylalanine N-methylamide;
N-[2-mercapto-4-methoxycarbonylbutanyol]-L-leucyl-L-phenylalanine N-methylamide;
N-[2-mercapto-4-methoxycarbonylpentanoyl]-L-leucyl-L-phenylalanine N-methylamide;
N-[2-mercapto-6-methoxycarbonylhexanoyl]-L-leucyl-L-phenylalanine N-methylamide;
N-[2-mercapto-4-phthalimidobutanoyl]-L-leucyl-phenylalanine N-methylamide;
N-[2-mercapto-5-phthalimidopentanoyl]-L-leucyl-L-phenylalanine N-methylamide;
N-[2-mercapto-6-phthalimidohexanyoyl]-L-leucyl-L-phenylalanine N-methylamide;
N-[2-acetylmercapto-5-methoxycarbonylpentanoyl]-L-leucyl-L-phenylalanine N-methylamide;
N-[2-acetylmercapto-6-methoxycarbonylhexanyol]-L-leucyl-L-phenylalanine N-methylamide;
N-[2-acetylmercapto-6-methoxycarbonylhexanyol]-L-valinyl-L-phenylalanine N-methylamide;
N-[2-acetylmercapto-6-methoxycarbonylhexanyol]-L-leucyl-L-tryptophan N-methylamide;
N-[2-acetylmercapto-5-phthalimidopentanoyl]-L-leucyl-L-phenylalanine N-methylamide;
N-[2-acetylmercapto-5-phthalimidopentanoyl]-L-valinyl-L-phenylalanine N-methylamide;
N-[2-acetylmercapto-5-phthalimidopentanoyl]-L-leucyl-L-tryptophan N-methylamide;
N-[2-acetylmercapto-5-phthalimidopentanoyl]-L-leucyl-L-[β-(4-thiazolyl)]alaine N-methylamide;
N-[2-acetylmercapto-5-phthalimidopentanoyl]-L-leucyl-L-(β-(2-pyridyl)alanine N-methylamide;
N-[2-acetylmercapto-5-phthalimidopentanoyl]-L-leucyl-5-methyl-L-glutamicacid N-methylamide;
N-[2-acetylmercapto-6-phthalimidohexanoyl]-L-leucyl-L-phenylalanine N-methylamide;
N-[2-acetylmercapto-2-(3-phthalimido) phenylacetyl]-L-leucyl-L-phenylalanine N-methylamide;
N-[2-mercapto-5-methoxycarbonylpentanoyl]-L-phenylalanine N-methylamide;
N-[2-mercapto-6-methoxycarbonylhexanyol]-L-leucyl-L-phenylalanine N-methylamide;
N-[2-mercapto-6-methoxycarbonylhexanyol]-L-leucyl-L-tryptophan N-methylamide;
N-[2-mercapto-5-phthalimidopentanoyl]-L-leucyl-L-phenylalanine N-methylamide;
N-[2-mercapto-5-phthalimidopentanoyl]-L-leucyl-L-tryptophan N-methylamide;
N-[2-mercapto-5-phthalimidopentanoyl]-L-leucyl-L-[β-(4-thiazolyl)alanine N-methylamide;
N-[2-mercapto-5-phthalimidopentanoyl]-L-leucyl-L-[β-(2-pyridyl)]alanine N-methylamide;
N-[2-mercapto-5-phthalimidopentanoyl]-L-leucyl-5-methyl-L-glutamic acid N-methylamide;
N-[2-mercapto-6-phthalimidohexanoyl]-L-leucyl-L-phenylalanine N-methylamide;
N-[N-mercaptoacetyl)-L-leucyl]-L-phenylalanine N-methylamide;
N-[acetomercaptoacyl)-L-leucyl-L-phenylalanine methylamide;
(RS)-2-(acetylthio)pentanoyl-L-leucyl-L-phenylalanine N-methylamide;
(RS)-2-(acetylthio)propanoyl-L-leucyl-L-phenylalanine N-methylamide;
(RS)-2-(acetylthio)-3-methylbutanoyl-L-leucyl-L-phenylalanine N-methylamide;
(RS)-2-(acetylthio)-2-phenylacetyl-L-leucyl-L-phenylalanine N-methylamide;
(RS)-2-(acetylthio)-3-phenylpropanoyl-L-leucyl-L-phenylalanine N-methylamide;
(RS)-2-(acetylthio)-4-phenylbutanoyl-L-leucyl-L-phenylalanine N-methylamide;
N-(acetylmercaptoacyl)-L-threonyl-L-phenylalanine methylamide;
N-(acetylmercaptoacyl)-L-leucyl-L-tryptophan methylamide;
(RS)-2-mercaptopentanoyl-L-leucyl-L-phenylalanine N-methylamide;

(RS)-2-mercaptopropanoyl-L-leucyl-L-phenylalanine N-methylamide;
(RS)-2-mercapto-3-methylbutanoyl-L-leucyl-L-phenylalanine N-methylamide;
(RS)-2-mercapto-2-phenylacetyl-L-leucyl-L-phenylalanine N-methylamide;
(RS)-2-mercapto-3-phenylpropanoyl-L-leucyl-L-phenylalanine N-methylamide;
(RS)-2-mercapto-4-phenylbutanoyl-L-leucyl-L-phenylalanine N-methylamide;
N-[N-(mercaptoacetyl)-L-threonyl]-L-phenylalanine methylamide; and
N-[N-(mercaptoacetyl)-L-leucyl]-L-tryptophan methylamide.

Additional matrix metalloproteinase (MMP) inhibitors, which can be utilized to prevent and treat heart failure and ventricular dilatation, include the following:

[4-(N-Hydroxyamino)-2(R)-cyclohexylmethylsuccinyl]-L-β-cyclohexylalanine-N-(2-phenylethyl)amide;
[4-N-(Hydroxyamino)-2R-isobutylsuccinyl]-L-β-cyclohexylalanine-N-(2-phenylethyl)amide;
[4-(N-hydroxyamino)-2R-phenylpropylsuccinyl]-L-β-cyclohexylalanine-N-(2-phenylethyl)amide;
[4-(N-Hydroxyamino)-2R-phenylpropylsuccinyl]-L-β-cyclohexylalanine-N-[2-(N,N-dimethylamino)ethyl]amide;
[4-(N-Hydroxyamino)-2R-phenylpropylsuccinyl]-L-β-cyclohexylalanine-N-[2-(p-sulphonamidophenyl)-ethyl]amide;
[4-(N-Hydroxyamino)-2R-phenylpropylsuccinyl]-L-β-cyclohexylalanine-N-(2-(p-sulphonylphenyl)ethyl)amide;
[4-(N-Hydroxyamino)-2R-phenylpropylsuccinyl]-L-β-cyclohexylalanine-N-[2-(2-pyridyl)ethyl]amide;
[4-(N-Hydroxyamino)-2R-pentylsuccinyl]-L-β-cyclohexylalanine-N-(2-phenylethyl)amide;
[4-(N-Hydroxyamino)-2R-isoamylsuccinyl]-L-β-cyclohexylalanine-N-(2-phenylethyl)amide;
[4-(N-Hydroxyamino)-2R-phenylbutylsuccinyl]-L-β-cyclohexylalanine-N-(2-phenylethyl)amide;
[4-(N-Hydroxyamino)-2R-phenylpropylsuccinyl]-L-β-cyclohexylalanine-N-[3-(4-morpholinyl)propyl]amide;
[4-(N-Hydroxyamino)-2R-phenylpropylsuccinyl]-L-β-cyclohexylalanine-N-[β-alanine]amide;
[4-(N-Hydroxyamino)-2R-isobutylsuccinyl]-L-β-cyclohexylalanine amide;
[4-(N-Hydroxyamino)-2R-(3-phenylpropyl)succinyl]-L-β-cyclohexylalanine amide;
[4-(N-Hydroxyamino)-2R-(3-phenylbutyl)succinyl]-L-β-cyclohexylalanine amide;
[4-N-(Hydroxyamino)-2R-phenylethylsuccinyl]-L-leucine-N-(2-phenylethyl)amide;
[4-(N-Hydroxyamino)-2R-phenylpropylsuccinyl]-L-leucine-N-(2-phenylethyl)amide;
[4-(N-Hydroxyamino)-2(R)-isobutylsuccinyl]-L-tryptophan amide;
[4-(N-Hydroxyamino)-2(R)-isobutylsuccinyl]-L-valine amide;
[3-Phosphono-2R,S-phenylpropyl-1-oxopropyl]-L-β-cyclohexylalanine-N-(2-phenylethyl)amide, dimethylester;
[3-Phosphono-2R-phenylpropyl-1-oxopropyl]-L-β-cyclohexylalanine-N-(2-phenylethyl)amide;
[3-Phosphono-2S-phenylpropyl-1-oxopropyl]-L-β-cyclohexylalanine-β-alanine;
[3-Phosphono-2R-phenylpropyl-1-oxopropyl]-L-β-cyclohexylalanine;
[3-Phosphono-2S-phenylpropyl-1-oxopropyl]-L-β-cyclohexylalanine-β-alanine, methyl ester;
[3-Phosphono-2R,S-phenylpropyl-1-oxopropyl]-L-β-cyclohexylalanine-N-[4(3-aminopropyl)morpholine]amide, bromine salt;
[3-Phosphono-2R,S-(4-methylphenyl)propyl-1-oxopropyl]-L-β-cyclohexylalanine-N-(2-phenylethyl)-amide, diethylester;
[3-Phosphono-2R,S-(4-methylphenyl)propyl-1-oxopropyl]-L-β-cyclohexylalanine-N-(2-phenylethyl)-amide;
4-t-Butoxy-2(R)-[3-(2-phenoxyethyl)succinyl]-L-β-cyclohexylalanine-N-(2-phenylethyl)amide;
4-Hydroxy-2(R)-[3-(2-phenoxyethyl)succinyl]-L-β-cyclohexylalanine-N-(2-phenylethyl)amide;
4-(N-Hydroxyamino-2(R)-[3-(2-phenoxyethyl)-succinyl]-L-β-cyclohexylalanine-N-(2-phenylethyl)amide;
{4-Hydroxy-2(R)-[3-(4-pyridinium)propyl]succinyl}-L-β-cyclohexylalanine-N-(2-phenylethyl)amide;
{4-(N-Hydroxyamino)-2(R)-[3-(4-pyridinium)propyl]-succinyl}-L-β-cyclohexylalanine-N-(2-phenylethyl)amide;
{4-(N-Hydroxyamino)-2(R)-[3-(N-methyl-4-pyridinium)propyl]succinyl}-L-β-cyclohexylalanine-N-(2-phenylethyl)amide;
{4-Hydroxy-2-(R)-[3-(4-methylphenyl)propyl]-succinyl}-L-β-cyclohexylalanine-N-[(2-morpholinesulphonylamino)ethyl]amide;
{4-(N-Hydroxyamino)-2-(R)-[3-(4-methylphenyl)-propyl]succinyl}-L-β-cyclohexylalanine-N-[(2-morpholinesulphonylamino)ethyl]amide;
{4-(N-Hydroxyamino)-2-(R)-[3-(4-chlorophenyl)-propyl]succinyl}-L-β-cyclohexylalanine-N-[(2-morpholinesulphonylamino)ethyl]amide;
{4-N-Hydroxyamino)-2-(R)-[3-(4-methylphenyl)-propyl]succinyl}-L-β-cyclohexylalanine-N-[(2-dimethylsulphonylamino)propyl]amide;
[4-(N-Hydroxyamino)-2(R)-[3-(4-chlorophenyl)-propyl]succinyl]-L-[S-(methyl)penicillamine]-N-methylamide;
[4-(N-Hydroxyamino)-2(R)-[3-(4-chlorophenyl)-propyl]succinyl]-L-[S-(methyl)penicillamine]amide;
[4-(N-Hydroxyamino)-2(R)-[3-(4-chlorophenyl)-propyl]succinyl]-L-penicillamine]amide;
{4-(N-Hydroxyamino)-2(R)-[3-(4-chlorophenyl)-propyl]succinyl}-L-[S-(methyl)penicillaminesulphone]-N-methylamide;
{4-(N-Hydroxyamino)-2(R)-[3-(4-chlorophenyl)-propyl]succinyl}-L-[S-(methyl)penicillaminesulphoxide]-N-methylamide;
{4-(N-Hydroxyamino)-2(R)-[3-(4-chlorophenyl)-propyl]succinyl}-L-penicillamine-N-methylamide;
[4-(N-Hydroxyamino)-2(R)-3-(2-methylpropyl)-succinyl]-L-[S-methyl)penicillamine]-N-methylamide;
$N^4$-Hydroxy-$N^1$-(1-(S)-carbamoyl-2,2-dimethylpropyl)-2-(R)-4-(chlorophenylpropyl)-succinamide;
$N^4$-Hydroxy-$N^1$-(1-(S)-carbamoyl-2,2-dimethylpropyl)-2-(R)-(4-methylphenylpropyl)-succinamide;
$N^4$-Hydroxy-$N^1$-(1-(S)-carbamoyl-2,2-dimethylpropyl)-2-(R)-(4-methoxyphenylpropyl)-succinamide;
$N^4$-Hydroxy-$N^1$-(1-(S)-carbamoyl-2,2-dimethylpropyl)-2-(R)-(4-trifluoromethylphenylpropyl)-succinamide;
$N^4$-Hydroxy-$N^1$-(1-(S)-carbamoyl-2,2-dimethylpropyl)-2-(R)-(4-chloromethylphenylpropyl)-succinamide;
N-[N-(Mercaptoacetyl)-L-leucyl]-L-phenylalanine methylamide;
N-(Acetomercaptoacyl)-L-leucyl-L-phenylalanine methylamide;
(RS)-2-(Acetylthio)pentanoyl-L-leucyl-L-phenylalanine N-methylamide;
(RS)-2-(Acetylthio)propanoyl-L-leucyl-L-phenylalanine N-methylamide;
(RS)-2-(Acetylthio)-3-methylbutanoyl-L-leucyl-L-phenylalanine N-methylamide;

(RS)-2-(Acetylthio)-2-phenylacetyl-L-leucyl-L-phenylalanine N-methylamide;
(RS)-2-(Acetylthio)-3-phenylpropanoyl-L-leucyl-L-phenylalanine N-methylamide;
(RS)-2-(Acetylthio)-4-phenylbutanoyl-L-leucyl-L-phenylalanine N-methylamide;
N-(Acetylmercaptoacyl)-L-threonyl-L-phenylalanine methylamide;
N-(Acetylmercaptoacyl)-L-leucyl-L-tryptophan methylamide;
(RS)-2-Mercaptopentanoyl-L-leucyl-L-phenylalanine N-methylamide;
(RS)-2-Mercaptopropanoyl-L-leucyl-L-phenylalanine N-methylamide;
(RS)-2-Mercapto-3-methylbutanoyl-L-leucyl-L-phenylalanine N-methylamide;
(RS)-2-Mercapto-2-phenylacetyl-L-leucyl-L-phenylalanine N-methylamide;
(RS)-2-Mercapto-3-phenylpropanoyl-L-leucyl-L-phenylalanine N-methylamide;
(RS)-2-Mercapto-4-phenylbutanoyl-L-leucyl-L-phenylalanine N-methylamide;
N-[N-(Mercaptoacetyl)-L-threonyl]-L-phenylalanine methylamide;
N-[N-(Mercaptoacetyl)-L-leucyl]-L-tryptophan methylamide;
N-[2,3-bis-Acetylmercaptopropanoyl]-L-leucyl-L-phenylalanine N-methylamide;
N-[2-Acetylmercapto-3-methoxycarbonylpropanoyl]-L-leucyl-L-phenylalanine N-methylamide;
N-[2-Acetylmercapto-4-methoxycarbonylbutanoyl]-L-leucyl-L-phenylalanine N-methylamide;
N-[2-Acetylmercapto-5-methoxycarbonylpentanoyl]-L-leucyl-L-phenylalanine N-methylamide;
N-[2-Acetylmercapto-6-methoxycarbonylhexanoyl]-L-leucyl-L-phenylalanine N-methylamide;
N-[2-Acetylmercapto-4-phthalimidobutanoyl]-L-leucyl-L-phenylalanine N-methylamide;
N-[2-Acetylmercapto-5-phthalimidopentanoyl]-L-leucyl-L-phenylalanine N-methylamide;
N-[2-Acetylmercapto-6-phthalimidohexanoyl]-L-leucyl-L-phenylalanine N-methylamide;
N-[2,3-bis-Mercaptopropanoyl]-L-leucyl-L-phenylalanine N-methylamide;
N-[2-Mercapto-3-methoxycarbonylpropanoyl]-L-leucyl-L-phenylalanine N-methylamide;
N-[2-Mercapto-4-methoxycarbonylbutanoyl]-L-leucyl-L-phenylalanine N-methylamide;
N-[2-Mercapto-5-methoxycarbonylpentanoyl]-L-leucyl-L-phenylalanine N-methylamide;
N-[2-Mercapto-6-methoxycarbonylhexanoyl]-L-leucyl-L-phenylalanine N-methylamide;
N-[2-Mercapto-4-phthalimidobutanoyl]-L-leucyl-L-phenylalanine N-methylamide;
N-[2-Mercapto-5-phthalimidopentanoyl]-L-leucyl-L-phenylalanine N-methylamide;
N-[2-Mercapto-6-phthalimidohexanoyl]-L-leucyl-L-phenylalanine N-methylamide;
N-[2-Acetylmercapto-5-methoxycarbonylpentanoyl]-L-leucyl-L-phenylalanine N-methylamide;
N-[2-Acetylmercapto-6-methoxycarbonylhexanoyl]-L-leucyl-L-phenylalanine N-methylamide;
N-[2-Acetylmercapto-6-methoxycarbonylhexanoyl]-L-valinyl-L-phenylalanine N-methylamide;
N-[2-Acetylmercapto-6-methoxycarbonylhexanoyl]-L-leucyl-L-tryptophan N-methylamide;
N-[2-Acetylmercapto-5-phthalimidopentanoyl]-L-leucyl-L-phenylalanine N-methylamide;
N-[2-Acetylmercapto-5-phthalimidopentanoyl]-L-valinyl-L-phenylalanine N-methylamide;
N-[2-Acetylmercapto-5-phthalimidopentanoyl]-L-leucyl-L-tryptophan N-methylamide;
N-[2-Acetylmercapto-5-phthalimidopentanoyl]-L-leucyl-L-[β-(4-thiazolyl)]alanine N-methylamide;
N-[2-Acetylmercapto-5-phthalimidopentanoyl]-L-leucyl-L-[β-(2-pyridyl)]alanine N-methylamide;
N-[2-Acetylmercapto-5-phthalimidopentanoyl]-L-leucyl-5-methyl-L-glutamic acid N-methylamide;
N-[2-Acetylmercapto-6-phthalimidohexanoyl]-L-leucyl-L-phenylalanine N-methylamide;
N-[2-Acetylmercapto-2-(3-phthalimido)-phenylacetyl]-L-leucyl-L-phenylalanine N-methylamide;
N-[2-Mercapto-5-methoxycarbonylpentanoyl]-L-leucyl-L-phenylalanine N-methylamide;
N-[2-Mercapto-6-methoxycarbonylhexanoyl]-L-leucyl-L-phenylalanine N-methylamide;
N-[2-Mercapto-6-methoxycarbonylhexanoyl]-L-leucyl-L-tryptophan N-methylamide;
N-[2-Mercapto-5-phthalimidopentanoyl]-L-leucyl-L-phenylalanine N-methylamide;
N-[2-Mercapto-5-phthalimidopentanoyl]-L-leucyl-L-tryptophan N-methylamide;
N-[2-Mercapto-5-phthalimidopentanoyl]-L-leucyl-L-[β-(4-thiazolyl)alanine N-methylamide;
N-[2-Mercapto-5-phthalimidopentanoyl]-L-leucyl-L-[β-(2-pyridyl)]alanine N-methylamide;
N-[2-Mercapto-5-phthalimidopentanoyl]-L-leucyl-5-methyl-L-glutamic acid N-methylamide;
N-[2-Mercapto-6-phthalimidohexanoyl]-L-leucyl-L-phenylalanine N-methylamide;
N-Hydroxy-2(R)-[[4-methoxybenzenesulfonyl]-(3-picolyl)amino]-3-methylbutanamide;
N-Hydroxy-2(R)-[[4-methoxybenzenesulfonyl]-3-picolyl)amino]-2-cyclohexylacetamide;
N-Hydroxy-2(R)-[[4-methoxybenzenesulfonyl]-(benzyl)amino]-4-methylpentanamide;
N-Hydroxy-2(R)-[[4-methoxybenzenesulfonyl]-(benzyl)amino]-6-[(N,N-dimethylglycyl)amino]hexanamide hydrochloride;
N-Hydroxy-2(R)-[[4-methoxybenzenesulfonyl]-(3-picolyl)amino]-3-methylbutanamide;
N-Hydroxy-2(R)-[[4-methoxybenzenesulfonyl]-(4-picolyl)amino]-2-cyclohexylacetamide;
N-Hydroxy-2(R)-[(4-methoxybenzenesulfonyl]-(4-picolyl)amino]-2-(2-tetrahydrofuranyl)acetamide;
N-Hydroxy-2(R)-[[4-methoxybenzenesulfonyl]-(3-picolyl)amino]-3-methylbutanamide;
[4-(N-Hydroxyamino)-2R-isobutyl-3S-methyl-succinyl]-$N^2$(S)-piperazic acid N-methyl amide;
[4-(N-Hydroxyamino)-2R-isobutyl-3S-benzyl-succinyl]-$N^2$-(S)-piperazic acid N-methyl amide;
[4-(N-Hydroxyamino)-2R-isobutyl-3S-methoxyphenylsuccinyl]-$N^2$-(S)-piperazic acid N-methyl amide;
[4-(N-Hydroxyamino)-2R-isobutyl-3S-methoxybenzylsuccinyl]-$N^2$-(S)-piperazic acid N-methyl amide;
[4-(N-Hydroxyamino)-2R-isobutyl-3S-methylthiophenylsuccinyl]-$N^2$-(S)-piperazic acid N-methyl amide;
[4-(N-Hydroxyamino)-2R-isobutyl-3S-methylthiobenzylsuccinyl]-$N^2$-(S)-piperazic acid N-methyl amide;
[4-(N-Hydroxyamino)-2R-isobutyl-3S-(methylthio-2-thienyl)succinyl]-$N^2$-(S)-piperazic acid N-methyl amide;
[4-(N-Hydroxyamino)-2R-isobutyl-3S-methylacetate]-$N^2$-(S)-piperazic acid N-methyl amide;
[4-(N-Hydroxyamino)-2R-isobutyl-3S-methyl-isopropanoate]-$N^2$ (S)-piperazic acid N-methyl amide;

[4-(N-Hydroxyamino)-2R-isobutyl-3S-methyl-tert-butanoate]-$N^2$-(S)-piperazic acid N-methyl amide;

[4-(N-Hydroxyamino)-2R-isobutyl-3S-methyl-thioacetate]-$N^2$-(S)-piperazic acid N-methyl amide;

[4-(N-Hydroxyamino)-2R-isobutyl-3S-methyl-thioisopropanoate]-$N^2$-(S)-piperazic acid N-methyl amide;

[4-(N-Hydroxyamino)-2R-isobutyl-3S-methyl-(2-pyridyl)]-$N^2$-(S)-piperazic acid N-methyl amide;

[4-(N-Hydroxyamino)-2R-isobutyl-3S-methyl-(3-pyridyl)]-$N^2$-(S)-piperazic acid N-methyl amide;

[4-(N-Hydroxyamino)-2R-isobutyl-3S-methyl-(4-pyridyl)]-$N^2$-(S)-piperazic acid N-methyl amide;

[4-(N-Hydroxyamino)-2R-isobutyl-3S-methyl thio-tert-butanoate]-$N^2$-(S)-piperazic acid N-methyl amide;

[4-(N-Hydroxyamino)-2R-hexyl-3S-methylsuccinyl]-$N^2$-(S)-piperazic acid N-methyl amide;

[4-(N-Hydroxyamino)-2R-hexyl-3S-benzylsuccinyl]-$N^2$-(S)-piperazic acid N-methyl amide;

[4-(N-Hydroxyamino)-2R-hexyl-3S-methoxyphenyl-succinyl]-$N^2$-(S)-piperazic acid N-methyl amide;

[4-(N-Hydroxyamino)-2R-hexyl-3S-methoxybenzyl-succinyl]-$N^2$-(S)-piperazic acid N-methyl amide;

[4-(N-Hydroxyamino)-2R-hexyl-3S-methylthiophenyl-succinyl]-$N^2$-(S)-piperazic acid N-methyl amide;

[4-(N-Hydroxyamino)-2R-hexyl-3S-methylthiobenzyl-succinyl]-$N^2$-(S)-piperazic acid N-methyl amide;

[4-(N-Hydroxyamino)-2R-hexyl-3S-(methylthio-2-thienyl)succinyl]-$N^2$-(S)-piperazic acid N-methyl amide;

[4-(N-Hydroxyamino)-2R-hexyl-3S-benzylsuccinyl]-$N^2$-(S)-piperazic acid N-methyl amide;

[4-(N-Hydroxyamino)-2R-hexyl-3S-methyl acetate]-$N^2$-(S)-piperazic acid N-methyl amide;

[4-(N-Hydroxyamino)-2R-hexyl-3S-methyl-isopropanoate]-$N^2$-(S)-piperazic acid N-methyl amide;

[4-(N-Hydroxyamino)-2R-hexyl-3S-methyl tert-butanoate]-$N^2$-(S)-piperazic acid N-methyl amide;

[4-(N-Hydroxyamino)-2R-hexyl-3S-methylthio-acetate]-$N^2$-(S)-piperazic acid N-methyl amide;

[4-(N-Hydroxyamino)-2R-hexyl-3S-methylthio-isopropanoate]-$N^2$-(S)-piperazic acid N-methyl amide;

[4-(N-Hydroxyamino)-2R-hexyl-3S-methylthio-tert-butanoate]-$N^2$-(S)-piperazic acid N-methyl amide;

[4-(N-Hydroxyamino)-2R-hexyl-3S-methyl-(2-pyridyl)]-$N^2$-(S)-piperazic acid N-methyl amide;

[4-(N-Hydroxyamino)-2R-hexyl-3S-methyl-(3-pyridyl)]-$N^2$-(S)-piperazic acid N-methyl amide;

[4-(N-Hydroxyamino)-2R-hexyl-3S-methyl-(4-pyridyl)]-$N^2$-(S)-piperazic acid N-methyl amide;

[4-(N-Hydroxyamino)-2R-ethylphenyl-3S-methylsuccinyl]-$N^2$-(S)-piperazic acid N-methyl amide;

[4-(N-Hydroxyamino)-2R-ethylphenyl-3S-benzyl-succinyl]-$N^2$-(S)-piperazic acid N-methyl amide;

[4-(N-Hydroxyamino)-2R-ethylphenyl-3S-methoxy-phenylsuccinyl]-$N^2$-(S)-piperazic acid N-methyl amide;

[4-(N-Hydroxyamino)-2R-ethylphenyl-3S-methoxy-benzylsuccinyl]-$N^2$-(S)-piperazic acid N-methyl amide;

[4-(N-Hydroxyamino)-2R-ethylphenyl-3S-methylthio-phenylsuccinyl]-$N^2$-(S)-piperazic acid N-methyl amide;

[4-(N-Hydroxyamino)-2R-ethylphenyl-3S-methylthio-benzylsuccinyl]-$N^2$-(S)-piperazic acid N-methyl amide;

[4-(N-Hydroxyamino)-2R-ethylphenyl-3S-(methylthio-2-thienyl)succinyl]-$N^2$-(S)-piperazic acid N-methyl amide;

[4-(N-Hydroxyamino)-2R-ethylphenyl-3S-benzyl-succinyl]-$N^2$-(S)-piperazic acid N-methyl amide;

[4-(N-Hydroxyamino)-2R-ethylphenyl-3S-methyl acetate]-$N^2$-(S)-piperazic acid N-methyl amide;

[4-(N-Hydroxyamino)-2R-ethylphenyl-3S-methyl-isopropanoate]-$N^2$-(S)-piperazic acid N-methyl amide;

[4-(N-Hydroxyamino)-2R-ethylphenyl-3S-methyl-tert-butanoate]-$N^2$-(S)-piperazic acid N-methyl amide;

[4-(N-Hydroxyamino)-2R-ethylphenyl-3S-methyl-thioacetate]-$N^2$-(S)-piperazic acid N-methyl amide;

[4-(N-Hydroxyamino)-2R-ethylphenyl-3S-methylthio-isopropanoate]-$N^2$-(S)-piperazic acid N-methyl amide;

[4-(N-Hydroxyamino)-2R-ethylphenyl-3S-methylthio-tert-butanoate]-$N^2$-(S)-piperazic acid N-methyl amide;

[4-(N-Hydroxyamino)-2R-octyl-3S-methylsuccinyl]-$N^2$-(S)-piperazic acid N-methyl amide;

[4-(N-Hydroxyamino)-2R-octyl-3S-methylthiophenyl-succinyl]-$N^2$-(S)-piperazic acid N-methyl amide;

[4-(N-Hydroxyamino)-2R-octyl-3S-methylthiobenzyl-succinyl]-$N^2$-(S)-piperazic acid N-methyl amide;

[4-(N-Hydroxyamino)-2R-octyl-3S-methylthio-2-thienyl)succinyl]-$N^1$-(S)-piperazic acid N-methyl amide;

[4-(N-Hydroxyamino)-2R-octyl-3S-methyl acetate]-$N^2$-(S)-piperazic acid N-methyl amide;

[4-(N-Hydroxyamino)-2R-octyl-3S-methyl-isopropanoate]-$N^2$-(S)-piperazic acid N-methyl amide;

[4-(N-Hydroxyamino)-2R-octyl-3S-methyl tert-butanoate]-$N^2$-(S)-piperazic acid N-methyl amide;

[4-(N-Hydroxyamino)-2R-octyl-3S-methylthio-acetate]-$N^2$-(S)-piperazic acid N-methyl amide;

[4-(N-Hydroxyamino)-2R-octyl-3S-methylthio-isopropanoate]-$N^2$-(S)-piperazic acid N-methyl amide;

[4-(N-Hydroxyamino)-2R-octyl-3S-methylthio-tert-butanoate]-$N^2$-(S)-piperazic acid N-methyl amide;

[4-(N-Hydroxyamino)-2R-octyl-3S-methyl-(2-pyridyl)]-$N^2$-(S)-piperazic acid N-methyl amide;

[4-(N-Hydroxyamino)-2R-octyl-3S-methyl-(3-pyridyl)]-$N^2$-(S)-piperazic acid N-methyl amide;

[4-(N-Hydroxyamino)-2R-octyl-3S-methyl-(4-pyridyl)]-$N^2$-(S)-piperazic acid N-methyl amide;

[4-(N-Hydroxyamino)-2R-isobutyl-3S-methyl-succinyl]-$N^2$-(S)-4'(S/R)-benzylpiperazic acid N-methyl amide;

[4-(N-Hydroxyamino)-2R-isobutyl-3S-methyl-succinyl]-$N^2$-(S)-5'(S/R)-benzylpiperazic acid N-methyl amide;

[4-(N-Hydroxyamino)-2R-isobutyl-3S-methyl-succinyl]-$N^2$-(S)-6'(S/R)-benzylpiperazic acid N-methyl amide;

[4-(N-Hydroxyamino)-2R-isobutyl-3S-methyl-succinyl]-$N^2$-(S)-[5',6']benzopiperazic acid N-methyl amide;

N-[1(R)-Carboxy-ethyl]-α-(S)-isobutylglycine-(S)-$N^2$-piperazic acid methyl amide;

N-[1(R)-Carboxy-ethyl]-α-(S)-hexylglycine-(S)-$N^2$-piperazic acid methyl amide;

N-[1(R)-Carboxy-ethyl]-α-(S)-heptylglycine-(S)-$N^2$-piperazic acid methyl amide;

N-[1(R)-Carboxy-ethyl]-α-(S)-octylglycine-(S)-$N^2$-piperazic acid methyl amide;

N-[1(R)-Carboxy-ethyl]-α-(S)-ethylphenylglycine-(S)-$N^2$-piperazic acid methyl amide;

N-[1(R)-Carboxy-ethyl]-α-(S)-propylphenylclycine-(S)-$N^2$-piperazic acid methyl amide;

N-[1(R)-Carboxy-ethylthiobenzyl]-α-(S)-isobutyl-glycine-(S)-$N^2$-piperazic acid methyl amide;

N-[1(R)-Carboxy-ethylthiobenzyl]-α-(S)-hexyl-glycine-(S)-$N^2$-piperazic acid methyl amide;

N-[1(R)-Carboxy-ethylthiobenzyl]-α-(S)-ethyl-phenylglycine-(S)-$N^2$-piperazic acid methyl amide;

N-[1(R)-Carboxy-ethylthiobenzyl]-α-(S)-propyl-phenylglycine-(S)-$N^2$-piperazic acid methyl amide;

N-[1(R)-Carboxy-ethyloxybenzyl]-α-(S)-isobutyl-glycine-(S)-$N^2$-piperazic acid methyl amide;

N-[1(R)-Carboxy-ethyloxybenzyl]-α-(S)-hexyl-glycine-(S)-$N^2$-piperazic acid methyl amide;

N-[1(R)-Carboxy-ethyloxybenzyl]-α-(S)-ethyl-phenylglycine-(S)-$N^2$-piperazic acid methyl amide;

N-[1(R)-Carboxy-ethyloxybenzyl]-α-(S)-propyl-phenylglycine-(S)-N²-piperazic acid methyl amide;

N-[1(R)-Carboxy-4-(p-toluenesulfonyl)butyl]-α-(S)-phenethylglycyl-(S)-N²-piperazic acid methyl amide;

N-[1(R)-Carboxyethyl]-α-[2-(4-phenylphenoxy)-ethyl]-glycyl-(S)-N²-piperazic acid methyl amide;

2-[2(R)-[2-[1,1'-Biphenyl)yl]ethyl]-4-butyl-4(S)-carboxy-1-oxobutyl]-3(S)-methylaminocarbonyl-hexahydropyridazine;

2-[2(R)-[2-[1,1'-Biphenyl)yl]ethyl]-4-methyl-4(S)-carboxy-1-oxobutyl]-3(S)-methylaminocarbonyl-hexahydropyridazine;

2-[2(R)-[2-[1,1'-Biphenyl)yl]propyl]-4-butyl-4(S)-carboxy-1-oxobutyl]-3(S)-methylaminocarbonyl-hexahydropyridazine;

2-[2(R)-[2-(4-Propylphenyl)ethyl]-4-butyl-4(S)-carboxy-1-oxobutyl]-3(S)-methylaminocarbonyl-hexahydropyridazine;

2-[2(R)-[2-(4-Butylphenyl)ethyl]-4-butyl-4(S)-carboxy-1-oxobutyl]-3(S)-methylaminocarbonyl-hexahydropyridazine;

2-[2(R)-[2-(4-t-Butylphenyl)ethyl]-4-butyl-4(S)-carboxy-1-oxobutyl]-3(S)-methylaminocarbonyl-hexahydropyridazine;

2-[2(R)-[2-[4-(4-Fluorophenyl)phenyl]ethyl]-4-butyl-4(S)-carboxy-1-oxobutyl]-3(S)-methylamino-carbonyl-hexahydropyridazine;

2-[2(R)-[2-[4-(4-Fluorophenyl)phenyl]ethyl]-4-methyl-4(S)-carboxy-1-oxobutyl]-3(S)-methylamino-carbonyl-hexahydropyridazine;

2-[2(R)-[2-n-Octyl-4-methyl-4(S)-carboxy-1-oxobutyl]-3(S)-methylaminocarbonyl-hexahydropyridazine;

2-[2(R)-[2-[(4-Thiazolyl)phenyl]ethyl]-4-butyl-4(S)-carboxy-1-oxobutyl]-3(S)-methylaminocarbonyl-hexahydropyridazine;

2-[2(R)-[2-[(4-Thiazolyl)phenyl]ethyl]-4-methyl-4(S)-carboxy-1-oxobutyl]-3(S)-methylaminocarbonyl-hexahydropyridazine;

2-[2(R)-[2-[(4-Thiazolyl)phenyl]ethyl]-4-[3-(phenylsulfonyl)propyl-4(S)-carboxy-1-oxobutyl]-3(S)-methylaminocarbonyl-hexahydropyridazine;

2-[2(R)-[2-[(4-Thiazolyl)phenyl]ethyl]-4-(3-phenylpropyl)-4(S)-carboxy-1-oxobutyl]-3(S)-methylaminocarbonyl-hexahydropyridazine;

2-[2(R)-[2-[(4-Oxazolyl)phenyl]ethyl]-4-butyl-4(S)-carboxy-1-oxobutyl]-3(S)-methylaminocarbonyl-hexahydropyridazine;

2-[2(R)-[2-[(4-oxazolyl)phenyl]ethyl]-4-methyl-4(S)-carboxy-1-oxobutyl]-3(S)-methylaminocarbonyl-hexahydropyridazine;

2-[2(R)-[2-[(4-Oxazolyl)phenyl]ethyl]-4-[3-(phenylsulfonyl)propyl-4(S)-carboxy-1-oxobutyl]-3(S)-methylaminocarbonyl-hexahydropyridazine;

2-[2(R)-[2-[(4-Oxazolyl)phenyl]ethyl]-4-(3-phenylpropyl)-4(S)-carboxy-1-oxobutyl]-3(S)-methylaminocarbonyl-hexahydropyridazine;

2-[2(R)-[2-[4-(Dimethylamino)methylphenyl]ethyl]-4-butyl-4(S)-carboxy-1-oxobutyl]-3(S)-methylaminocarbonyl-hexahydropyridazine;

2-[2(R)-[2-[4-(Dimethylamino)methylphenyl]ethyl]-4-methyl-4(S)-carboxy-1-oxobutyl]-3(S)-methylaminocarbonyl-hexahydropyridazine;

2-[2(R)-[2-[4-(Dimethylamino)methylphenyl]ethyl]-4-[3-(phenylsulfonyl)propyl-4(S)-carboxy-1-oxobutyl]-3(S)-methylaminocarbonyl-hexahydropyridazine;

2-[2(R)-[2-[4-(Dimethylamino)methylphenyl]ethyl]-4-(3-phenylpropyl)-4(S)-carboxy-1-oxobutyl]-3(S)-methylaminocarbonyl-hexahydropyridazine;

2-[2(R)-[2-[(4-Imidazolyl)phenyl]ethyl]-4-butyl-4(S)-carboxy-1-oxobutyl]-3(S)-methylaminocarbonyl-hexahydropyridazine;

2-[2(R)-[2-[(4-Imidazolyl)phenyl]ethyl]-4-methyl-4(S)-carboxy-1-oxobutyl]-3(S)-methylaminocarbonyl-hexahydropyridazine;

2-[2(R)-[2-[(4-Imidazolyl)phenyl]ethyl]-4-[3-(phenylsulfonyl)propyl-4(S)-carboxy-1-oxobutyl]-3(S)-methylaminocarbonyl-hexahydropyridazine;

2-[2(R)-[2-[(4-Imidazolyl)phenyl]ethyl]-4-[3-(phenylpropyl)-4(S)-carboxy-1-oxobutyl]-3(S)-methylaminocarbonyl-hexahydropyridazine;

HS(CH$_2$)$_2$-(S-D-Leu)-Phe-NHMe;

HS(S) CHMeCH$_2$-(S-D-Leu)-Phe-NHMe;

HS(S)CH(PhtNBu)CH$_2$-(S-D-Leu)-Phe-NHMe;

HS(S)CH(PhtNEt)CH$_2$-(S-D-Leu)-Phe-NHMe;

HS(1,2-Cyclopentyl)(S-D-Leu)-Phe-NHMe

Me-S(NH)$_2$-(CH$_2$-DL-Leu)-Trp-NHBn;

n-Bu-S(NH)$_2$-(CH$_2$-DL-Leu)-Trp-NHBn;

n-Bu-S(NH)$_2$-(CH$_2$-DL-TyrOCH$_3$)-Trp-NHBn;

Me-RS-SO(NH)-(CH$_2$-L-Leu)-Phe-Ala-NH$_2$;

n-Bu-RS-SO(NH)-(CH$_2$-L-Leu)-Phe-Ala-NH$_2$;

$$\text{HOHN}-\underset{\underset{\text{O}}{\|}}{\text{C}}-\text{CH}_2\text{CH}(\text{CH}_2\text{CH}(\text{CH}_3)_2)-\text{CO}-\text{Nal}-\text{Ala}-\text{NH}_2;$$

HO-NH-CO-CH$_2$-CH-(CH$_2$-CH(CH$_3$)$_2$-CO-Nal-Pro-NH$_2$;

HO-NH-CO-CH(CH$_3$-CH(CH$_2$)-CH(CH$_3$)$_2$)-CO-Nal-Ala-NH$_2$;

$$\text{HON}-\overset{\text{H}}{\overset{|}{\text{N}}}-\text{COCH}_2-\text{CH}-\text{CO}-\text{Pal}-\text{Ala}-\text{NH}_2,$$

wherein Pal is 3-pyridylalanine;

$$\text{HON}-\overset{\text{H}}{\overset{|}{\text{N}}}-\text{COCH}_2-\text{CH}-\text{CO}-\text{Nal}-(\text{CH}_2\text{S})\text{Ala}-\text{NH}_2$$

HO-NH-CO-CH$_2$-CH(CH$_2$CH(CH$_3$)$_2$)-CONal-(CH$_2$NH)-Ala-NH$_2$;

-continued

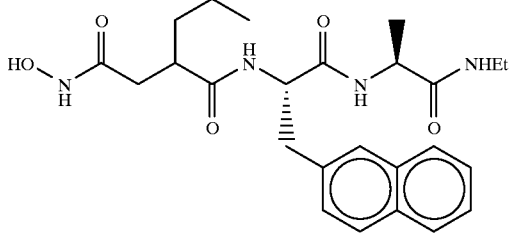

4-(1,3-Dihydro-1,3-dioxo-2H-benz[f]isoindol-2-yl)-2-(R)-[[3-methyl-1-(S)-[[(2-morpholin-4-ylethyl)amino]-carbonyl]butyl]amino]-butanoic acid;
4-(1,3-Dihydro-1,3-dioxo-2H-benz[f]isoindol-2-yl)-2-(R)-[[3-methyl-1-(S)-[[methylamino]carbonyl]butyl]-amino]-butanoic acid;
4-(1,3-Dihydro-1,3-dioxo-2H-benz[f]isoindol-2-yl)-2-(R)-[[3-methyl-1-(S)-[[(1H-imidazol-2-ylmethyl)-amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1H-tetrazol-5-ylmethyl)-amino]carbonyl]butyl]amino]-butanoic acid;
4-(1,3-Dihydro-1,3-dioxo-2H-benz[f]isoindol-2-yl)-2-(R)-[[3-methyl-1-(S)-[[[(2-(phenyl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(2-methyl-2H-tetrazo-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-hydroxy-2-methyl-pyrimidin-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[2-(2-pyridin-3-yl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[1-(1H-tetrazol-5-yl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(5-amino-4H-[1,2,4]-triazol-3-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(6-oxo-1,6-dihydro-pyridazin-3-yl)ethyl]amino]carbonyl]butyl]amino]-butanoic acid;

4-(1,3-Dihydro-1,3-dioxo-2H-benz[f]isoindol-2-yl)-2-(R)-[[3-methyl-1-(S)-[[(phenyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(benzyl)amino]carbonyl]butyl]amino]-butanoic acid;
4-(1,3-Dihydro-1,3-dioxo-2H-benz[f]isoindol 2-yl)-2-(R)-[[3-methyl-1-(S)-[[(pyridin-4-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[2-(1H-imidazol-4-yl)ethyl]amino]carbonyl]butyl]amino]-butanoic acid;
4-(1,3-Dihydro-1,3-dioxo-2H-benz[f]isoindol-2-yl)-2-(R)-[(3-methyl-1-(S)-[[(pyridin-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-sulfamoyl-phenyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-sulfamoyl-phenyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-dimethylamino-benzyl)-amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(S)-phenyl-ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(2,4-difluoro-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-methanesulfonylamino-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-methanesulfonylamino-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3,4-difluoro-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-trifluoromethyl-benzyl)amino]carbonyl]butyl]amino]-butanoic acid;

4- [2-(S)-[1-(R)-Carboxy-3-(1,3-dioxo-1,3-dihydro-benzo[f]isoindol-2-yl)-propylamino]-4-methyl-pentanoylamino-methyl)-benzoic acid;

4-(1,3-Dihydro-1,3-dioxo-2H-benz[f]isoindol-2-yl)-2-(R)-[[3-methyl-1-(S)-[[(2-hydroxy-1,1-bis-hydroxymethyl-ethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3,5-difluoro-benzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[benzylmethyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-dimethylaminoethyl)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[[(1-azabicyclo[2.2.2]-oct-3(R)-amino]carbonyl]butyl]amino]-butanoic acid;

4-(1,3-Dihydro-1,3-dioxo-2H-benz[f]isoindol-2-yl)-2-(R)-[[3-methyl-1-(S)-[[(1-azabicyclo[2.2.2]oct-3-(S)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-(R)-4-(S)-5-(R)-6-tetrahydroxtetrahydra-pyran-2-(R)-ylmethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(N,N'-dimethyl-hydrazino)-carbonyl]butyl]amino]-butanoic acid;

4-(1,3-Dihydro-1,3-dioxo-2H-benz[f]isoindol-2-yl)-2-(R)-[[3-methyl-1-(S)-[[(methylmethoxy)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-oxo-tetrahydro-thiophen-3-(S)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydro-pyran-2-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[[benzyl(2-hydroxyethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[3,4-dihydro-1H-isoquinoline-2-carbonyl]butyl]amino]-butanoic acid;

4-(1,3-Dihydro-1,3-dioxo-2H-benz[f]isoindol-2-yl)-2-(R)-[[3-methyl-1-(S)-[4-methylpiperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[1-oxo-[1,4]thiazinane-4-carbonyl]butyl]amino]-butanoic acid;

4-(1,3-Dihydro-1,3-dioxo-2H-benz[f]isoindol-2-yl)-2-(R)-[[3-methyl-1-(S)-[morpholine-4-carbonyl]butyl]amino]-butanoic acid;

4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1]carbonyl]butyl]amino]-butanoic acid;

4-(1,3-Dihydro-1,3-dioxo-2H-benz[f]isoindol-2-yl)-2-(R)-[[3-methyl-1-(S)-[[(1-methyl-8-oxo-1,7-diazacyclotridec-9-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[methyl-1-methyl-piperidin-4-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(4-hydroxy-1,1-dioxo-tetrahydro-thiophen-3-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic acid;

4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[2-(R)-(pyridin-3-yl)-pyrrolidinecarbonyl]butyl]amino]-butanoic acid;

4-(1,3-Dihydro-1,3-dioxo-2H-benz[f]isoindol-2-yl)-2-(R)-[[3-methyl-1-(S)-[2-(S)-(pyridin-3-yl)-pyrrolidinecarbonyl]butyl]amino]-butanoic acid;

4-(1,3-Dihydro-1,3-dioxo-2H-benz[f]isoindol-2-yl)-2-(R)-[[3-methyl-1-(S)-[3-oxo-2-(R)-phenyl-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[3-oxo-2-(S)-phenyl-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[(pyridine-3-carbonyl-hydrazino)carbonyl]butyl]amino]-butanoic acid;

4-(1,3-Dihydro-1,3-dioxo-2H-benz[f]isoindol-2-yl)-2-(R)-[[3-methyl-1-(S)-[[(benzenesulfonyl)amino]-carbonyl]butyl]amino]-butanoic acid;

4-(1,3-Dihydro-1,3-dioxo-2H-benz[f]isoindol-2-yl)-2-(R)-[[3-methyl-1-(S)-[[(3-aminobenzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[[4-(trifluoro-methanesulfonyl-amino)benzyl]amino]carbonyl]butyl]amino]-butanoic acid;

4-(1,3-Dihydro-1,3-dioxo-2H-benz[f]isoindol-2-yl)-2-(R)-[[3-methyl-1-(S)-[[[2-hydroxy-(R)-bicyclo[4.3.0]-nona-3,6(1)-diene]amino]carbonyl]butyl]amino]-butanoic acid;

4-(1,3-Dihydro-1,3-dioxo-2H-benz[f]isoindol-2-yl)-2-(R)-[[3-methyl-1-(S)-[[[2-hydroxy-(S)-bicyclo[4.3.0]-nona-3,6(1)-diene]amino]carbonyl]butyl]amino]-butanoic acid;

4-(1,3-Dihydro-1,3-dioxo-2H-benz[f]isoindol-2-yl)-2-(R)-[[3-methyl-1-(S)-[[(N-methyl-pyrrolidine)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[(N-ethoxycarbonylmethyl-piperazine)-1-carbonyl]butyl]amino]-butanoic acid;

2-(R)-[1-(S)-(Benzylamino)carbonyl-3-methyl-butylamino]-4-(5-bromo-1,3-dioxo-1,3-dihydro-isoindol-2-yl)-butanoic acid;

2-(R)-[1-(S)-(Benzylamino)carbonyl-3-methyl-butylamino]-4-(5-propoxy-1,3-dioxo-1,3-dihydro-isoindol-2-yl)-butanoic acid;

2-(R)-[1-(S)-(Benzylamino)carbonyl-3-methyl-butylamino]-4-(5-nitro-1,3-dioxo-1,3-dihydro-isoindol-2-yl)-butanoic acid;

2-(R)-[1-(S)-(Benzylamino)carbonyl-3-methyl-butylamino]-4-(5-amino-1,3-dioxo-1,3-dihydro-isoindol-2-yl)-butanoic acid;

2-(R)-[1-(S)-(Benzylamino)carbonyl-3-methyl-butylamino]-4-(5-methyl-1,3-dioxo-1,3-dihydro-isoindol-2-yl)-butanoic acid;

2-(R)-[1-(S)-(Benzylamino)carbonyl-3-methyl-butylamino]-4-(5-methoxy-1,3-dioxo-1,3-dihydro-isoindol-2-yl)-butanoic acid;

2-(R)-[1-(S)-(Benzylamino)carbonyl-3-methyl-butylamino]-4-(5-benzyloxy-1,3-dioxo-1,3-dihydro-isoindol-2-yl)-butanoic acid;

2-(R)-[1-(S)-(Benzylamino)carbonyl-3-methyl-butylamino]-4-(5-phenyl-1,3-dioxo-1,3-dihydro-isoindol-2-yl)-butanoic acid;

2-(R)-[1-(S)-(Benzylamino)carbonyl-3-methyl-butylamino]-4-(1,3-dioxo-1,3-dihydro-isoindol-2-yl)-butanoic acid;

2-(R)-[1-(S)-(Benzylamino)carbonyl-3-methyl-butylamino]-4-(5-methanesulfonylamino-1,3-dioxo-1,3-dihydro-isoindol-2-yl)-butanoic acid;

2-(R)-[1-(S)-(Benzylamino)carbonyl-3-methyl-butylamino]-4-(5-benzenesulfonylamino-1,3-dioxo-1,3-dihydro-isoindol-2-yl)-butanoic acid;

2-(R)-[1-(S)-(Benzylamino)carbonyl-3-methyl-butylamino]-4-(5-hydroxy-1,3-dioxo-1,3-dihydro-isoindol-2-yl)-butanoic acid;

2-(R)-[[3-Methyl-1-(S)-[[(pyridin-3-ylmethyl)-amino]carbonyl]butyl]amino]-4-(1,3,5,7-tetraoxo-3,5,6-tetrahydro-1H-pyrolo[3,4-f]isoindol-2-yl)butanoic acid;

EtONHCONMe-CH$_2$CH(iBu)-CO-L-Trp-NHEt;
EtCONOH-CH$_2$CH(iBu)-CO-L-Trp-NHEt;
n-PrCONOEt-CH$_2$CH(iBu)-CO-L-Trp-NHEt;
EtNHCONOMe-CH$_2$CH(iBu)-CO-L-Trp-NHEt;
MeNHCONOH-CH$_2$CH(iBu)-CO-L-Trp-NHEt;
EtONHCONMe-CH$_2$CH(iBu)-CO-L-Ala(2-naphthyl)-NHEt;
EtCONOH-CH$_2$CH(iBu)-CO-L-Ala(2-naphthyl)-NHEt;
n-PrCONOEt-CH$_2$CH(iBu)-CO-L-Ala(2-naphthyl)-NHEt;
EtNHCONOMe-CH$_2$CH(iBu)-CO-L-Ala(2-naphthyl)-NHEt;
MeNHCONOH-CH$_2$CH(iBu)-CO-L-Ala(2-naphthyl)-NHEt;
HONHCONHCH$_2$CH(iBu)-CO-L-TrpNHMe;
HONHCONHCH$_2$CH$_2$CH(iBu)-CO-L-TrpNHMe;
HONHCONHCH(iBu)-CO-L-TrpNHMe;
H$_2$NCON(OH)CH(iBu)-CO-L-TrpNHMe;
N(OH)CH$_2$CH(iBu)-CO-L-TrpNHMe;
H$_2$NCON(OH)CH$_2$CH$_2$CH(iBu)-CO-L-TrpNHMe;
CH$_3$CON(OH)CH(iBu)-CO-L-TrpNHMe;
CH$_3$CON(OH)CH$_2$CH(iBu)-CO-L-TrpNHMe;
CH$_3$CON(OH)CH$_2$CH$_2$CH(iBu)-CO-L-TrpNHMe;
NHOHCOCH$_2$CH(i-Bu)CO-L-Trp-NHMe;

HONHCONHCH$_2$CH(i-Bu)CONHCHCOOH
|
R$^4$ or

ROOCCH$_2$CH(i-Bu)CONHCHCOOH;
|
R$^4$

N-{D,L-2-(Hydroxyaminocarbonyl)methyl-4-methylpentanoyl}-L-3-(2'-naphthyl)alanyl-L-alanine, 2-(amino)ethyl amide;

N-{D,L-2-(Hydroxyaminocarbonyl)methyl-4-methylpentanoyl}-L-3-amino-2-dimethylbutanoyl-L-alanine, 2-(amino)ethyl amide;

4(S)-[3-Hydroxyaminocarbonyl-2(R)-(2-methylpropyl)propanoyl]amino-1,2,3,4-tetrahydro-3H-2-benzazepin-3-one;

[4-(N-Hydroxyamino)-(2R)-isobutyl-3-methylsuccinyl]-L-phenylglycine-N-methylamide;

4(S)-[2(R)-[1(R)-Hydroxycarbamoyl-2-morpholinoethyl]-4-methylvaleryl]amino-1,2,4,5-tetrahydro-3H-2-benzazepine-3-one;

(1R,4S)-4-[(2R)-Hydroxycarbamoylmethyl-4-methylvaleryl]amino-3-oxo-1,2,4,5-tetrahydro-3H-2-benzazepine-1-carboxylic acid;

3-[2-(N-Methylcarbamoyl)ethylsulfinyl]-5-methylhexanohydroxamic acid;

N-[(2-Thenoylmercapto-3-methyl)-butanoyl]-homocysteine thiolactone;

N-[1(R)-Carboxy-ethyl]-α-(S)-(2-phenyl-ethyl)-glycine-(L)-leucine, N-phenylamide;
N-[1(R)-Carboxy-ethyl]-α-(S)-(2-phenyl-ethyl)-glycine-(L)-isoleucine, N-phenylamide;
N-[1(R)-Carboxy-ethyl]-α-(S)-(2-phenyl-ethyl)-glycine-(L)-alanine, N-phenylamide;
N-[1(R)-Carboxy-ethyl]-α-(S)-(2-phenyl-ethyl)-glycine-(L)-phenylalanine, N-phenylamide;
N-[1(R)-Carboxy-ethyl]-α-(S)-(2-phenyl-ethyl)-glycine-(L)-serine-O-benzyl ether, N-phenylamide;
N-[1(R)-Carboxy-ethyl]-α-(S)-(2-phenyl-ethyl)-glycine-(L)-tryptophan, N-phenylamide;
N-[1(R)-Carboxy-ethyl]-α-(S)-(2-phenyl-ethyl)-glycine-α-(S)-(2-phenyl-ethyl)glycine, N-phenylamide;
N-[1(R)-Carboxy-ethyl]-α-(S)-(2-phenyl-ethyl)-glycine-(L)-norleucine, N-phenylamide;
N-[1(R)-Carboxy-ethyl]-α-(S)-(2-phenyl-ethyl)-glycine-(L)-valine, N-phenylamide;
N-[1(R)-Carboxy-ethyl]-α-(S)-(2-phenyl-ethyl)-glycine-(L)-serine, N-phenylamide hydrochloride;
N-[1(R)-Carboxy-ethyl]-α-(S)-(2-phenyl-ethyl)-glycine-(L)-asparagine, N-phenylamide;
N-[1(R)-Carboxy-ethyl]-α-(S)-(2-phenyl-ethyl)-glycine-(L)-threonine, N-phenylamide hydrochloride;
N-[1(R)-Carboxy-ethyl]-α-(S)-(2-phenyl-ethyl)-glycine-(L)-lysine, N-phenylamide;
N-[1(R)-Carboxy-ethyl]-α-(S)-(2-phenyl-ethyl)-glycine-(L)-glutamic acid, N-phenylamide;
N-[1(R)-Carboxy-ethyl]-α-(S)-(2-phenyl-ethyl)-glycine-(L)-tyrosine, N-phenylamide hydrochloride;
N-[1(R)-Carboxy-5-(1,3-dioxo-isoindolin-2-yl)pentyl]-α-(S)-(2-phenyl-ethyl)glycine-(L)-leucine, N-phenylamide;
N-[1(R)-Carboxy-5-(1-oxo-isoindolin-2-yl)pentyl]-α-(S)-(2-phenyl-ethyl)glycine-(S)-leucine, N-phenylamide hydrochloride;
N-[1(R)-Carboxy-5-(1-oxo-isoindolin-2-yl)pentyl]-α-(S)-(2-phenyl-ethyl)glycine-(S)-arginine, N-phenylamide;
N-[1(R)-Carboxy-ethyl]-α-(S)-(2-(3-hydroxyphenyl)-ethyl)glycine-(S)-leucine, N-phenylamide hydrochloride;
N-[1(R)-Carboxy-ethyl]-α-(S)-(2-(4-methylphenyl)-ethyl)glycine-(S)-leucine, N-phenylamide hydrochloride;
N-[1(R)-Carboxy-ethyl]-α-(S)-(2-(2'-thienyl)ethyl)glycine-(L)-leucine, N-phenylamide;
N-[1(R)-Carboxy-ethyl]-α-(S)-(2-(4-ethylphenyl)-ethyl)glycine-(L)-leucine, N-phenylamide;
N-[1(R)-Carboxy-5-(1-oxo-isoindolin-2-yl)pentyl]-α-(S)-(2-(4-propylphenyl)ethyl)glycine-(L)-leucine, N-phenylamide;
N-[1(R)-Carboxy-ethyl]-α-(S)-(2-(4-chlorophenyl)-ethyl)glycine-(L)-leucine, N-phenylamide;
N-[1(R)-Carboxy-ethyl]-α-(S)-(2-phenyl-ethyl)-glycine-α-(S)-(2-cyclohexyl-ethyl)glycine, N-phenylamide;
N-[1(R)-Carboxy-ethyl]-α-(S)-(2-phenyl-ethyl)-glycine-α-(S)-(cyclohexyl)glycine, N-phenylamide;
N-[1(R)-Carboxy-ethyl]-α-(S)-(2-phenyl-ethyl)-glycine-α-(S)-(cyclohexylmethyl)glycine, N-phenylamide;
N-[1(R)-Carboxy-ethyl]-α-(S)-(2-phenyl-ethyl)-glycine-(L)-β-naphthylalanine, N-phenylamide;

N-[1(R)-Carboxy-ethyl]-α-(S)-(2-phenyl-ethyl)-glycine-(L)-α-naphthylalanine, N-phenylamide;

N-[1(R)-Carboxy-ethyl]-α-(S)-(2-phenyl-ethyl)-glycine-[(L)-glutamic acid, α,δ-bis-N-phenylamide;

N-[1(R)-Carboxy-ethyl]-α-(S)-(2-phenyl-ethyl)-glycine-(L)-leucine, N-cyclohexylamide;

N-[(1(R)-Carboxy-ethyl)]-α-(S)-(2-phenyl-ethyl)-glycine-α-(S)-(4-hydroxyphenyl-ethyl)glycine, N-phenylamide;

N-[1(R)-Carboxy-ethyl]-α-(S)-(2-phenyl-ethyl)-glycine-(L)-phenylglycine, N-phenylamide;

N-[1(R)-Carboxy-ethyl]-α-(S)-(2-phenyl-ethyl)-glycine-(L)-glutamic acid, $N_\delta$-benzylamide, $N_\alpha$-phenylamide;

N-[1(R)-Carboxy-ethyl]-α-(S)-(2-phenyl-ethyl)-glycine-(L)-ornithine, N-phenylamide;

N-[1(R)-Carboxy-ethyl]-α-(S)-(2-phenyl-ethyl)-glycine-(L)-arginine, N-phenylamide;

N-[1(R)-Carboxy-ethyl]-α-(S)-(2-phenyl-ethyl)-glycine-α-(S)-(3-phenylpropyl)glycine, N-phenylamide;

N-[1(R)-Carboxy-ethyl]-α-(S)-(2-phenyl-ethyl)-glycine-α-(S)-n-octylglycine, N-phenylamide;

N-[1(R)-Carboxy-ethyl]-α-(S)-(2-phenyl-ethyl)-glycine-(L)-leucine, N-(4-carboxyphenyl)amide;

N-[1(R)-Carboxy-ethyl]-α-(S)-(2-phenyl-ethyl)-glycine-(L)-leucine, N-(4-trifluoromethylphenyl)amide;

N-[1(R)-Carboxy-ethyl]-α-(S)-(2-phenyl-ethyl)-glycine-(L)-leucine, N-(3-pyridyl)amide;

N-[1(R)-Carboxy-ethyl]-α-(S)-(2-phenyl-ethyl)-glycine-(L)-leucine, N-(benzothiazol-2-yl)amide;

N-[1(R)-Carboxy-ethyl]-α-(S)-(2-(4-n-propylphenyl)ethyl)glycine-(L)-leucine, N-phenylamide;

N-[1(R)-Carboxy-ethyl]-α-(S)-(2-4-propylphenyl)-ethyl)glycine-(L)-arginine, N-phenylamide;

N-[1(R)-Carboxy-ethyl]-α-(S)-(2-(3,4-dimethylphenyl-ethyl)glycine-(L)-leucine, N-phenylamide;

(2-(((4-(1,3-Dihydro-1,3-dioxo-2H-isoindol-2-yl)-butyl)hydroxyphosphinyl)methyl)-4-phenylbutanoyl)-L-leucine, N-phenylamide;

(2-(((4-(1,3-Dihydro-1-oxo-2H-isoindol-2-yl)-butyl)hydroxyphosphinyl)methyl)-4-phenylbutanoyl)-L-leucine, N-phenylamide;

(2-(((4-(1,3-Dihydro-1-oxo-2H-isoindol-2-yl)-butyl)(2-methyl-1-(1-oxopropoxy)propoxy)phosphinyl)-methyl)-4-phenylbutanoyl)-L-leucine, N-phenylamide;

(2-((Hydroxy(methyl)phosphinyl)methyl)-4-phenylbutanoyl)-L-leucine, N-phenylamide;

[[Hydroxy[1(R)-[N-(N-acetyl-L-prolyl-L-alanyl)-amino]-ethyl]-phosphinyl]-methyl]-4-phenyl-butanoyl-L-leucyl, N-phenylamide;

[Hydroxy-[N-(N-(benzoyl)-L-prolyl)aminobutyl]-phosphinyl]methyl]-4-phenyl-butanoyl-L-leucine, N-phenylamide;

[Hydroxy-[2-Methylpropyloxycarbonyl-aminobutyl]-phosphinyl]methyl]-4-phenylbutanoyl-L-leucine, N-phenylamide;

[Hydroxy-[1-Methylethylaminocarbonyl-aminobutyl]-phosphinyl]methyl]-4-phenylbutanoyl-L-leucine, N-phenylamide;

N-(2-Thiomethyl-4-phenylbutanoyl)-(L)-leucinamide;

N-(2-Thiomethyl-4-phenylbutanoyl)-(L)-leucine, N-phenylamide;

N-(2-Thiomethyl-4-phenylbutanoyl)-(L)-leucine, N-benzylamide;

N-(2-Thiomethyl-4-phenylbutanoyl)-(L)-leucine, N-(2-phenylethyl)amide;

N-(2-Thiomethyl-4-phenylbutanoyl)-(L)-phenylalaninamide;

N-(2-Thiomethyl-4-phenylbutanoyl)-(L)-phenylalanine N-phenylamide;

N-(2-Thiomethyl-4-phenylbutanoyl)-(L)-phenylalanine N-benzylamide;

N-(2-Thiomethyl-4-phenylbutanoyl)-(L)-phenylalanine-b-alanine;

2(R)-(2-(4-(1-n-Propyl)phenyl)ethyl)-1,5-pentanedioic acid 1-(L-leucine, N-phenylamide)amide;

2(R)-(2-(4-(1-n-Propyl)phenyl)ethyl)-1,5-pentanedioic acid 1-(2(S)-t-butyl)glycine, N-phenylamide)amide;

2(R)-(2-(4-(1-n-Propyl)phenyl)ethyl)-1,5-pentanedioic acid 1-(2(S)-t-butyl)glycine, N-(4-pyridylamide)amide;

2(R)-(2-(4-(1-n-Propyl)phenyl)ethyl)-1,5-pentanedioic acid 1-(L-arginine, N-methylamide)amide;

2(R)-(2-(4-(1-n-Propyl)phenyl)ethyl)-4-methyl-1,5-pentanedioic acid 1-(L-leucine, N-phenylamide)amide;

2(R)-(2-(4-(1-n-Propyl)phenyl)ethyl)-4-methyl-1,5-pentanedioic acid 1-(2(S)-t-butyl)glycine, N-phenylamide)amide;

2(R)-(2-(4-(1-n-Propyl)phenyl)ethyl)-4-methyl-1,5-pentanedioic acid 1-(2(S)-(4-thiazolylmethyl)glycine, N-phenylamide)amide;

2(R)-(2-(4-(1-n-Propyl)phenyl)ethyl)-4-methyl-1,5-pentanedioic acid 1-(2(S)-(3-pyridylmethyl)glycine, N-phenylamide)amide;

2(R)-(2-(4-(1-n-Propyl)phenyl)ethyl)-4-methyl-1,5-pentanedioic acid 1-(L-leucine, N-(4-pyridyl)amide)amide;

2(R)-(2-(4-(1-n-Propyl)phenyl)ethyl)-4-methyl-1,5-pentanedioic acid 1-(2(S)-(2-pyridylmethyl)glycine, N-phenylamide)amide;

2(R)-(2-(4-(1-n-Propyl)phenyl)ethyl)-4-methyl-1,5-pentanedioic acid 1-(L-arginine, N-phenylamide)amide;

2(R)-(2-(4-(1-n-Propyl)phenyl)ethyl)-4-methyl-1,5-pentanedioic acid 1-(L-phenylalanine, N-4-pyridylamide)amide;

2(R)-(2-(4-(1-n-Propyl)phenyl)ethyl)-4-(1-(4-(N-(2-oxoisoindolinyl))-butyl))-1,5-pentanedioic acid 1-(L-leucine, N-phenylamide)amide;

2(R)-(2-(4-(1-n-Propyl)phenyl)ethyl)-4-(1-(4-(N-(2-oxoisoindolinyl))-but-2-enyl))-1,5-pentanedioic acid 1-(L-leucine, N-phenylamide)amide;

2(R)-(2-(4-(4-Fluorophenyl)phenyl)ethyl)-4-methyl-1,5-pentanedioic acid 1-(L-leucine, N-phenylamide)amide;

2(R)-(2-(4-(Phenyl)phenyl)ethyl)-4-methyl-1,5-pentanedioic acid 1-(L-leucine, N-phenylamide)amide;

2(R)-(2-(4-(4-Methoxyphenyl)phenyl)ethyl)-4-methyl-1,5-pentanedioic acid 1-(L-leucine, phenylamide)amide;

2(R)-(2-(4-(4-Methylphenyl)phenyl)ethyl)-4-methyl-1,5-pentanedioic acid 1-(L-leucine, phenylamide)amide;

2(R)-(2-(4-(4-Hydroxy-n-butyl)-phenyl)-ethyl)-4-methylpentanedioic acid 1-(S-leucine, phenylamide)amide;

2(R),4(S)-(2-(4-(3-Hydroxy-n-propyl)phenyl)ethyl)-4-methyl-1,5-pentanedioic acid 1-(L-leucine, N-phenylamide)amide;

2(R)-(2-Phenylethyl)-4-methyl-1,5-pentanedioic acid 1-(L-leucine, N-phenylamide)amide;

2(R)-(2-(4-(1-n-Propyl)phenyl)ethyl)-1,5-pentanedioic acid 1-(L-leucine, N-ethylamide)amide;

2(R)-(2-(4-(1-n-Propyl)phenyl)ethyl)-1,5-pentanedioic acid 1-(L-leucine, N-isopropylamide)amide;

2(R)-(2-(4-(1-n-Propyl)phenyl)propyl)-1,5-pentanedioic acid 1-(2(S)-tri-butyl-glycine, N-4-pyridyl)amide)amide;

2(R)-(3-(4-(1-n-Propyl)phenyl)propyl)-1,3-pentanedioic acid 1-(L-leucine, N-phenylamide)amide;

2(R)-(2-(4-(1-n-Propyl)phenyl)ethyl)-4-hexyl-1,5-pentanedioic acid 1-(L-leucine, N-phenylamide)amide;

2(R)-(2-(4-(1-n-Propyl)phenyl)ethyl)-4-butyl-1,5-pentanedioic acid 1-(L-leucine, N-phenylamide)amide;

2(R)-(2-(4-(1-n-Propyl)phenyl)ethyl)-4-(3-methylbenzyl)-1,5-pentanedioic acid 1-(L-leucine, N-phenylamide)amide;

2(R)-(2-(4-(1-n-Propyl)phenyl)ethyl)-4-(2-benzimidazolyl)butyl)-1,5-pentanedioic acid 1-(L-leucine, N-phenylamide)amide;

2(R)-(2-(4-(1-n-Propyl)phenyl)ethyl)-4-(2-benzthiazolyl)butyl)-1,5-pentanedioic acid 1-(L-leucine, N-phenylamide)amide;

2(R)-(2-(4-(1-n-Propyl)phenyl)ethyl)-4-(2-benzoxazolyl)butyl)-1,5-pentanedioic acid 1-(L-leucine, N-phenylamide)amide;

2(R)-(2-(4-(1-n-Propyl)phenyl)ethyl)-4-carboxy-1,9-nonanedioic acid 1-(L-leucine, N-phenylamide)amide 9-piperidineamide;

2(R)-(2-(4-(1-Propyl)phenyl)ethyl)-4-carboxy-1,9-nonanedioic acid 1-(L-leucine, N-methylamide)amide 9-phenylamide;

2(R)-(2-(4-(1-n-Propyl)phenyl)ethyl)-4-carboxy-1,9-nonanedioic acid 1-(L-leucine, N-methylamide)amide 9-tert-butylamide;

2(R)-(2-(4-(1-n-Propyl)phenyl)ethyl)-4-carboxy-1,9-nonanedioic acid 1-(L-leucine, N-methylamide)amide 9-benzylamide;

2(R)-(2-(4-(1-n-Propyl)phenyl)ethyl)-4-carboxy-1,9-nonanedioic acid 1-(L-leucine, N-methylamide)amide 9-morpholineamide;

2(R)-(2-(4-(1-n-Propyl)phenyl)ethyl)-4-carboxy-1,9-nonanedioic acid 1-(L-leucine, N-methylamide)amide 9-(1(R)-phenylethyl)amide;

2(R)-(2-(4-(1-n-Propyl)phenyl)ethyl)-4-carboxy-1,9-nonanedioic acid 1-(L-leucine, N-methylamide)amide 9-(1(S)-phenylethyl)amide;

2(R)-(2-(4-(1-n-Propyl)phenyl)ethyl)-4-carboxy-1,9-nonanedioic acid 1-(L-leucine, N-methylamide)amide 9-(N-methyl-N-phenyl)amide;

2(R)-(2-(4-(1-n-Propyl)phenyl)ethyl)-4-carboxy-1,9-nonanedioic acid 1-(L-leucine, N-methylamide)amide 9-(N'-methylpiperazine)amide trifluoroacetic acid salt;

2(R)-(2-(4-(1-n-Propyl)phenyl)ethyl)-4-carboxy-1,9-nonanedioic acid 1-(L-leucine, N-methylamide)amide 9-(3-pyridyl)amide;

2(R)-(2-(4-(1-Propyl)phenyl)ethyl)-4-carboxy-1,9-nonanedioic acid 1-(L-leucine, N-methylamide)amide;

2(R)-(2-(4-(1-Propyl)phenyl)ethyl)-1,5-pentanedioic acid 1-((R)-(S-p-methoxybenzyl)-penicillamine, N-phenylamide)amide;

2(R)-(2-(4-(1-Propyl)phenyl)ethyl)-1,5-pentanedioic acid 1-((R)-(S-p-methoxybenzyl)-penicillamine sulfone, N-phenylamide)amide;

2-(2-(4-(1-Propyl)phenyl)ethyl)-4-(1-(4-(2-phthalimido))butyl)-1,5-pentandioic acid 1-(L-leucine, N-methylamide)amide;

2(R)-(2-(4-(1-n-Propyl)phenyl)ethyl)-4-(4-benzoylamino-1-butyl)-1,5-pentanedioic acid 1-(L-leucine, N-methylamide)amide;

2(R)-(2-(4-(1-n-Propyl)phenyl)ethyl)-4-(4-pivaloylamino-1-butyl)-1,5-pentanedioic acid 1-(L-leucine, N-methylamide)amide;

2(R)-(2-(4-(1-n-Propyl)phenyl)ethyl)-4-(4-phenylsulfonylamino-1-butyl)-1,5-pentandioic acid 1-(L-leucine, N-methylamide)amide;

2(R)-(2-(4-(1-n-Propyl)phenyl)ethyl)-4-(4-(N'-phenylureido)-1-butyl)-1,5-pentandioic acid 1-(L-leucine, N-methylamide)amide;

2(R)-(2-(4-(1-n-Propyl)phenyl)ethyl)-4-(4-phenyloxycarbonylamino-1-butyl)-1,5-pentandioic acid 1-(L-leucine, N-methylamide)amide;

2(R)-(2-(4-(1-n-Propyl)phenyl)ethyl)-4-(4-N'-benzyloxycarbonylamino-L-prolylamino)-1-butyl)-1,5-pentandioic acid 1-(L-leucine, N-methylamide)amide;

2(R)-(2-(4-(1-n-Propyl)phenyl)ethyl)-4-(4-cyclopentylamino-1-butyl)-1,5-pentandioic acid 1-(L-leucine, N-methylamide)amide;

2(R)-(2-(4-(1-n-Propyl)phenyl)ethyl)-4-(2-carboxybenzoylamino)-1-butyl)-1,5-pentandioic acid 1-(L-leucine, N-methylamide)amide;

2(R)-(2-(4-(1-n-Propyl)phenyl)ethyl)-4-(4-cyano-1-butyl)-1,5-pentandioic acid 1-(L-leucine, N-phenylamide)amide;

N-[1(R)-Carboxyethyl]-α-(S)-(9-amino-n-nonyl)]glycine-(L)-leucine, N-phenylamide;

N-[1(R)-Carboxyethyl]-α-(S)-(n-octyl)]glycine-(L)-leucine, N-phenylamide;

N-[1(R)-Carboxyethyl]-α-(S)-(n-octyl)]glycine-(L)-arginine, N-phenylamide;

N-[1(R)-Carboxyethyl]-α-(S)-(9-amino-n-nonyl)]glycine-(L)-arginine, N-phenylamide;

N-[1(R)-Carboxyethyl]-α-(S)-(n-decyl)]glycine-(L)-leucine, N-phenylamide;

1-(2-(4-Propylphenyl)ethyl)cyclopentane-1,3-dicarboxylic acid 1-(L-leucine, N-phenylamide)amide;

1-(2-(4-Propylphenyl)ethyl)cyclohexane-1,3-dicarboxylic acid 1-(L-leucine, N-phenylamide)amide;

N-[1(R)-Carboxyethyl]-α-(S)-2-(4-fluorobiphenyl)-glycyl-(S)-2-(tert-butyl)glycine, N-phenylamide;

3S-[4-(N-Hydroxyamino)-2R-isobutylsuccinyl]amino-1-methoxy-3,4-dihydrocarbostyril;

3S-[4-(N-Hydroxyamino)-2R-isobutyl-3S-acetylthiomethylsuccinyl]amino-3,4-dihydrocarbostyril;

3S-[4-(N-Hydroxyamino)-2R-isobutyl-3S-methylsuccinyl]amino-1-methoxy-3,4-dihydrocarbostyril;

3S-[4-(N-Hydroxyamino)-2R-isobutylsuccinyl]amino-1-methoxymethyl-3,4-dihydrocarbostyril;

1-Carboxymethyl-3S-[4-N-hydroxyamino-2R-isobutyl-3S-methylsuccinyl]amino-3,4-dihydrocarbostyril;

3S-[4-(N-Hydroxyamino)-2R-isobutylsuccinyl]amino-1-methoxyethoxymethyl-3,4-dihydrocarbostyril;

3S-[4-(N-Hydroxyamino)-2R-heptylsuccinyl]amino-1-methoxy-3,4-dihydrocarbostyril;

7-Chloro-3S-[4-(N-hydroxyamino)-2R-isobutyl-succinyl]amino-1-methoxymethyl-3,4-dihydrocarbostyril;

3S-[4-(N-Hydroxyamino)-2R-isobutylsuccinyl]amino-1-methoxyethyl-3,4-dihydrocarbostyril;

3S-[4-(N-Hydroxyamino)-2R-isobutylsuccinyl]-amino-1-methoxyethyl-6,7-methylenedioxy-3,4-dihydrocarbostyril;

3R-[4-(N-Hydroxyamino)-2R-isobutylsuccinyl]amino-1-methoxyethyl-6,7-methylenedioxy-3,4-dihydrocarbostyril;

2-(R)-N-Hydroxy-2-[(4-methoxybenzenesulfonyl)(3-morpholin-4-yl-3-oxopropyl)amino]-3-methylbutyramide;

2-(R)-2-[(2-Benzylcarbamoylethyl)(4-methoxybenzenesulfonyl)amino]-N-hydroxy-3-methylbutyramide;

2-(R)-N-Hydroxy-2-((4-methoxybenzenesulfonyl) (2-[(pyridin-3-ylmethyl)carbamoyl]ethyl)amino)-3-methylbutyramide;

2-(R)-N-Hydroxy-2-([4-methoxybenzenesulfonyl]-[2-(methylpyridin-3-ylmethylcarbamoyl)ethyl]amino)-3-methylbutyramide;

4-(3-[1-(R)-1-Hydroxycarbamoyl-2-methylpropyl)-(4-methoxybenzenesulfonyl)amino]propionyl)piperazine-1-carboxylic acid, tert-butyl ester;

2-(R)-N-Hydroxy-2-[(4-methoxybenzenesulfonyl)-(3-oxo-3-piperazin-1-ylpropyl)amino]-3-methylbutyramide hydrochloride;

2-(R)-2-[(Benzylcarbamoylethyl)(4-methoxybenzenesulfonyl)amino]-N-hydroxy-3-methylbutyramide;

2-(R)-N-Hydroxy-2-[(4-methoxybenzenesulfonyl)-[(2-morpholin-4-ylethylcarbamoyl)methyl]amino]-3-methylbutyramide;

2-(R)-N-Hydroxy-2-((4-methoxybenzenesulfonyl)([(pyridin-3-ylmethyl)carbamoyl]methyl)amino)-3-methylbutyramide;

2-(R)-3,3,3,-Trifluoro-N-hydroxy-2-[(methoxybenzenesulfonyl)(3-morpholin-4-yl-3-oxopropyl)amino]-propionamide;

2-(R)-N-Hydroxy-2-((4-phenoxybenzenesulfonyl)-[2-methylpyridin-4-ylmethylcarbamoyl)ether]amino)-3-methylbutyramide;

4-[4-Methoxybenzenesulfonyl)(3-morpholin-4-yl-3-oxopropyl)amino]-1-methylpiperidene-4-carboxylic acid hydroxyamide;

2-(R)-N-Hydroxy-2-((4-methoxybenzenesulfonyl)-[3-(4-methylpiperazin-1-yl)-3-oxopropyl]amino)-3-methylbutyramide;

2-(R)-2-[(2-Carboxyethyl)(4-methoxybenzenesulfonyl)amino]-N-hydroxy-3-methylbutyramide;

[(2-Carboxyethyl)(3,4-dimethoxybenzene-sulfonyl)-amino]-N-hydroxy-acetamide;

2-(R)-2-[(2-Carbamoylethyl)(4-methoxybenzenesulfonyl)amino]-N-hydroxy-3-methylbutyramide;

2-(R), 3-(R)-3, N-Dihydroxy-2-[(4-methoxybenzenesulfonyl)(3-oxo-3-piperidin-1-ylpropyl)amino]-butyramide;

2-(R)-N-Hydroxy-2-((4-methoxybenzenesulfonyl)-[3-(methylpyridin-3-ylmethylcarbamoyl)propyl]amino)-3-methylbutyramide;

2-(R)-N-Hydroxy-2-((4-methoxybenzenesulfonyl)-[2-(methylcarboxymethylcarbamoyl)ethyl]amino)-3-methylbutyramide;

2-(R)-N-Hydroxy-2-((4-methoxybenzenesulfonyl)-[(1-methylpiperidin-4-ylcarbamoyl)methyl]amino)-3-methylbutyramide;

2-(R)-N-Cyclohexyl-N-hydroxy-2-((4-methoxybenzenesulfonyl)-[3-(4-methylpiperazin-1-yl)-3-oxopropyl]amino)-acetamide;

2-(R)-N-Hydroxy-2-[(methoxybenzenesulfonyl)(3-morpholin-4-yl-[3-oxopropyl)amino]-4-(morpholin-4-yl)butyramide;

[4-N-Benzyloxyamino)-2(R)-isobutylsuccinyl]-L-leucyl-L-alanine ethyl ester;

[4-N-Benzyloxyamino)-2(R)-isobutylsuccinyl]-3(RS)-aminolaurolactam;

$N^a$-[4-(N-Benzyloxyamino)-2(R)-isobutylsuccinyl]-$N^e$-(N-benzyloxycarbonylglycyl)-L-lysyl-L-alanine ethyl ester;

[4-(N-Hydroxyamino)-2(RS)-isobutylsuccinyl]-L-leucylglycine ethyl ester;

[4-(N-Hydroxyamino)-2(RS)-isobutylsuccinyl]-L-leucylglycine isopentylamide;

[4-(N-Hydroxyamino)-2(RS)-isobutylsuccinyl]-L-valylglycine ethylamide;

[4-(N-Hydroxyamino)-2(RS)-isobutylsuccinyl]-L-leucylglycine ethylamide;

$N^a$-[4-(N-Hydroxyamino)-2(RS)-isobutylsuccinyl]-$N^e$-tert.butoxycarbonyl-L-lysylglycine ethylamide;

[4-(N-Hydroxyamino)-2(RS)-isobutylsuccinyl]-O-methyl-L-tyrosinylglycine ethyl ester;

[4-(N-Hydroxyamino)-2(RS)-isobutylsuccinyl]-O-methyl-L-tyrosinylglycine ethylamide;

[4-(N-Hydroxyamino)-2(RS)-isobutylsuccinyl]-L-leucyl-L-alanine ethyl ester;

[4-(N-Hydroxyamino)-2(RS)-isobutylsuccinyl]-L-leucylglycine isopentyl ester;

[4-(N-Hydroxyamino)-2(R)-propylsuccinyl]-L-leucylglycine ethyl ester;

[4-(N-Hydroxyamino)-2(RS)-sec.butylsuccinyl]-L-leucylglycine ethyl ester;

[4-(N-Hydroxyamino)-2(R)-isobutylsuccinyl]-L-leucyl-L-alanine;

[4-(N-Hydroxyamino)-2(RS)-isobutylsuccinyl]-L-leucylglycine methyl ester;

[4-(N-Hydroxyamino)-2(RS)-isobutylsuccinyl]-L-leucylsarconsine ethyl ester;

[4-(N-Hydroxyamino)-2(RS)-isobutylsuccinyl]-L-leucyl-L-proline ethyl ester;

[4-(N-Hydroxyamino)-2(RS)-isobutylsuccinyl]-L-leucine-L-alanine isopropyl ester;

[4-(N-Hydroxyamino)-2(RS)-isobutylsuccinyl]-L-leucine-2-oxopropylamide;

[4-(N-Hydroxyamino)-2(RS)-isobutylsuccinyl]-L-leucine-2-methoxyethylamide;

[4-(N-Hydroxyamino)-2(RS)-isobutylsuccinyl]-L-leucine-2,2-dimethoxyethylamide;

$N^a$-[4-(N-Hydroxyamino)-2(R)-isobutylsuccinyl]-$N^e$-glycyl-L-lysine methylamide;

$N^a$-[4-(N-Hydroxyamino)-2(R)-isobutylsuccinyl]-$N^e$-(4-carboxybenzoyl)-L-lysl-L-alanine ethyl ester;

$N^a$-[4-(N-Hydroxyamino)-2(R)-isobutylsuccinyl]-$N^e$-(4-carboxybenzoyl)-L-lysyl-L-aline;

[4-(N-Hydroxyamino)-2(R)-isobutylsuccinyl]-3(RS)-aminooctahydro-2H-azonin-2-one;

[4-(N-Hydroxyamino)-3(S)-methyl-2(R)-isobutyl-succinyl]-L-leucylglycine ethyl ester;

[(3-Aminophthalimido)methyl][(RS)-4-methyl-2-[[(S)3-methyl-1-(methylcarbamoyl)butyl]carbamoyl]pentyl] phosphinic acid;

[(RS)-4-Methyl-2-[[(S)-3-methyl-1-(methyl-carbamoyl)butyl]carbamoyl]pentyl](1,8-naphthalenedicarboximidomethyl)phosphinic acid;

[(R or S)-4-Methyl-2-[[(R or S)-2-oxo-3-azacyclotridecyl]carbamoyl]pentyl](1.8-naphthalenedicarboximidomethyl)phosphinic acid;

N-[N-[(R or S)-2[[[[N-[1-(Benzyloxy)carbonyl]-L-prolyl]-L-leucyl]amino]methyl]hydroxyphosphinyl]-methyl]-4-methylvaleryl]-L-leucyl]-L-alanine;

[[1,4-Dihydro-2,4-dioxo-3(2H)-quinazolinyl]-methyl][[(R or S)-4-methyl-2-[[(R or S)-2-oxo-3-azacyclotridecyl]carbamoyl]pentyl]phosphinic acid;

$N^2$-[(R)-Hydroxycarbamoylmethyl]-4-methylvaleryl]-$N^1$,3-dimethyl-L-valinamide;

$N^2$-[2(R or S)-[[[(5-Bromo-2,3-dihydro-6-hydroxy)-1,3-dioxo-1H-benz[d,e]isoquinol-2-yl)methyl]-[(hydroxy)phosphinyl]methyl]-4-methylvaleryl]-$N^1$, 3-dimethyl-L-valinamide;

$N^2$-[(R or S)-[[(R)-(Amino)[(5-bromo-2,3-dihydro-6-hydroxy-1,3-dioxo-1H-benz[d,e]isoquinol-2-yl)methyl]-(hydroxy)phosphinyl]methyl]-4-methylvaleryl]-$N^3$,1-dimethyl-L-valinamide hydrobromide;

$N^2$-([2(R or S)-[1(S)-(Hydroxycarbamoyl)ethyl-4-methylvaleryl]-$N^1$,3-dimethylvalinamide;

$N^2$-[2(R)-[1(R or S)-(Hydroxycarbamoyl)-2-phthalimidoethyl]-4-methylvaleryl]-$N^1$,3-dimethyl-L-valinamide;

$N^2$-[2(R)-[1(R or S)-(Hydroxycarbamoyl)-4-(methoxy-carbonyl)butyl]-4-methylvaleryl]-$N^1$,3-dimethyl-L-valinamide;

$M^2$-[2(R)-[1(R or S)-(Hydroxycarbamoyl)-4-phenyl-butyl]-4-methylvaleryl]-$N^1$,3-dimethyl-L-valinamide;

N²-[2(R)-[1(R or S)-(Hydroxycarbamoyl)-2-succinimidoethyl]-4-methylvaleryl]-N¹,3-dimethyl-L-valinamide;

4-[2(R)-[1(R or S)-(Hydroxycarbamoyl)-2-phthalimidoethyl]-4-methylvaleryl]morpholine;

4-[2(R)-[1(R or S)-(Hydroxycarbamoyl)-2-phthalimidoethyl]-4-methylvaleryl]tetrahydro-1,4-thiazine;

1-[2(R)-[1(R or S)-(Hydroxycarbamoyl)-2-phthalimidoethyl]-4-methylvaleryl]-4-piperidinol;

1-[2(R)-[1(R or S)-(Hydroxycarbamoyl)-2-(1,2-dimethyl-3,5-dioxo-1,2,4-triazolidin-4-yl)ethyl]-4-methylvaleryl]piperidine;

4-[2(R)-[1(R or S)-(Hydroxycarbamoyl)-2-(3-methyl-2,5-dioxo-1-imidazolidinyl)ethyl]-4-methylvaleryl]tetrahydro-1,4-thiazine;

Hexahydro-2-[2(R)-[1(R or S)-(hydroxycarbamoyl)-2-phthalimidoethyl]-4-methylvaleryl]-N-methyl-3(S)-pyridazinecarboxamide;

1-[2(R)-(R or S)-(Hydroxycarbamoyl)-2-(3,4,4-trimethyl-2,5-dioxo-1-imidazolidinyl)ethyl]-4-methylvaleryl]-4-piperidinol;

[4-(N-Hydroxyamino)-2(R or S)-heptylsuccinyl]-L-leucyl-L-leucine ethylamide;

[4-(N-Hydroxyamino)-2(R or S)-nonylsuccinyl]-L-leucyl-L-leucine ethylamide;

[4-(N-Hydroxyamino)-2(R or S)-heptyl-3(S)-methylsuccinyl]-L-leucyl-L-leucine ethylamide;

[4-(N-Hydroxyamino)-2(R)-heptyl-3(R or S)-(phthalimidomethyl)succinyl]-L-leucyl-L-leucine ethylamide;

[4-(N-Hydroxyamino)-2(RS)-nonylsuccinyl]-L-tert.butylglycine methylamide;

[4-(N-Hydroxyamino)-2(RS)-heptylsuccinyl]-L-phenylalanine methylamide;

[4-(N-Hydroxyamino)-2(R)-heptyl-3(R or S)-phthalimidomethyl)succinyl]-L-tert.butylglycine methylamide;

[4-(N-Hydroxyamino)-2(R)-heptyl-3(R or S)-(3-phenylpropyl)-succinyl]-L-leucyl-L-leucine ethylamide;

[4-(N-Hydroxyamino)-2(RS)-heptylsuccinyl]-L-leucine methylamide;

[4-(N-Hydroxyamino)-2(RS)-heptylsuccinyl]-L-leucine neopentylamide;

[4-(N-Hydroxyamino)-2(RS)-heptylsuccinyl]-L-alanyl-L-leucine ethylamide;

[4-(N-Hydroxyamino)-2(RS)-heptylsuccinyl]-L-(Nᵉ-phthaloyl)-lysyl-L-leucine ethylamide;

[4-(N-Hydroxyamino)-2(RS)-undecylsuccinyl]-L-leucyl-L-leucine ethylamide;

[4-(N-Hydroxyamino)-2(RS)-heptylsuccinyl]-L-phenylalanyl-L-leucine ethylamide;

[4-(N-Hydroxyamino)-2(RS)-heptylsuccinyl]-L-nonalyl-L-leucine ethylamide;

[4-(N-Hydroxyamino)-2(RS)-heptylsuccinyl]-phenylalanine tert.butylamide;

[4-(N-Hydroxyamino)-2(RS)-heptylsuccinyl]-L-tertbutylglycine methylamide;

[4-(N-Hydroxyamino)-2(RS)-heptylsuccinyl]-L-neopentylglycine methylamide;

[4-(N-Hydroxyamino)-2(RS)-heptylsuccinyl]-L-homophenylalanyl-L-leucine ethylamide;

[4-(N-Hydroxyamino)-2(RS)-heptylsuccinyl]-L-cyclohexylalanine methylamide;

[4-(N-Hydroxyamino)-2(RS)-isooctylsuccinyl]-L-phenylalanine methylamide;

[4-(N-Hydroxyamino)-2(R)-heptylsuccinyl]-L-neonpentylglycine methylamide;

[4-(N-Hydroxyamino)-2(R)-heptylsuccinyl]-(D or L)-β,β-dimethylphenylalanine methylamide;

[4-(N-Hydroxyamino)-2(R)-heptylsuccinyl]-(D or L)-threo-β-methylphenylalanine methylamide;

[4-(N-Hydroxyamino)-2(R)-heptylsuccinyl]-DL-erthro-β-methylphenylalanine methylamide;

[4-(N-Hydroxyamino)-2(R)-heptyl-3(R or S)-[(3-methyl-2,5-dioxo-1-imidazolidinyl)methyl]succinyl]-L-leucyl-L-leucine ethylamide;

N2-[3-Cyclobutyl-2(R or S)-[(hydroxycarbamoyl)-methyl]-propionyl]-N1,3-dimethyl-L-valinamide;

N2-[3-Cyclopropyl-2(R or S)-[(hydroxycarbamoyl)-methyl]-propionyl]-N1,3-dimethyl-L-valinamide;

N2-[3-Cyclopentyl-2(R or S)-[(hydroxycarbamoyl)-methyl]-propionyl]-N1,3-dimethyl-L-valinamide;

N2-[3-Cyclopropyl-2(R)-[1(R or S)-[(hydroxycarbamoyl)-2-(3,4,4-trimethyl-2,5-dioxo-1-imidazolidinyl)ethyl]propionyl]-N1,3-dimethyl-L-valinamide;

N2-[3-Cyclopropyl-2(R)-[1(R or S)-[(hydroxycarbamoyl)-4-phenylbutyl)]propionyl]-N1,3-dimethyl-L-valinamide;

N2-[3-Cyclobutyl-2(R)-[1(R or S)-(hydroxycarbamoyl)-4-phenylbutyl]propionyl]-N1,3-dimethyl-L-valinamide;

N2-[3-Cyclopentyl-2(R)-[1(R or S)-(hydroxycarbamoyl)-4-phenylbutyl]propionyl]-N1,3-dimethyl-L-valinamide;

1-[3-Cyclopropyl-2(R)-[1(R or S)-(hydroxycarbamoyl)-2-(3,4,4-trimethyl-2,5-dioxo-1-imidazolidinyl)ethyl]propionyl]piperidine;

1-[3-Cyclopropyl-2(R)-[1(R or S)-(hydroxycarbamoyl)-2-(3,4,4-trimethyl-2,5-dioxo-1-imidazolidinyl)ethyl]propionyl]-4-piperidinol;

1-[3-Cyclobutyl-2(R)-[1(R or S)-(hydroxycarbamoyl)-2-(3,4,4-trimethyl-2,5-dioxo-1-imidazolidinyl)ethyl]propionyl]piperidine;

1-[3-Cyclobutyl-2(R)-[1(R or S)-(hydroxycarbamoyl)-2-(3,4,4-trimethyl-2,5-dioxo-1-imidazolidinyl)ethyl]propionyl]-4-piperidinol;

1-[3-Cyclopentyl-2(R)-[1(R or S)-(hydroxycarbamoyl)-2-(3,4,4-trimethyl-2,5-dioxo-1-imidazolidinyl)ethyl]propionyl]-4-piperidinol;

1-[3-Cyclopentyl-2(R)-(1(R or S)-(hydroxycarbamoyl)-2-(3,4,4-trimethyl-2,5-dioxo-1-imidazolidinyl)ethyl]propionyl]piperidine;

3-[3-Cyclobutyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]-nonane;

3-[3-Cyclopropyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]-nonane;

3-[3-Cyclopentyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]-nonane;

1-[3-Cyclohexyl-2(R)-[1(R or S)-(hydroxycarbamoyl)-2-(3,4,4-trimethyl-2,5-dioxo-1-imidazolidinyl)ethyl]propionyl]piperidine;

4-[3-Cyclopentyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine;

4-[3-Cyclopentyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine S,S-dioxide;

4-[3-Cyclobutyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine;

3-[3-Cyclopentyl-2(R)-[1(R or S)-(hydroxycarbamoyl)-2-(3,4,4-trimethyl-2,5-dioxo-1-imidazolidinyl)ethyl]

propionyl]-5,5-dimethyl-N-propyl-[4(R)-thiazolidinecarboxamide;

4-[3-Cyclopentyl-2(R)-[1(R or S)-(hydroxycarbamoyl)-2-(3,4,4-trimethyl-2,5-dioxo-1-imidazolidinyl)ethyl]propionyl]morpholine;

3-[3-Cyclopentyl-2(R)-[1(R or S)-(hydroxycarbamoyl)-2-(3,4,4-trimethyl-2,5-dioxo-1-imidazolidinyl)ethyl]propionyl]-N,5,5-trimethyl-4(R)-thiazolidinecarboxamide;

4-[3-Cyclobutyl-2(R)-[1(R or S)-(hydroxycarbamoyl)-2-(3,4,4-trimethyl-2,5-dioxo-1-imidazolidinyl)ethyl]propionyl]-4-phenylpiperazine;

4-[3-Cyclobutyl-2(R)-[1(R or S)-(hydroxycarbamoyl)-2-(3,4,4-trimethyl-2,5-dioxo-1-imidazolidinyl)ethyl]propionyl]morpholine;

1-[3-Cyclobutyl-2(R)-[1(R or S)-(hydroxycarbamoyl)-2-(3,4,4-trimethyl-2,5-dioxo-1-imidazolidinyl)ethyl]propionyl]pyrrolidine;

8-[3-Cyclobutyl-2(R)-[1(R or S)-(hydroxycarbamoyl)-2-(3,4,4-trimethyl-2,5-dioxo-1-imidazolidinyl)ethyl]propionyl]-1,4-dioxa-8-azaspiro[4,5]decane;

1-[3-Cyclobutyl-2(R)-[1(R or S)-(hydroxycarbamoyl)-2-(3,4,4-trimethyl-2,5-dioxo-1-imidazolidinyl)ethyl]propionyl]-4-methoxypiperidine;

1-[3-Cyclobutyl-2(R)-[1(R or S)-(hydroxycarbamoyl)-2-(3,4,4-trimethyl-2,5-dioxo-1-imidazolidinyl)ethyl]propionyl]octahydroazocine;

1-[3-Cyclobutyl-2(R)-[1(R or S)-(hydroxycarbamoyl)-2-(5,5-dimethyl-2,4-dioxo-3-oxazolidinyl)ethyl]propionyl]piperidine;

1-[3-Cyclobutyl-2(R)-[1(R or S)-(hydroxycarbamoyl)-2-(3,4,4-trimethyl-2,5-dioxo-1-imidazolidinyl)ethyl]propionyl]hexahydroazepine;

1-[3-Cyclobutyl-2(R)-[2-(hexahydro-1,3-dioxo-pyrazolo[1,2-a][1,2,4]triazol-2-yl)-1(R or S)-(hydroxycarbamoyl)ethyl]propionyl]piperidine;

1-[3-Cyclobutyl-2(R)-[1(R or S)-(hydroxycarbamoyl)-2-phthalimidoethyl]propionyl]piperidine;

2-[2(R)-[1(R or S)-(Hydroxycarbamoyl)-4-phenylbutyl]nonanoyl]hexahydro-N-methyl-3(S)-pyridazinecarboxamide;

N-Cyclohexyl-hexahydro-2-[2(R)-[1(RS)-(hydroxycarbamoyl)-4-phenylbutyl]nonanoyl]-3(S)-pyridazinecarboxamide;

Hexahydro-2-[2(R)-[1(RS)-(hydroxycarbamoyl)-4-phenylbutyl]nonanoyl]-N-(2,2,6,6-tetramethyl-4-piperidinyl)-3(S)-pyridazinecarboxamide;

1-[2(R)-[1(R or S)-Hydroxycarbamoyl)-4-phenylbutyl]nonanoyl]piperidine;

N2-[2(R)-[1(RS)-(Hydroxycarbamoyl)-2-(3,4,4-trimethyl-2,5-dioxo-1-imidazolidinyl)ethyl]nonanoyl]-N1-methyl-L-prolinamide;

1-[2(R)-[1(R or S)-(Hydroxycarbamoyl)-2-(3,4,4-trimethyl-2,5-dioxo-1-imidazolidinyl)ethyl]nonanoyl]-piperidine;

Hexahydro-2-[2(R)-1(R or S)-(hydroxycarbamoyl)-2-(3,4,4-trimethyl-2,5-dioxo-1-imidazolidinyl)ethyl]-nonanoyl]-N-methyl-3(S)-pyridazinecarboxamide;

Hexahydro-2-[2(R or S)-[1(S)-(hydroxycarbamoyl)-3-phenylpropyl]undecanoyl]-N-methyl-3(S)-pyridazinecarboxamide;

Hexahydro-2-[2(R or S)-[1(S)-(hydroxycarbamoyl)-3-phenylpropyl]undecanoyl]-N-methoxy-N-methyl-3(S)-pyridazinecarboxamide;

Hexahydro-2-[2(R or S)-[(1(S)-(hydroxycarbamoyl)-3-phenylpropyl]undecanoyl]-N-(1,2,2,6,6-pentamethyl-4-piperidinyl)-3(S)-pyridazinecarboxamide;

Hexahydro-2-[2(R or S)-[1(S)-(hydroxycarbamoyl)-ethyl]undecanoyl]-N-methyl-3(S)-pyridazinecarboxamide;

Hexahydro-2-[2(R or S)-[1(S)-(hydroxycarbamoyl)-3-phenylpropyl]nonanoyl]-N-methyl-3(S)-pyridazinecarboxamide;

Hexahydro-2-[2(R or S)-[1(S)-(hydroxycarbamoyl)-ethyl]nonanoyl]-N-methyl-3(S)-pyridazinecarboxamide;

1-[2(R or S)-[1(S)-(Hydroxycarbamoyl)ethyl]undecanoyl]piperidine;

1-[2-(R or S)-[1(S)-(hydroxycarbamoyl)-3-phenylpropyl]undecanoyl]piperidine;

Hexahydro-2-[2(R or S)-[1(S)-(hydroxycarbamoyl)-3-phenylpropyl]undecanoyl]-N-(2,2,6,6-tetramethyl-4-piperidinyl)-3(S)-pyridazinecarboxamide;

Hexahydro-2-[2(R or S)-[1(S)-(hydroxycarbamoyl)-ethyl]undecanoyl]-N(2,2,6,6-tetramethyl-4-piperidinyl)-3(S)-pyridazinecarboxamide;

1-[2(R or S)-[1(S)-(hydroxycarbamoyl)-4-phenylbutyl]undecanoyl]-piperidine;

4-[2(R or S)-[1(S)-(hydroxycarbamoyl)-4-phenylbutyl]undecanoyl]morpholine;

1-(Benzyloxycarbonyl)-hexahydro-2-[2(R)-[(R or S)-(hydroxycarbamoyl)-4-phenylbutyl]nonanoyl]-N-(α(S)-methylbenzyl)-3(S)-pyridazinecarboxamide;

N-[(2R)-2-[2'-(Hydroxyamino)-2'-(oxo)ethyl]-5-(carboxy)pentanoyl]-L-phenylalanine N-methylamide;

N-[(2R)-2-[2'-(Hydroxyamino)-2'-(oxo)ethyl]-6-(phenylmethoxy)hexanoyl]-L-phenylalanine N-methylamide;

N-[(2R)-2-[2'-(Hydroxyamino)-2'-(oxo)ethyl]-6-(propylamino)-6-(oxo)hexanoyl]-L-phenylalanine N-methylamide;

N-[(2R)-2-[2'-(Hydroxyamino)-2'-(oxo)ethyl]-(6RS)-6-(hydroxy)heptanoyl]-L-phenylalanine N-methylamide;

(2S)-N-2-[(2'R)-2'-[2''-(Hydroxyamino)-2''-(oxo)ethyl]-6'-(hydroxy)hexanoyl]amino-3,3-dimethylbutanoic acid N-methylamide;

(2S)-N-2-[(2'R)-2'-[2''-(Hydroxyamino)-2''-(oxo)ethyl]-6'-(phenylmethoxy)hexanoyl]amino-3,3-dimethylbutanoic acid N-methylamide;

N-[(2'R)-2-[2'-(Hydroxyamino)-2'-(oxo)ethyl]-6-(4'oxobutylamino)hexanoyl]-L-phenylalanine N-methylamide;

2(S)-N-2-[(2'R)-2'-[2''-(Hydroxyamino)-2''-(oxo)ethyl]-6'-(oxo)-6'-(propylamino)hexanoyl]amino-3,3-dimethylbutanoic acid N-methylamide;

N-[(2R)-2-[(1'S)-1'-(Methyl)-2'-(hydroxyamino)-2'-(oxo)ethyl]-6-(phenylmethoxy)hexanoyl]-L-phenylalanine N-methylamide;

N-[(2R)-2-[(1'S)-1'-(Methyl)-2'-(hydroxyamino)-2'-(oxo)ethyl]-6-(oxo)-6-(propylamino)hexanoyl]-L-phenylalanine N-methylamide;

(2S)-N-2[(2'R)-[(1''R)-1''-(1,3-Dihydro-1,3-dioxo-2H-isoindol-2-yl)methyl-2''-(hydroxyamino)-2''-(oxo)ethyl]-6'-(phenylmethoxy)hexanoyl]amino-3,3-dimethylbutanoic acid N-methylamide;

N-[(2R)-2-[2'-(Hydroxyamino)-2'-(oxo)ethyl]-6-(oxo)-6-(propylamino)hexanoyl]-L-phenylalanine N-2-phenylethylamide;

(2S)-N-2-[(2'R)-2'-[(1''S)-1''-(Methyl)-2''-(hydroxyamino)-2''-(oxo)ethyl]-6-(phenylmethoxy)-hexanoyl]amino-3,3-dimethylbutanoic acid N-2-phenylethylamide;

(2S)-N-2-[(2'R)-2'-[(1''S)-1''-(Methyl)-2''-(hyroxyamino)-2''-(oxo)ethyl]-6'-(oxo)-6'-(propylamino)-hexanoyl]amino-3,3-dimethylbutanoic acid N-2-phenylethylamide;

(2S)-N-2-[(2'R)-2'-[(1''S)-1''-(Methyl)-2''-(hydroxyamino)-2''-(oxo)ethyl]-6'-(oxo)-6'-(propylamino)

hexanoyl]amino-3,3-dimethylbutanoic acid N-2-(4'-sulfamoyl)phenylethylamide;

(2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

N-[2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

(2S)-N-2'-[(2'R)-2'-[2"-(Hydroxyamino)-2"-(oxo)ethyl]-6'-[(4-methoxy)phenoxy]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(4-methyl)phenoxy]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(1-oxo)butylamino]hexanoyl]amino-3-cyclohexylpropionic acid N-2-(4'-sulfamoyl)phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-methylamide;

(2S)-N-2-[(2'R)-2'-[(1"S)-1"-(2-Methylpropyl)-2"-(hydroxyamino)-2"-(oxo)ethyl]-6-(phenylmethoxy)hexanoyl]amino-3,3-dimethylbutanoic acid N-methylamide;

N-[(2R)-2-[2'-(Hydroxyamino)-2'-(oxo)ethyl]-6-(phenoxy)hexanoyl]-L-phenylalanine N-methylamide;

N-[(2R)-2-[2'-(Hydroxyamino)-2'-(oxo)ethyl]-7-(phenoxy)heptanoyl]-L-phenylalanine N-methylamide;

(2S)-N-2'-[(2'R)-2'-[2"-(Hydroxyamino)-2"-(oxo) ethyl]-6'-(phenylmethoxy)hexanoyl]amino-3,3-dimethylbutanoic acid N-2-phenylethylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-(4'-sulfamoyl)phenylethylamide;

N-[(2R)-2-[2'-(Hydroxyamino)-2'-(oxo)ethyl]-5-(phenylmethoxy)pentanoyl]-L-phenylalanine N-methylamide;

N-[(2R)-2-[2'-(Hydroxyamino)-2'-(oxo)ethyl]-7-(phenylmethoxy)heptanoyl]-L-phenylalanine N-methylamide;

N-[(2R)-2-[2'-(Hydroxyamino)-2'-(oxo)ethyl]-6-(phenyloxy)hexanoyl]-L-phenylalanine N-methylamide;

N-[(2R)-2-[2'-(Hydroxyamino)-2'-(oxo)ethyl]-7-[(phenyloxy)heptanoyl]-L-phenylalanine N-methylamide;

(2S)-N-2'-[(2'R)-2'-[2"-(Hydroxyamino)-2"-(oxo)ethyl]-6'-[(2-phenethylamino)-6'-(oxo)hexanoyl]-amino-3,3-dimethylbutanoic acid N-methylamide;

(2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(3-methylphenoxy)hexanoyl]amino-3,3-dimethylbutanoic acid N-methylamide;

(2S)-N-2'-[(2'R)-2'-(carboxymethyl)-6'-(3-methylphenoxy)hexanoyl]amino-3,3-dimethylbutanoic acid N-methylamide;

N-[(2R)-2-[2'-(Hydroxyamino)-2'-(oxo)ethyl]-5-(carboxy)pentanoyl]-L-phenylalanine N-methylamide;

N-[(2R)-2-[2'-(Hydroxyamino)-2'-(oxo)ethyl]-6-(phenylmethoxy)hexanoyl]-L-phenylalanine N-methylamide;

N-[(2R)-2-[2'-(Hydroxyamino)-2'-(oxo)ethyl]-6-(propylamino)-6-(oxo)hexanoyl]-L-phenylalanine N-methylamide;

N-[(2R)-2-[2'-(Hydroxyamino)-2'-(oxo)ethyl]-(6RS)-6-(hydroxy)heptanoyl]-L-phenylalanine N-methylamide;

(2S)-N-2-[(2'R)-2'-[2"-(Hydroxyamino)-2"-(oxo)ethyl]-6'-(hydroxy)hexanoyl]amino-3,3-dimethylbutanoic acid N-methylamide;

(2S)-N-2-[(2'R)-2'-[2"-(Hydroxyamino)-2"-(oxo)ethyl]-6'-(phenylmethoxy)hexanoyl]amino-3,3-dimethylbutanoic acid N-methylamide;

N-[(2'R)-2-[2'-(Hydroxyamino)-2'-(oxo)ethyl]-6-(4'-oxobutylamino)hexanoyl]-L-phenylalanine N-methylamide;

2(S)-N-2-[(2'R)-2'-[2"-(Hydroxyamino)-2"-(oxo)ethyl]-6'-(oxo)-6'-(propylamino)hexanoyl]amino-3,3-dimethylbutanoic acid N-methylamide;

N-[(2R)-2-[(1'S)-1'-(Methyl)-2'-(hydroxyamino)-2'-(oxo)ethyl]-6-(phenylmethoxy)hexanoyl]-L-phenylalanine N-methylamide;

N-[(2R)-2-[(1'S)-1'-(Methyl)-2'-(hydroxyamino)-2'-(oxo)ethyl]-6-(oxo)-6-(propylamino)hexanoyl]-L-phenylalanine N-methylamide;

(2S)-N-2[(2'R)-[(1"R)-1"-(1,3-dihydro-1,3-dioxo-2H-isoindol-2-yl)methyl-2"-(hydroxyamino)-2"-(oxo)ethyl]-6'-(phenylmethoxy)hexanoyl]amino-3,3-dimethylbutanoic acid N-methylamide;

N-[(2R)-2-(2'-(Hydroxyamino)-2'-(oxo)ethyl]-6-(oxo)-6-(propylamino)hexanoyl]-L-phenylalanine N-2-phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl]amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl]amino-3,3-dimethylbutanoic acid N-2-(4'-sulfamoyl)phenylethylamide;

(2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

N-[(2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

(2S)-N-2'-[(2'R)-2'-[2"-(Hydroxyamino)-2"-(oxo)ethyl]-6'-[(4-methoxy)phenoxy]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(4-methyl)phenoxy]hexanoyl]amino-3,3-dimethylbutanoic acid N-2-(4'-sulfamoyl)phenylethylamide;

(2S) -N-2-[(2'R)-2'-[2"-(Hydroxyamino)-2"-(oxo)ethyl]-6'-[(1-oxo)butylamino]hexanoyl]amino-3-cyclohexylpropionic acid N-2-(4'-sulfamoyl)phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-methylamide;

(2S)-N-2-[(2'R)-2'-[(1"S)-1"-(2-Methylpropyl)-2"-(hydroxyamino)-2"-(oxo)ethyl]-6-(phenylmethoxy)hexanoyl]amino-3,3-dimethylbutanoic acid N-methylamide;

N-[(2R)-2-[2'-(Hydroxyamino)-2'-(oxo)ethyl]-6-(phenoxy)hexanoyl]-L-phenylalanine N-methylamide;

N-[(2R)-2-[2'-(Hydroxyamino)-2'-(oxo)ethyl]-7-(phenoxy)heptanoyl]-L-phenylalanine N-methylamide;

(2S)-N-2'-[(2'R)-2-[2"-(Hydroxyamino)-2"-(oxo)ethyl]-6'-(phenylmethoxy)hexanoyl]amino-3,3-dimethylbutanoic acid N-2-phenylethylamide;

(2S)-N-2'-[(2'R)-2'-[2'-(Hydroxyamino)-2"-(oxo)ethyl]-6-(phenylmethoxy)hexanoyl]amino-3,3-dimethylbutanoic acid N-2-(4'-sulfamoyl)phenylethylamide;

N-[(2R)-2-[2'-(Hydroxyamino)-2'-(oxo)ethyl]-5-(phenylmethoxy)pentanoyl]-L-phenylalanine N-methylamide;

N-[(2R)-2-[2'-(Hydroxyamino)-2'-(oxo)ethyl]-7-(phenylmethoxy)heptanoyl]-L-phenylalanine N-methylamide;

N-[(2R)-2-[2'-(Hydroxyamino)-2'-(oxo)ethyl]-6-(phenyloxy)hexanoyl]-L-phenylelanine N-methylamide;

N-[(2R)-2-[2'-(Hydroxyamino)-2'-(oxo)ethyl]-7-[(phenyloxy)heptanoyl]-L-phenylalanine N-methylamide;

(2S)-N-2-[(2'R)-2'-[2"-(Hydroxyamino)-2"-(oxo)ethyl]-6'-[(2-phenethylamino)-6'-(oxo)hexanoyl]-amino-3,3-dimethylbutanoic acid N-methylamide;

(2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(3-methylphenoxy)hexanoyl]amino-3,3-dimethylbutanoic acid N-methylamide;

(2S)-N-2'-[(2'R)-2'-(Carboxymethyl)-6'-(3-methylphenoxy)hexanoyl]amino-3,3-dimethylbutanoic acid N-methylamide;

(3R,10S)-5-Methyl-3-(9-oxo-1,8-diazatricyclo-[10.6.1.0]nonadeca-12(19),13(18),14,16-tetraen-10-ylcarbamoyl)hexanoic acid;

(3R,10S)-N-Hydroxy-5-methyl-3-(9-oxo-1,8-diazatricyclo[10.6.1.0]nonadeca-12(19),13(18),14,16-tetraen-10-ylcarbamoyl)hexanamide;

(3R,11S)-N-Hydroxy-5-methyl-3-(10-oxo-1,9-diazatricyclo[11.6.1.0]eicosa-13(20),14(19),15,17-tetraen-11-ylcarbamoyl)hexanamide;

(3R,9S)-5-Methyl-3-(8-oxo-1,7-diazatricyclo-[9.6.1.0]octadeca-11(18),12(17),13,15-tetraen-9-ylcarbamoyl)hexanoic acid;

(3R,9S)-N-Hydroxy-5-methyl-3-(8-oxo-1,7-diazatricyclo[9.6.1.0]octadeca-11(18),12(17),13,15-tetraen-9-ylcarbamoyl)hexanamide;

(10S)-[4-Methyl-2-(9-oxo-1,8-diazatricyclo-[10.6.1.0]nonadeca-12(19),13(18),14,16-tetraen-10-ylcarbamoyl)pentyl]-(quinolin-2-ylthiomethyl)phosphinic acid;

(3R,10S)-N-Hydroxy-5-methyl-2-methoxycarbonyl-3-(9-oxo-1,8-diazatricyclo[10.6.1.0]nonadeca-12(19), 13(18),14,16-tetraen-10-ylcarbamoyl)hexanamide;

N-(4-Methyl-2-carboxymethylpentanoyl)-L-leucine-N'-(4-methoxycarbonylphenyl)carboxamide;

N-(4-Methyl-2-(N"-hydroxycarbamoyl)methyl-pentanoyl)-L-leucine-N'-(4-methoxycarbonylphenyl)carboxamide;

N-(4-Methyl-2-(N"-hydroxycarbamoyl)methyl-pentanoyl)-L-leucine-N'-(4-carboxyphenyl)carboxamide;

N-(4-Methyl-2-(N"-hydroxycarbamoyl)methyl-pentanoyl)-L-tryptophan-N'-(4-carboxyphenyl)carboxamide;

N-(4-Methyl-2-(N"-hydroxycarbamoyl)methyl-pentanoyl)-L-cyclohexylglycine-N'-(4-methoxycarbonylphenyl)carboxamide;

N-(4-Methyl-2-(N"-hydroxycarbamoyl)methyl-pentanoyl)-L-t-leucine-N'-(4-methoxycarbonylphenyl)carboxamide;

(3R,10S)-6-Biphenyl-4-yl)-3-(9-oxo-1,8-diazatricyclo[10.6.1.0]onadeca-12(19),13(18),14,16-tetraen-10-ylcarbamoyl)hexanoic acid;

(3R,10S)-3-(9-Oxo-1,8-diazatricyclo[10.6.1.0]-nonadeca-12(19),13(18),14,16-tetraen-10-ylcarbamoyl)-5-(thiophen-2-yl)pentanoic acid;

(3R,10S)-3-Cyclopentyl-3-(9-oxo-1,8-diazatricyclo[10.6.1.0]nonadeca-12(19),13(18),14,16-tetraen-10-ylcarbamoyl)propionic acid;

(3R,10S)-4-Cyclopentyl-3-(9-oxo-1,8-diazatricyclo[10.6.1.0]nonadeca-12(19),13(18),14,16-tetraen-10-ylcarbamoyl)butanoic acid;

(3R,10S)-4-Cyclopropyl-3-(9-oxo-1,8-diazatricyclo[10.6.1.0]nonadeca-12(19),13(18),14,16-tetraen-10-ylcarbamoyl)butanoic acid;

(3R,10S)-5-Methyl-3-(9-oxo-1,8-diazatricyclo-[10.6.1.0]nonadeca-12(19),13(18),14,16-tetraen-10-ylcarbamoyl)hexanoic acid;

(3R,10S)-N-Hydroxy-5-methyl-3-(9-oxo-1,8-diazatricyclo[10.6.1.0]nonadeca-12(19),13(18),14,16-tetraen-10-ylcarbamoyl)hexanamide;

(3R,11S)-N-Hydroxy-5-methyl-3-(10-oxo-1,9-diazatricyclo[11.6.1.0]eicosa-13(20),14(19),15,17-tetraen-11-ylcarbamoyl)hexanamide;

(3R,9S) -N-5-Methyl-3-(8-oxo-1,7-diazatricyclo-[9.6.1.0]octadeca-11(18),12(17),13,15-tetraen-9-ylcarbamoyl)hexanoic acid;

(3R,9S)-N-Hydroxy-5-methyl-3-(8-oxo-1,7-diazatricyclo[9.6.1.0]octadeca-11(18),12(17),13,15-tetraen-9-ylcarbamoyl)hexanamide;

(10S)-2-Mercaptomethyl-4-methyl-N-(9-oxo-1,8-diazatricyclo[10.6.1.0]nonadeca-12(19),13(18),14,16-tetraen-10-ylcarbamoyl)pentanamide;

(10S)-2-Acetylthiomethyl-4-methyl-N-(9-oxo-1,8-diazatricyclo[10.6.1.0]nonadeca-12(19),13(18);14,16-tetraen-10-ylcarbamoyl)pentanamide;

(3R,10S)-2-(Methanesulfonamidomethyl)-5-methyl-3-(9-oxo-1,8-diazatricyclo[10.6.1.0]nonadeca-12(19),13(18),14,16-tetraen-10-ylcarbamoyl)hexanoic acid;

(3R,10S)-2-(3-Ethylureidomethyl)-5-methyl-3-(9-oxo-1, 8-diazatricyclo[10.6.1.0]nonadeca-12(19),13(18),14,16-tetraen-10-ylcarbamoyl)hexanoic acid;

(3R,9S)-N-Hydroxy-2-hydroxy-5-methyl-3-(8-oxo-1,7-diazatricyclo[9.6.1.0]octadeca-11(18),12(17),14,16-tetraen-9-ylcarbamoyl)hexanamide or its (2S,3R,9S) stereoisomer;

(3R,10S)-N-Hydroxy-5-methyl-2-methoxycarbonyl-3-(9-oxo-1,8-diazatricyclo[10.6.1.0]nonadeca-12(19),13(18), 14,16-tetraen-10-ylcarbamoyl)hexanamide;

(3R,9S)-5-Methyl-3-(8-oxo-4-oxa-1,7-diazatricyclo-[9.6.1.0]octadeca-11(18),12,14,16-tetraen-9-ylcarbamoyl)hexanoic acid;

(3R,9S)-3-Cyclobutylmethyl-N-(8-oxo-4-oxa-1,7-diazatricyclo[9.6.1.0]octadeca-11(18),12,14,16-tetraen-9-ylcarbamoyl)succinamic acid;

(3R,9S)-3-(8-Oxo-4-oxa-1,7-diazatricyclo[9.6.1.0]-octadeca-11(18),12,14,16-tetraen-9-ylcarbamoyl)-5-phenoxy-pentanoic acid;

(3R,9S)-5-(4-Chlorophenoxy)-3-(8-oxo-4-oxa-1,7-diazatricyclo[9.6.1.0]octadeca-11(18),12,14,16-tetraen-9-ylcarbamoyl)pentanoic acid;

(3R,9S)-5-(4-Chlorophenoxy)-3-(8-oxo-4-oxa-1,7-diazatricyclo[9.6.1.0]octadeca-11(18),12,14,16-tetraen-9-ylcarbamoyl)pentanoic acid ethyl ester;

(3R,9S)-3-(8-Oxo-1,7-diazatricyclo[9.6.1.0]-octadeca-11(18),12,14,16-tetraen-9-ylcarbamoyl)pentanoic acid ethyl ester;

(3R,9S)-6-(4-Hydroxy-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-6-pyridin-4-yl-hexanoic acid;

(3R,9S)-6-[4-(3-Hydroxy-propoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-5-(4-phenoxy-phenyl)pentanoic acid;

(3R,9S)-6-[4-(2-Hydroxy-ethoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-6-[4-(2-pyrrolidin-1-yl-ethoxyphenyl]hexanoic acid;

(3R,9S)-6-(4-Methoxy-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-6-[4-(2-Methoxy-ethoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-5-phenyl-pentanoic acid;

(3R,9S)-3-(8-Oxo-4-oxa-1,7-diazatricyclo[9.6.1.0]-octadeca-11(18),12,14,16-tetraen-9-ylcarbamoyl)-6-phenyl-hexanoic acid;

(3R,9S)-6-(3-Hydroxy-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-6-[4-(3-piperidin-1-yl-propoxy)phenyl]hexanoic acid;

(3R,9S)-6-[4-(3-Dimethylamino-propoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-6-[4-(2-Dimethylamino-ethoxy)-phenyl]-3-(8-oxo-4-oxa-1,7-diazatricyclo[9.6.1.0]octadeca-11(18),12,14,16-tetraen-9-ylcarbamoyl)hexanoic acid;

(3R,9S)-6-(4-Cyano-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-6-Naphthalen-2-yl-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-6-(4-pyrrol-1-yl)hexanoic acid;

(3R,9S)-6-(4-Hydroxy-3-methyl-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-6-(4-Benzyloxy-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-6-[4-(4-Aminobutoxy-phenyl)]-3-(8-oxo-4-oxa-1,7-diazatricyclo[9.6.1.0]octadeca-11(18),12,14,16-tetraen-9-ylcarbamoyl)hexanoic acid;

(3R,9S)-S-(4-Methoxy-phenyl)-3-(8-oxo-4-oxa-1,7-diazatricyclo[9.6.1.0]octadeca-11(18),12,14,16-tetraen-9-ylcarbamoyl)pentanoic acid;

(3R,9S)-6-(4-Amino-phenyl)-3-(8-oxo-4-oxa-1,7-diazatricyclo[9.6.1.0]octadeca-11(18),12,14,16-tetraen-9-ylcarbamoyl)hexanoic acid;

(3R,9S)-3-(8-Oxo-4-oxa-1,7-diazatricyclo[9.6.1.0]-octadeca-11(18),12,14,16-tetraen-9-ylcarbamoyl)-6-[4-(pyridin-4-ylmethoxy)phenyl]hexanoic acid;

(3R,9S)-6-(4-Acetylamino-phenyl)-3-(8-oxo-4-oxa-1,7-diazatricyclo[9.6.1.0]octadeca-11(18),12,14,16-tetraen-9-ylcarbamoyl)hexanoic acid;

$N^\alpha$-[[3-(N-Hydroxycarbamoyl)-4-methylthio-2-propoxymethyl]butylyl]-N,O-dimethyltyrosine amide;

$N^\alpha$-[[3-(N-Hydroxycarbamoyl)-4-isopropylthio-2-propoxymethyl]butylyl]-N,O-dimethyltyrosine amide;

$N^\alpha$-[[3-(N-Hydroxycarbamoyl)-2-propylthio]butylyl]-N,O-dimethyltyrosine amide;

N-[N-(1-Phosphono-3-phenylpropyl)-(S) -leucyl]-(S)-phenylalanine-N-methylamide;

N-[N-(1-Phosphono-3-(4-bromo-1,8-naphthalene-dicarboximido)propyl)-(S)-leucyl]-(S)-phenylalanine methylamide;

N-[N-(1-Phosphono-3-(benzyloxycarbonylamino)-propyl)-(S)-leucyl]-(S)-phenylalanine methylamide;

N-[N-(1-Phosphono-3-(2-hydroxyphenyl)propyl)-(S)-leucyl]-(S)-phenylalanine methylamide;

N-[N-(1-Phosphono-3-(methylmercapto)propyl)-(S)-leucyl]-(S)-phenylalanine-N-methylamide;

N-[N-(1-Phosphono-3-(methylsulphinyl)propyl)-(S)-leucyl]-(S)-phenylalanine-N-methylamide;

N-[N-(1-Phosphono-3-(methylsulphonyl)propyl)-(S)-leucyl]-(S)-phenylalanine-N-methylamide;

N-[N-(1-Phosphono-3-(1,8-naphthalene-dicarboximido) propyl)-(S)-leucyl]-(S)-tryptophan-N-methylamide;

N-[N-(1-Phosphono-3-(1,8-naphthalene-dicarboximido) propyl)-(S)-leucyl]-(S)-lysine-N-methylamide;

N-[N-(1-Phosphono-3-(1,8-naphthalene-dicarboximido) propyl)-(S)-leucyl]-(–)-aminoazacyclotridecan-2-one;

N-[N-(1-Phosphono-3-(1,8-naphthalene-dicarboximido) propyl)-(S)-leucyl]-(S)-lysine-N-(aminoethyl)amide;

N-[N-(1-Phosphono-3-(1,8-naphthalene-dicarboximido) propyl)-(S)-leucyl]-(S)-lysine-N-(ethylpyrrolidine)amide;

N-[N-(1-Phosphono-3-(1,8-naphthalene-dicarboximido) propyl)-(S)-leucyl]-(S)-lysine-N-(ethyl-N-methylpiperazine)amide;

N-[N-(1-Phosphono-3-[8-(7,9-dioxo-8-azaspiro-[4,5] decyl)]propyl)-(S)-leucyl]-(S)-phenylalanine-N-methylamide; and N-[N-(1-Phosphono-3-[8-(7,9-dioxo-8-azaspiro-[4,5] decyl)]propyl)-(S)-leucyl]-(S)-lysine-N-methylamide.

As noted above, numerous inhibitors of matrix metalloproteinases are known. A large number of inhibitors are characterized as hydroxamic acid-based and/or carboxylic acid-based compounds. Typical of such compounds are those described in the following references, all of which are incorporated herein by reference, since all of the disclosed compounds can be used in the method of this invention.

| | |
|---|---|
| US 4599361 | (Searle) |
| EP-A-2321081 | (ICI) |
| EP-A-0236872 | (Roche) |
| EP-A-0274453 | (Bellon) |
| WO 90/05716 | (British Biotechnology) |
| WO 90/05719 | (British Biotechnology) |
| WO 91/02716 | (British Biotechnology) |
| WO 92/09563 | (Glycomed) |
| US 5183900 | (Glycomed) |
| US 5270326 | (Glycomed) |
| WO 92/17460 | (Smith-Kline Beecham) |
| EP-A-0489577 | (Celltech) |
| EP-A-0489579 | (Celltech) |
| EP-A-0497192 | (Roche) |
| US 5256657 | (Sterling Winthrop) |
| WO 92/13831 | (British Biotechnology) |
| WO 92/22523 | (Research Corporation Technologies) |
| WO 93/09090 | (Yamanouchi) |

-continued

| | |
|---|---|
| WO 93/09097 | (Sankyo) |
| WO 93/20047 | (British Biotechnology) |
| WO 93/24449 | (Celltech) |
| WO 93/24475 | (Celltech) |
| EP-A-0574758 | (Roche) |
| WO 94/02447 | (British Biotechnology) |
| WO 94/02446 | (British Biotechnology) |
| WO 97/27174 | (Shionogi) |

An especially preferred group of compounds to be employed in the present method are those described in WO 95/35275 and WO 95/35276, both of which are incorporated herein by reference. Typical compounds from within these groups to be employed include:

N-Hydroxy-2-[[(2-(4-methoxy-phenoxy)-ethyl-(toluene-4-sulfonyl)-amino]-acetamide;

N-Hydroxy-2-[(4-phenoxy-ethyl)-toluene-4-sulfonyl) amino]-acetamide;

N-Hydroxy-2-[(4-methoxy-benzenesulfonyl)-nonyl-amino]-acetamide;

2-[-Decyl-(toluene-4-sulfonyl)-amino]-N-hydroxy-acetamide;

2-Benzyl-(octane-1-sulfonyl)-amino]-N-hydroxy-acetamide;

N-Hydroxy-2-[(2-methoxy-benzyl)-(octane-1-sulfonyl)-amino]-acetamide;

2-[(2-Ethoxy-benzyl)-(octane-1-sulfonyl)-amino]-N-hydroxy-acetamide;

N-Hydroxy-2-[(naphthalen-2-yl-methyl)-(octane-1-sulfonyl)-amino]-acetamide;

2-[(4-Chloro-benzyl)-(octane-1-sulfonyl)-amino]-N-hydroxy-acetamide, and salts, solvates, or hydrates thereof.

Another class of matrix metalloproteinase inhibitors are aryl sulfonamides of the formula

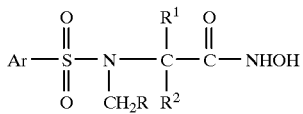

where Ar is carbocyclic or heterocyclic aryl, and R, $R^1$, and $R^2$ include hydrogen, alkyl, aryl, heteroaryl, amino, substituted and disubstituted amino. These compounds are disclosed in European Patent Number 0606046, incorporated herein by reference. Specific compounds to be employed in the present method include:

N-Hydroxy-2-[[4-methoxybenzenesulfonyl](isobutyl) amino]acetamide;

N-Hydroxy-2-[[4-methoxybenzenesulfonyl] (cyclohexylmethyl)amino]acetamide;

N-Hydroxy-2-[[4-methoxybenzenesulfonyl](cyclohexyl) amino]acetamide;

N-Hydroxy-2-[[4-methoxybenzenesulfonyl](phenethyl) amino]acetamide;

N-Hydroxy-2-[[4-methoxybenzenesulfonyl](3-methylbutyl)amino]acetamide;

N-Hydroxy-2-[[4-methoxybenzenesulfonyl](sec-butyl) amino]acetamide;

N-Hydroxy-2-[[4-methoxybenzenesulfonyl](tert-butyl) amino]acetamide

N-Hydroxy-2-[[4-methoxybenzenesulfonyl](4-fluorobenzyl)amino]acetamide

N-Hydroxy-2-[[4-methoxybenzenesulfonyl](4-chlorobenzyl)amino]acetamide

N-Hydroxy-2-[[4-methoxybenzenesulfonyl](isopropyl)-amino]acetamide

N-Hydroxy-2-[[4-methoxybenzenesulfonyl](4-methylbenzyl)amino]acetamide

4-N-Hydroxy-carbamoyl]-4-[[4-methoxybenzenesulfonyl(benzyl)-amino]-1-[dimethylaminoacetyl]-piperidine hydrochloride 4-N-Hydroxy-carbamoyl]-4-[[4-methoxybenzenesulfonyl(benzyl)-amino]-1-[3-picolyl]-piperidine dihydrochloride 4-N-Hydroxy-carbamoyl]-4-[[4-methoxybenzenesulfonyl(benzyl)-amino]-1-[carbomethoxymethyl]-piperidine hydrochloride 4-N-Hydroxy-carbamoyl]-4-[[4-methoxybenzenesulfonyl(benzyl)-amino]-1-piperidine trifluoroacetate;

4-N-Hydroxy-carbamoyl]-4-[[4-methoxybenzenesulfonyl(benzyl)-amino]-1-[t-butoxycarbonyl]-piperidine;

4-N-Hydroxycarbamoyl]-4-[[4-methoxybenzenesulfonyl(benzyl)-amino]-1-[methylsulfonyl]-piperidine;

N-Hydroxycarbamoyl]-4-[[4-methoxybenzene-sulfonyl (benzyl)-amino]-1-[4-picoly]-piperidine hydrochloride;

N-Hydroxycarbamoyl]-4-[[4-methoxybenzene-sulfonyl (benzyl)amino]-1-[morpholinocarbonyl]-piperidine hydrochloride; and N-(t-Butyloxy)-2-[[4-methoxybenzenesulfonyl (benzyl) amino]-2-[2-(4-morpholino)ethyl]acetamide.

The following compounds are prepared similarly to Example 7:

N-Hydroxy-2-[[4-methoxybenzenesulfonyl](isobutyl)-amino-2-(2-(4-morpholino)ethyl]acetamide;

N-Hydroxy-2-[[4-methoxybenzenesulfonyl](2-picoly)-amino-2-(2-(4-morpholino)ethyl]acetamide dihydrochloride;

N-Hydroxy-2-[[4-methoxybenzenesulfonyl](3-picolyl) amino]-2-[2-(4-morpholino)ethyl]acetamide dihydrochloride;

N-Hydroxy-2-[[4-methoxybenzenesulfonyl](2-methyl-thiazol-4-ylmethyl)amino]-2-[2-(4-morpholino) ethyl] acetamide dihydrochloride;

N-Hydroxy-2-[[4-methoxybenzenesulfonyl]benzyl) amino]-2-[2-(4-thiomorpholino]ethyl]acetamide;

N-Hydroxy-2-[[4-methoxybenzenesulfonyl](benzyl) amino]-2-[2-(4-methylthiazol-4-ylmethyl]acetamide;

N-Hydroxy-2-[[4-methoxybenzenesulfonyl (benzyl) amino]-2-[(6-chloropiperonyl]acetamide;

N-Hydroxy-2-[[4-methoxybenzenesulfonyl (benzyl) amino]-2-[(1-pyrazolyl)methyl]acetamide;

N-Hydroxy-2-[[4-methoxybenzenesulfonyl (3-picolyl) amino]-2-[3-picolyl]acetamide;

N-Hydroxy-2-[[4-methoxybenzenesulfonyl(benzyl)-amino]-2-[(1-methyl-4-imidazolyl)methyl]acetamide hydrochloride;

N-Hydroxy-2-[[4-methoxybenzenesulfonyl(isobutyl) amino]-2-[(1-methyl-4-imidazolyl)methyl]acetamide hydrochloride;

N-Hydroxy-2-[[4-methoxybenzenesulfonyl](3-picolyl) amino]-2-[(1-methyl-4-imidazolyl) methyl]acetamide hydrochloride;

N-Hydroxy-2-[[4-methoxybenzenesulfonyl(2-picolyl) amino]-2-[(1-methyl-4-imidazolyl)methyl]-acetamide hydrochloride; and N-Hydroxy-2-[[4-methoxybenzenesulfonyl](2-methylthiazol-4-ylmethyl)amino-2-[(1-methyl-4-imidazolyl)methyl]acetamide hydrochloride.

Another group of small peptide matrix metalloproteinase inhibitors are described in U.S. Pat. Nos. 5,270,326, 5,530, 161, 5,525,629, and 5,304,604 (incorporated herein by reference). The compounds are hydroxamic acids defined by the formula.

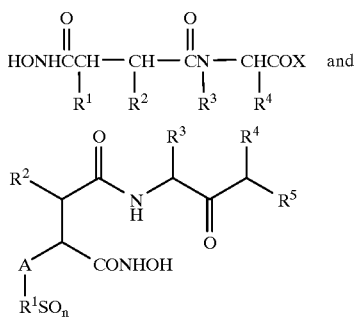

where $R^1$, $R^2$, $R^3$, and $R^4$ can be hydrogen or alkyl and X is $OR^5$ or $NHR^5$ where $R^5$ includes hydrogen, alkyl and aryl, A includes alkyl, and n is 0 to 2. Typical compounds to be employed in the instant method include the following:

N-[2-Isobutyl-3-(N'-hydroxycarbonylamido)-propanoyl]-D-tryptophan methylamide;

N-[2-Isobutyl-3-(N'-hydroxycarbonylamido)-propanoyl]-N-methyl-L-tryptophan methylamide;

N-[2-Isobutyl-3-(N'-hydroxycarbonylamido)-propanoyl]-L-3-(2-naphthyl)-alanine methylamide;

N-[2-Isobutyl-3-(N'-hydroxycarbonylamido)-propanoyl]-L-tryptophan 2-hydroxyethylamide;

N-[2-Isobutyl-3-(N'-hydroxycarbonylamido)-propanoyl]-L-tryptophan amylamide;

N-[2-Isobutyl-3-(N'-hydroxycarbonylamido)-propanoyl]-L-tryptophan piperidinamide;

N-[2-Isobutyl-3-(N'-hydroxycarbonylamido)-propanoyl-L-tryptophan dodecylamide;

N-[2-Isobutyl-3-(N'-hydroxycarbonylamido)-propanoyl]-L-tryptophan(S)-methylbenzylamide;

N-[L-2-Isobutyl-3-(N'-hydroxycarbonylamido)-propanoyl]-L-tryptophan(6-phenylmethoxycarbonyl-amino-hexyl-1)amide;

2S-Hydroxy-3R-[1S-(3-methoxy-2,2-dimethyl-propylcarbamoyl)-2,2-dimethyl-propylcarbamoyl]-5-methyl-hexanohydroxamic acid;

2S-Hydroxy-3R-[1S-(methylcarbamoyl)-2,2-dimethyl-propylcarbamoyl]-6-(4-chloro)phenyl-hexanohydroxamic acid;

2S-Hydroxy-3R-[1S-(methylcarbamoyl)-2,2-dimethyl-propylcarbamoyl]octanohydroxamic acid;

2S-Hydroxy-3R-[1S-(pyridin-2-ylmethylcarbamoyl)-2,2-dimethyl-propylcarbamoyl]-5-methyl-hexanohydroxamic acid;

2S-Hydroxy-3R-[1S-(pyridin-3-ylmethylcarbamoyl)-2,2-dimethyl-propylcarbamoyl]-5-methyl-hexanohydroxamic acid;

2S-Hydroxy-3R-[1S-(pyridin-4-ylmethylcarbamoyl)-2,2-dimethyl-propylcarbamoyl]-5-methyl-hexanohydroxamic acid;

2S-Hydroxy-3R-[1S-(methylcarbamoyl)-2,2-dimethyl-propylcarbamoyl]-4-methoxy-butanohydroxamic acid;

2S-Hydroxy-3R-[1S-(methylcarbamoyl)-2,2-dimethyl-propylcarbamoyl]-4-benzyloxy-butanohydroxamic acid;

2S-Hydroxy-3R-[1S-(methylcarbamoyl)-2,2-dimethyl-propylcarbamoyl]-4-benzylthio-butanohydroxamic acid;

2S-Hydroxy-3R-[1S-(methylcarbamoyl)-2,2-dimethyl-buten-3-ylcarbamoyl]-5-methyl-hexanohydroxamic acid;

2S-Hydroxy-3R-[1S-(tert-butylcarbamoyl)-2,2-dimethyl-propylcarbamoyl]-5-methyl-hexanohydroxamic acid;

2S-Hydroxy-3R-[1S-(N,N-dimethyl-carbamoyl)-2,2-dimethyl-propylcarbamoyl]-5-methyl-hexanohydroxamic acid;

2S-Hydroxy-3R-[1S-(3-hydroxy-2,2-dimethyl-propylcarbamoyl)-2,2-dimethyl-propylcarbanoyl]-5-methyl-hexanohydroxamic acid;

2S-Hydroxy-3R-[1S-(methylcarbamoyl)-2,2-dimethyl-propylcarbamoyl]-6-phenyl-hexanohydroxamic acid;

2S-Hydroxy-3R-[1S-(methylcarbamoyl)-2,2-dimethyl-butylcarbamoyl]-5-methyl-hexanohydroxamic acid;

[4-(N-Hydroxyamino)-2R-isobutylsuccinyl]-L-phenylalanine-N-(2-hydroxyethyl)-amide;

[4-(N-Hydroxyamino)-2R-isobutylsuccinyl]-L-phenylalaninyl-proline;

[4-(N-Hydroxyamino)-2R-isobutylsuccinyl]-L-phenylalanine-N-(2-hydroxyethyl)-N-methylamide;

[4-(N-Hydroxyamino)-2R-isobutylsuccinyl]-L-phenylalaninyl-D-prolinol;

[4-(N-Hydroxyamino)-2R-isobutylsuccinyl]-L-phenylalaninyl-L-prolinol;

[4-(N-Hydroxyamino)-2R-isobutylsuccinyl]-L-phenylalanine-N-(5-N-methyl-pentylcarboxamide)amide;

[4-(N-Hydroxyamino)-2R-isobutylsuccinyl]-L-phenylalanine-N-(2-ethylthioethyl)amide;

[4-(N-Hydroxyamino)-2R-isobutylsuccinyl]-L-phenylalanine-N-(2-methoxyethyl)amide;

[4-(N-Hydroxyamino)-2R-isobutylsuccinyl]-L-phenylalanine-N-(2-N-acetylethyl)amide;

[4-(N-Hydroxyamino)-2R-isobutylsuccinyl]-L-phenylalanine-N-(3-(2-pyrrolidone)propyl)amide;

[4-(N-Hydroxyamino)-2R-isobutylsuccinyl]-L-phenylalanine-N-(3-(2-pyrrolidone)propyl)amide sodium salt;

[4-(N-Hydroxyamino)-2R-isobutylsuccinyl]-L-phenylalanine-N-(2-acetoxyethyl)amide;

[4-(N-Hydroxyamino)-2R-isobutyl-3S-methylsuccinyl]-L-phenylalanine-N-(3-(2-pyrrolidone)propyl)amide;

[4-(N-Hydroxyamino)-2R-isobutyl-3S-methylsuccinyl]-L-phenylalanine-N-methyl-N-(2-hydroxyethyl)amide;

[4-(N-Hydroxyamino)-2R-isobutyl-3S-methylsuccinyl]-L-phenylalanine-N-(2-hydroxyethyl)amide;

[4-(N-Hydroxyamino)-2R-isobutyl-3S-methylsuccinyl]-L-phenylalaninyl-D-prolinol;

[4-(N-Hydroxyamino)-2R-isobutyl-3S-methylsuccinyl]-L-phenylalanine-N-(3-(2-pyrrolidone)propyl)amide sodium salt;

[4-(N-Hydroxyamino)-2R-isobutyl-3S-methylsuccinyl]-L-phenylalanine-N-(3-(2-pyrrolidone)propyl)amide;

[4-(N-Hydroxyamino)-2R-isobutyl-3S-methylsuccinyl]-L-phenylalanine-N-(3-(2-pyrrolidone)propyl)amide or a salt thereof;

$N^2$-[4-(N-Hydroxyamino)-3S-(4-hydroxyphenyl-thiomethyl)-2R-isobutylsuccinyl]-$N^6$-tert-butyloxycarbonyl-L-lysine-$N^1$-methylamide;

$N^2$-[4-(N-Hydroxyamino)-3S-(4-hydroxyphenyl-thiomethyl)-2R-isobutylsuccinyl]-$N^6$-tert-butyloxycarbonyl-$N^6$-(4-hydroxyphenylthiomethyl)-L-lysine-$N^1$-methylamide;

$N^2$-[4-(N-Hydroxyamino)-3S-(2-thienylthiomethyl)-2R-isobutylsuccinyl]-$N^6$-tert-butyloxycarbonyl-L-lysine-$N^1$-methylamide;

$N^2$-[4-(N-Hydroxyamino)-3S-(4-hydroxyphenyl-thiomethyl)-2R-isobutylsuccinyl]-O-tert-butyl-L-threonine-$N^1$-methylamide;

$N^2$-[4-(N-Hydroxyamino)-3S-(4-hydroxyphenyl-thiomethyl)-2R-isobutylsuccinyl]-L-glutamine-$N^1$,$N^5$-dimethylamide;

$N^2$-[4-(N-Hydroxyamino)-3S-(4-hydroxyphenyl-sulphonylmethyl)-2R-isobutylsuccinyl]-$N^6$-acetyl-L-lysine-$N^1$-methylamide;

3R-(3-Methoxycarbonyl-1S-methylcarbamoyl-propylcarbamoyl)-5-methyl-2S-2-propenyl-hexanohydroxamic acid;

3R-(1S-Methylcarbamoyl-2-thien-2-yl-ethyl-carbamoyl)-5-methyl-2S-2-propenyl-hexanohydroxamic acid;

3R-(3-Methyl-1S-methylcarbamoyl-butylcarbamoyl)-5-methyl-2S-2-propenyl-hexanohydroxamic acid;

2S-[1S-Methylcarbamoyl-2-oxadiazol-5-yl-ethylcarbamoyl)-5-methyl-2S-2-propenyl-hexanohydroxamic acid;

[4-(N-Hydroxyamino)-2R-isobutylsuccinyl]-L-(4-oxymethylcarboxylic acid)phenylalanine-N-methylamide;

[4-(N-Hydroxyamino)-2R-isobutylsuccinyl]-L-(4-oxymethylcarboxy-N-methylamide)phenylalanine-N-methylamide;

[4-(N-Hydroxyamino)-2R-isobutylsuccinyl]-L-(4-oxymethylcarboxy-beta-alanine)phenylalanine-N-methylamide;

[4-(N-Hydroxyamino)-2R-isobutylsuccinyl]-L-(4-oxymethylcarboxyglycine)phenylalanine-N-methylamide;

[4-(N-Hydroxyamino)-2R-isobutylsuccinyl]-L-(4-oxymethylcarboxy-N-benzylamide)phenylalanine-N-methylamide;

[4-(N-Hydroxyamino)-2R-isobutylsuccinyl]-L-(4-cyano)phenylalanine-N-methylamide;

[4-(N-Hydroxyamino)-2R-isobutylsuccinyl]-L-(4-acetamido)phenylalanine-N-methylamide;

[4-(N-Hydroxyamino)-2R-isobutylsuccinyl]-L-(4-oxymethylcarboxamide)-henylalanine-N-methylamide;

[4-(N-Hydroxyamino)-2R-isobutyl-3S-(2-thienylthiomethylsuccinyl]-L-(4-N-acetylamino)-henylalanine-N-methylamide;

[4-(N-Hydroxyamino)-2R-isobutyl-3S-(2-thienylthiomethylsuccinyl]-L-(4-N-methylsuccinylamide)-phenylalanine-N-methylamide;

[4-(N-Hydroxyamino)-2R-isobutyl-3S-(4-aminophenylthiomethyl)-succinyl]-L-(4-N-(methylsuccinylamide)phenylalanine-N-methylamide;

[4-(N-Hydroxyamino)-2R-isobutyl-3S-(4-aminophenylthiomethylsuccinyl]-L-(4-N-(4-(4-oxobutanoic acid)aminophenylalanine-N-methylamide;

[4-(N-Hydroxyamino)-2R-isobutyl-3S-(4-hydroxyphenylthiomethyl)-succinyl]-L-(4-N-methylsuccinylamido)phenylalanine-N-methylamide;

[4-(N-Hydroxyamino)-2R-isobutyl-3S-(4-hydroxyphenylthiomethyl)-succinyl]-L-(4-N-(4-(4-oxobutanoic acid)aminophenylalanine-N-methylamide;

[4-(N-Hydroxyamino)-2R-isobutyl-3S-(2-thienylthiomethyl)-succinyl]-L-(4-oxymethylcarboxymethyl)phenylalanine-N-methylamide;

[4-(N-Hydroxyamino)-2R-isobutyl-3S-(2-thienylthiomethyl)-succinyl]-L-(4-N-(oxymethylcarboxylic acid)phenylalanine-N-methylamide;

[4-(N-Hydroxyamino)-2R-isobutyl-3S-(2-thienylthiomethyl)-succinyl]-L-4-oxymethylcarboxyglycyl methyl ester)-phenylalanine-N-methylamide;

[4-(N-Hydroxyamino)-2R-isobutyl-3S-(2-thienylthiomethyl)-succinyl]-L-4-oxymethylcarboxy-glycine)phenylalanine-N-methylamide;

[4-(N-Hydroxyamino)-2R-isobutyl-3S-methyl-succinyl]-L-4-(oxymethylcarboxyglycyl methyl ester)phenylalanine-N-methylamide;

[4-(N-Hydroxyamino)-2R-isobutyl-3S-methyl)-succinyl]-L-4-(oxymethylcarboxyglycine)-phenylalanine-N-methylamide;

[4-(N-Hydroxyamino)-2R-isobutylsuccinyl]-L-4-oxymethylnitrile)-phenylalanine-N-methylamide;

[4-(N-Hydroxyamino)-2R-isobutylsuccinyl]-L-3-(1-(2-methyloxycarbonyl)-ethyl)-4-methoxyphenylalanine-N-methylamide;

[4-(N-Hydroxyamino)-2R-isobutylsuccinyl]-L-3-(hydroxymethyl)-4-methoxyphenylalanine-N-methylamide;

[4-(N-Hydroxyamino)-2R-isobutylsuccinyl]-L-3-methyl-4-methoxyphenylalanine-N-methylamide;

2-[Benzyl-(octane-1-sulfonyl)-amino]-N-hydroxy-acetamide;

N-Hydroxy-2-[(2-methoxy-benzyl)-(octane-1-sulfonyl)-amino]-acetamide;

2-[(2-Ethoxy-benzyl)-(octane-1-sulfonyl)-amino]-N-hydroxy-acetamide;

N-Hydroxy-2-[(naphthalen-2-yl-methyl)-(octane-1-sulfonyl)-amino]-acetamide;

2-[(4-Chloro-benzyl)-(octane-1-sulfonyl)-amino]-N-hydroxy-acetamide;

$N^2$-[3S-Hydroxy-4-(N-hydroxyamino)-2R-isobutylsuccinyl]-L-leucine-$N^1$-methylamide;

$N^2$-[3S-Hydroxy-4-(N-hydroxyamino)-2R-isobutylsuccinyl)]-5-methyl-L-glutamic acid-$N^1$-methylamide;

$N^2$-[3S-Hydroxy-4-(N-hydroxyamino)-2R-isobutylsuccinyl)]-L-phenylalanine-$N^1$-methylamide;

[4-(N-Hydroxyamino)-2R-isobutyl-3S-(thienylthiomethyl)succinyl]-L-phenylalanine-N-methylamide;

[4-(N-Hydroxyamino)-2R-isobutyl-3S-phenylthiomethyl)succinyl]-L-phenylalanine-N-methylamide;

2S-(4-Methoxyphenylsulfanylmethyl)-3R-(2-phenyl-1S-methylcarbamoyl-ethylcarbamoyl)-5-methyl-hexanohydroxamic acid;

2S-(3-Chlorophenylsulfanylmethyl)-3R-(2-phenyl-1S-methylcarbamoyl-ethylcarbamoyl)-5-methyl-hexanohydroxamic acid;

2S-(Phenylsulfanylmethyl)-3R-(2-phenyl-1S-(pyrid-3-ylmethylcarbamoyl)-ethylcarbamoyl)-5-methyl-hexanohydroxamic acid;

2S-(3-Methylphenylsulfanylmethyl)-3R-(2-phenyl-1S-methylcarbamoyl-ethylcarbamoyl)-5-methyl-hexanohydroxamic acid;

2S-(Thien-2-ylsulfanylmethyl)-3R-(2-(4-carboxymethoxyphenyl)-1S-methylcarbamoyl-ethylcarbamoyl)-5-methyl-hexanohydroxamic acid;

2S-(Thien-2-ylsulfanylmethyl)-3R-(2-phenyl-1S-(pyrid-3-ylmethylcarbamoyl)-ethylcarbamoyl)-5-methyl-hexanohydroxamic acid;

2S-(4-Hydroxyphenylsulfanylmethyl)-3R-(2-phenyl-1S-(pyrid-3-ylmethylcarbamoyl)-ethylcarbamoyl)-5-methyl-hexanohydroxamic acid;

2S-(Thien-2-ylsulfanylmethyl)-3R-(2-naph-2-yl-1S-methylcarbamoyl-ethylcarbamoyl)-5-methyl-hexanohydroxamic acid;

2S-(4-Hydroxyphenylsulfanylmethyl)-3R-(2R-hydroxy-1S-methylcarbamoyl-propylcarbamoyl)-5-methyl-hexanohydroxamic acid;

2S-(4-Hydroxyphenylsulfanylmethyl)-3R-(5-acetamido-1S-methylcarbamoyl-pentylcarbamoyl)-5-methyl-hexanohydroxamic acid;

2S-(4-Hydroxyphenylsulfanylmethyl)-3R-(3-[1,1-dimethylethoxycarbonyl]-1S-methylcarbamoyl-propylcarbamoyl)-5-methyl-hexanohydroxamic acid;

2S-(Thien-2-ylsulfonylmethyl)-3R-(2-phenyl-1S-methylcarbamoyl-ethylcarbamoyl)-5-methyl-hexanohydroxamic acid;

3S-(2-[4-Acetamido-phenyl]-1S-methylcarbamoyl-ethylcarbamoyl)-5-methyl-hexanohydroxamic acid;

2S-(4-Phthalimido-butyl)-3R-(3-methyl-1S-ethoxycarbonylmethylcarbamoyl-butylcarbamoyl)-5-methyl-hexanohydroxamic acid;
3R-(2-[4-Methoxy-phenyl]-1S-methylcarbamoyl-ethylcarbamoyl)-2S,5-dimethyl-hexanohydroxamic acid;
3R-(2-Phenyl-1S-[2-oxo-pyrolid-1-yl]-propylcarbamoyl-ethylcarbamoyl)-5-methyl-hexanohydroxamic acid;
3R-(2-[4-Methoxy-phenyl]-1S-methylcarbamoyl-ethylcarbamoyl)-5-methyl-hexanohydroxamic acid;
3R-(2-Phenyl-1S-[pyrid-3-ylmethylcarbamoyl]-ethylcarbamoyl)-5-methyl-hexanohydroxamic acid;
3R-(2,2-Dimethyl-1S-methylcarbamoyl-propylcarbamoyl)-5-methyl-hexanohydroxamic acid;
Isobutylmalonoyl-L-alanine-furfurylamide hydroxamate;
2-Isobutyl-3-carbonyl-3'-(4-acetylaniline)-propionic acid;
N-Benzyloxycarbonyl-α-phosphonoglycyl-L-alanine furfurylamide;
[4-(N-Hydroxyamino)-2R-isobutyl-3S-(phenylthiomethyl)succinyl]-L-phenylalanine-N-methylamide;
[4-(N-Hydroxyamino)-2R-isobutyl-3S-(4-methoxyphenylthiomethyl)succinyl]-L-phenylalanine-N-methylamide;
[4-(N-Hydroxyamino)-2R-isobutyl-3S-(4-hydroxyphenylthiomethyl)succinyl]-L-phenylalanine-N-methylamide;
[4-(N-Hydroxyamino)-2R-isobutyl-3S-(2,4-dimethylphenylthiomethyl)succinyl]-L-phenylalanine-N-methylamide;
[4-(N-Hydroxyamino)-2R-isobutyl-3S-(3-bromophenylthiomethyl)succinyl]-L-phenylalanine-N-methylamide;
[4-(N-Hydroxyamino)-2R-isobutyl-3S-(3-chlorophenylthiomethyl)succinyl]-L-phenylalanine-N-methylamide;
[4-(N-Hydroxyamino)-2R-isobutyl-3S-(3-methylphenylthiomethyl)succinyl]-L-phenylalanine-N-methylamide;
[4-(N-Hydroxyamino)-2R-isobutyl-3S-(4-(N-acetyl)-amino-phenylthiomethyl)succinyl]-L-phenylalanine-N-methylamide;
[4-(N-Hydroxyamino)-2R-isobutyl-3S-phenylsulphinylmethylsuccinyl]-L-phenylalanine-N-methylamide;
3R-(3-Methoxycarbonyl-1S-methylcarbamoyl-propylcarbamoyl)-5-methyl-2S-phenylsulfanylmethyl-hexanohydroxamic acid;
3R-(3-Methoxycarbonyl-1S-methylcarbamoyl-propylcarbamoyl)-5-methyl-2S-(thien-2-ylsulfanylmethyl)-hexanohydroxamic acid;
2S-(4-Methoxy-phenylsulfanylmethyl)-3R-(3-methoxycarbonyl-1S-methylcarbamoyl-propylcarbamoyl)-5-methyl-hexanohydroxamic acid;
2S-(4-Amino-phenylsulfanylmethyl)-3R-(3-methoxycarbonyl-1S-methylcarbamoyl-propylcarbamoyl)-5-methyl-hexanohydroxamic acid;
2S-(Ethylsulfanylmethyl)-3R-(3-methoxycarbonyl-1S-methylcarbamoyl-propylcarbamoyl)-5-methyl-hexanohydroxamic acid;
2S-(Acetylsulfanylmethyl)-3R-(3-methoxycarbonyl-1S-methylcarbamoyl-propylcarbamoyl)-5-methyl-hexanohydroxamic acid;
2S-(Benzylsulfanylmethyl)-3R-(3-methoxycarbonyl-1S-methylcarbamoyl-propylcarbamoyl)-5-methyl-hexanohydroxamic acid;
2S-(tert-Butylsulfanylmethyl)-3R-(3-methoxycarbonyl-1S-methylcarbamoyl-propylcarbamoyl)-5-methyl-hexanohydroxamic acid;
2S-Thiomethyl-3R-(3-methoxycarbonyl-1S-methylcarbamoyl-propylcarbamoyl)-5-methyl-hexanohydroxamic acid;
2S-(4-Hydroxy-phenylsulfanylmethyl)-3R-(2-tert-butoxycarbonyl-1S-methylcarbamoyl-ethylcarbamoyl)-5-methyl-hexanohydroxamic acid;
2S-(4-Hydroxy-phenylsulphinylmethyl)-3R-(3-methoxycarbonyi-1S-methylcarbamoyl-propylcarbamoyl)-5-methyl-hexanohydroxamic acid;
2S-(4-Hydroxy-phenylsulphonylmethyl)-3R-(3-methoxycarbonyl-1S-methylcarbamoyl-propylcarbamoyl)-5-methyl-hexanohydroxamic acid;
[4-(N-Hydroxyamino)-2R-isobutylsuccinyl]-L-phenylalanine-N-[1-(2-aminoethyl)-pyrrolidine]amide;
[4-(N-Hydroxyamino)-2R-isobutylsuccinyl]-L-phenylalanine-N-[1-(3-aminopropyl)-2(RS)-methylpiperidine]amide;
[4-(N-Hydroxyamino)-2R-isobutylsuccinyl]-L-phenylalanine-N-[2-(2-aminoethyl)-1-methylpyrrole]amide;
[4-(N-Hydroxyamino)-2R-isobutylsuccinyl]-L-phenylalanine-N-(3-aminomethylpyridine)amide;
[4-(N-Hydroxyamino)-2R-isobutylsuccinyl]-L-phenylalanine-N-(2-aminomethylpyridine)amide;
[4-(N-Hydroxyamino)-2(RS)-isobutylsuccinyl]-L-phenylalanine-N-(4-aminomethylpyridine)amide;
[4-(N-Hydroxyamino)-2(RS)-isobutylsuccinyl]-L-phenylalanine-N-(1-(3-aminopropyl)-imidazole)amide;
[4-(N-Hydroxyamino)-2(RS)-isobutylsuccinyl]-L-phenylalanine-N-(2-aminomethylbenzimdazole)amide;
[4-(N-Hydroxyamino)-2R-isobutyl-3S-methylsuccinyl]-L-phenylalanine-N-[4-(2-aminoethyl)-morpholino]amide;
[4-(N-Hydroxyamino)-2R-isobutylsuccinyl]-L-phenylalanine-N-[4-(2-aminoethyl)-morpholine]amide;
[4-(N-Hydroxyamino)-2(R,S)-isobutylsuccinyl]-L-phenylalanine-N-[2-(2-aminoethyl)-pyridine]amide;
[4-(N-Hydroxyamino)-2(R,S)-isobutylsuccinyl]-L-phenylalanine-N-[4-(2-aminopropyl)-morpholine]amide;
[4-(N-Hydroxyamino)-2R-isobutylsuccinyl]-L-phenylalanine-N-(3-aminomethylpyridine)amide hydrochloride; and
[4-(N-Hydroxyamino)-2R-isobutylsuccinyl]-L-phenylalanine-N-[4-(2-aminoethyl)-morpholine]amide hydrochloride.

In a preferred embodiment, tricyclic butyric acid derivatives which are inhibitors of matrix metalloprotienases are employed to treat or prevent heart failure and ventricular dilatation according to this invention. A preferred group of tricyclic butyric acid derivatives are defined by the formula:

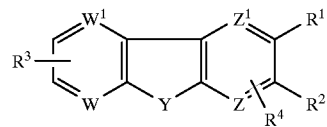

wherein one of $R^1$ or $R^2$ is

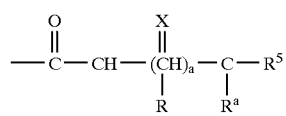

wherein X is O,
N—$OR^6$ wherein $R^6$ is hydrogen,
—$(CH_2)_n$-aryl wherein n is zero or an integer of 1 to 5, alkyl, or —(CH$_2$)$_n$-cycloalkyl wherein n is as defined above, or

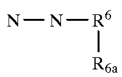

wherein R$^6$ and R$^{6a}$ are each the same or different and each is as defined above for R$^6$;

R and R$^a$ are each the same or different and each is hydrogen,
- —(CH$_2$)$_n$-aryl wherein n is as defined above,
- —(CH$_2$)$_n$-heteroaryl wherein n is as defined above,
- —(CH$_2$)$_p$—R$^7$—(CH$_2$)$_q$-aryl wherein R$^7$ is O or S and p or q is each zero or an integer of 1 to 5 and the sum of p+q equals an integer of 5,
- —(CH$_2$)$_p$—R$^7$—(CH$_2$)$_q$-heteroaryl wherein p, q, and R$^7$ are as defined above, alkyl,
- —(CH$_2$)$_n$-cycloalkyl wherein n is as defined above, or
- —(CH$_2$)$_r$—NH$_2$ wherein r is an integer of 1 to 9;

a is zero or an integer of 1 to 3;

R$^5$ is OH,

OR$^6$ wherein R$^6$ is as defined above,

wherein R$^6$ and R$^{6a}$ are each the same or different and are as defined above for R$^6$, or NH—OR$^6$ wherein R$^6$ is as defined above;

R$^3$ and R$^4$ are each the same or different and each is hydrogen,
alkyl,
NO$_2$,
halogen,
OR$^6$ wherein R$^6$ is as defined above,
CN,
CO$_2$R$^6$ wherein R$^6$ is as defined above,
SO$_3$R$^6$ wherein R$^6$ is as defined above,
CHO,

wherein R is as defined above,

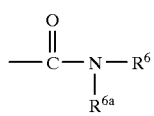

wherein R$^6$ and R$^{6a}$ are each the same or different and are as defined above for R$^6$, or

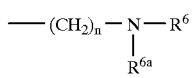

wherein R$^6$ and R$^{6a}$ are each the same or different and are as defined above for R$^6$;

W, W$^1$, Z, and Z$^1$ are each the same or different and each is CR$^3$ wherein R$^3$ is as defined above, or N providing only one of W or W$^1$ is N and/or only one of Z or Z$^1$ is N; and Y is

wherein R is as defined above,
—O—,
—S—(O)$_m$— wherein m is zero or an integer of 1 or 2,
—CH$_2$—,

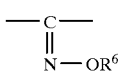

wherein R$^6$ is as defined above,

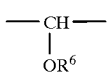

wherein R$^6$ is as defined above,

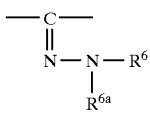

wherein R$^6$ and R$^{6a}$ are the same or different and are as defined above for R$^6$,

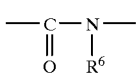

wherein R$^6$ is as defined above,

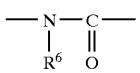

wherein R$^6$ is as defined above,

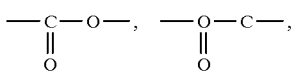

—CH$_2$—O—,
—O—CH$_2$—,
—CH$_2$—S(O)$_m$— wherein m is as defined above,

—S(O)$_m$—CH$_2$— wherein m is as defined above,

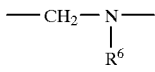

wherein R$^6$ is as defined above,

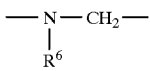

wherein R$^6$ is as defined above,

—CH=N—, or

—N=CH—;

with the proviso that when X is O, and R$^5$ is not NH—OR$^6$, at least one of R or R$^a$ is not hydrogen; and corresponding isomers thereof; or a pharmaceutically acceptable salt thereof.

Typical compounds from this class include:

4-Dibenzofuran-2-yl-4-hydroxyimino-butyric acid;

2-(2-Dibenzofuran-2-yl-2-hydroxyimino-ethyl)-4-methyl-pentanoic acid;

2-(2-Dibenzofuran-2-yl-2-hydroxyimino-ethyl)-5-phenyl-pentanoic acid;

4-Dibenzofuran-2-yl-4-hydroxyimino-2-phenethyl-butyric acid;

5-(4-Chloro-phenyl)-2-(2-dibenzofuran-2-yl-2-hydroxyimino-ethyl)-pentanoic acid;

2-(2-Dibenzofuran-2-yl-2-hydroxyimino-ethyl)-5-(4-fluoro-phenyl)-pentanoic acid;

2-(2-Dibenzofuran-2-yl-2-hydroxyimino-ethyl)-5-(4-methoxy-phenyl)-pentanoic acid;

2-(2-Dibenzofuran-2-yl-2-hydroxyimino-ethyl)-5-p-tolyl-pentanoic acid;

3-(Dibenzofuran-2-yl-hydroxyimino-methyl)-5-methyl-hexanoic acid;

3-(Dibenzofuran-2-yl-hydroxyimino-methyl)-6-phenyl-hexanoic acid;

3-(Dibenzofuran-2-yl-hydroxyimino-methyl)-5-phenyl-pentanoic acid;

6-(4-Chloro-phenyl)-3-(dibenzofuran-2-yl-hydroxyimino-methyl)-hexanoic acid;

3-(Dibenzofuran-2-yl-hydroxyimino-methyl)-6-(4-fluoro-phenyl)-hexanoic acid;

3-(Dibenzofuran-2-yl-hydroxyimino-methyl)-6-(4-methoxyphenyl)-hexanoic acid; and 3-(Dibenzofuran-2-yl-hydroxyimino-methyl)-6-p-tolyl-hexanoic acid; and corresponding isomers thereof; or a pharmaceutically acceptable salt thereof.

Tricyclic butyric acids having an α-amino substituent are defined by the formula:

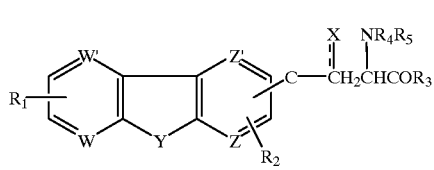

wherein:

X is O, NOR$_9$, S, OH, SH, or

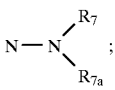

R$_7$ and R$_{7a}$ independently are hydrogen,

C$_1$–C$_{20}$ alkyl or substituted C$_1$–C$_{20}$ alkyl, (CH$_2$)$_{0-6}$-aryl, (CH$_2$)$_{0-6}$-heteroaryl, or (CH$_2$)$_{0-6}$-cycloalkyl;

R$_1$ and R$_2$ independently are hydrogen,

C$_1$–C$_{20}$ alkyl or substituted C$_1$–C$_{20}$ alkyl, halo,

NO$_2$,

CN,

CHO,

COR$_6$,

COOR$_6$,

SO$_3$R$_6$,

OR$_6$,

CONR$_4$R$_5$, (CH$_2$)$_{0-6}$-aryl, (CH$_2$)$_{0-6}$-heteroaryl, or (CH$_2$)$_{0-6}$-cycloalkyl;

R$_6$ is hydrogen,

C$_1$–C$_{20}$ alkyl or substituted C$_1$–C$_{20}$ alkyl;

aryl is phenyl or substituted phenyl;

R$_3$ is hydroxy,

O—C$_1$–C$_{20}$ alkyl or substituted O—C$_1$–C$_{20}$ alkyl,

O—(CH$_2$)$_{1-3}$ aryl, or

NHOR$_6$;

R$_4$ and R$_5$ independently are hydrogen,

C$_1$–C$_{20}$ alkyl or substituted C$_1$–C$_{20}$ alkyl, (CH$_2$)$_{0-6}$-aryl, (CH$_2$)$_{0-6}$-heteroaryl; or one of R$_4$ and R$_5$ is hydrogen and the other is:

Y is

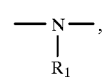

—O—,

—S(O)$_{0, 1\ or\ 2}$,

—CH₂—, $$-\underset{\underset{O}{\|}}{C}-,$$

$$-\underset{\underset{NOR_8}{\|}}{C}-,$$

$$-\underset{\underset{OR_8}{|}}{CH}-,$$

$$-\underset{\underset{N-N-R_8R_9}{\|}}{C}-,$$

$$-\underset{\underset{O\ \ R_8}{\|\ \ \ |}}{C-N}-,$$

$$-\underset{\underset{R^8\ \ O}{|\ \ \ \|}}{N-C}-,$$

$$-\underset{\underset{O}{\|}}{C}-O,$$

—CH₂—O—,
—O—CH₂—,
—CH₂S(O)₀, ₁ or ₂,
—S(O)₀, ₁ or ₂—CH₂—, $$-\underset{\underset{R_8}{|}}{CH_2-N}-,$$

$$-\underset{\underset{R_8}{|}}{N-CH_2}-,$$

—CH=N, or
—N=CH—;
R₈ and R₉ independently are
hydrogen
$C_1$–$C_{20}$ alkyl or substituted $C_1$–$C_{20}$ alkyl,
$(CH_2)_{0-6}$-aryl,
$(CH_2)_{0-6}$-heteroaryl, or
$(CH_2)_{0-6}$-cycloalkyl;
W, W¹, Z, and Z¹ independently are CR₁ or N; and the pharmaceutically acceptable salts, isomers, stereoisomers, and solvates thereof.

Specific examples of compounds to be employed in the present method include:

(S)-4-Dibenzofuran-2-yl-4-oxo-2-(2,2,2-trifluoroacetylamino)-butyric acid;
(R)-4-Dibenzofuran-2-yl-4-oxo-2-(2,2,2-trifluoroacetylamino)-butyric acid;
(S)-2-Amino-4-dibenzofuran-2-yl-4-oxo-butyric acid
(S)-2-Acetylamino-4-dibenzofuran-2-yl-4-oxo-butyric;
(S)-4-Dibenzofuran-2-yl-2-[3-(2,6-diisopropyl-phenyl)-ureido]-4-oxo-butyric acid;
(S)-2-Benzoylamino-4-dibenzofuran-2-yl-4-oxo-butyric acid
(S)-4-Dibenzofuran-2-yl-4-oxo-2-phenylacetylamino-butyric acid;
(S)-4-Dibenzofuran-2-yl-4-oxo-2-(3-phenyl-propionylamino)-butyric acid;
(S)-4-Dibenzofuran-2-yl-4-oxo-2-(7-phenyl-heptanoylamino)-butyric acid;
(S)-2-[(Biphenyl-4-carbonyl)-amino]-4-dibenzofuran-2-yl-4-oxo-butyric acid;
(S)-4-Dibenzofuran-2-yl-4-oxo-2-(dodecanoylamino)-butyric acid;
(S)-4-Dibenzofuran-2-yl-4-oxo-2-(dodecanoyl-amino)-butyric acid;
(S)-4-Dibenzofuran-2-yl-4-oxo-2-(2,2,2-trifluoroacetylamino)-butyric acid;
(R)-4-Dibenzofuran-2-yl-4-oxo-2-(2,2,2-trifluoroacetylamino)-butyric acid;
(S)-2-Amino-4-dibenzofuran-2-yl-4-oxo-butyric acid;
(S)-2-Acetylamino-4-dibenzofuran-2-yl-4-oxo-butyric acid;
(S)-4-Dibenzofuran-2-yl-2-[3-(2,6-diisopropyl-phenyl)-ureido]-4-oxo-butyric acid;
(S)-2-Benzoylamino-4-dibenzofuran-2-yl-4-oxo-butyric acid;
(S)-4-Dibenzofuran-2-yl-4-oxo-2-phenylacetylamino-butyric acid;
(S)-4-Dibenzofuran-2-yl-4-oxo-2-(3-phenyl-propionylamino)-butyric acid;
(S)-4-Dibenzofuran-2-yl-4-oxo-2-(7-phenyl-heptanoylamino)-butyric acid;
(S)-2-[(Biphenyl-4-carbonyl)-amino]-4-dibenzofuran-2-yl-4-oxo-butyric acid;
(S)-4-Dibenzofuran-2-yl-4-oxo-2-(octanoylamino)-butyric acid; and
(S)-4-Dibenzofuran-2-yl-4-oxo-2-(dodecanoylamino)-butyric acid.

Tricyclic sulfonamide matrix metalloproteinase inhibitors include compounds of the formula wherein M is a natural (L) alpha amino acid derivative having the structure X is O, S, S(O)ₙ, CH₂, CO, or NH;
R is a side chain of a natural alpha amino acid;
R¹ is $C_1$–$C_5$ alkoxy, hydroxy, or —NHOR⁵;
R² and R⁴ are independently hydrogen, —$C_1$–$C_5$ alkyl, —NO$_2$, halogen, —OR$^5$, —CN, —CO$_2$R$^5$, —SO$_3$R$^5$, —CHO, —COR$^5$, —CONR$^5$R$^6$, —(CH$_2$)$_n$NR$^5$R$^6$, —CF$_3$, or —NHCOR$^5$;

each R$^5$ and R$^6$ are independently hydrogen or C$_1$–C$_5$ alkyl; and n is 0 to 2, and the pharmaceutically acceptable salts, ester, amides, and prodrugs thereof.

Specific compounds from this class to be employed include:

(L)-2-(Dibenzofuran-2-sulfonylamino)-4-methyl-pentanoic acid;

(L)-2-(Dibenzofuran-2-sulfonylamino)-3-methyl-pentanoic acid (L)-2-(Dibenzofuran-2-sulfonylamino)-3-phenyl-propionic acid;

(L)-2-(Dibenzofuran-2-sulfonylamino)-propionic acid;

(L)-2-(Dibenzofuran-2-sulfonylamino)-3-methyl-butyric acid;

(Dibenzofuran-2-sulfonylamino)-acetic acid;

(L)-2-(Dibenzofuran-2-sulfonylamino)-succinic acid;

(L)-2-(Dibenzofuran-2-sulfonylamino)-3-tritylsulfanyl-propionic acid;

(L)-2-(Dibenzofuran-2-sulfonylamino)-3-mercapto-propionic acid;

(L)-2-(Dibenzofuran-2-sulfonylamino)-3-methyl-pentanoic acid hydroxyamide;

(L)-2-(Dibenzofuran-2-sulfonylamino)-4-methyl-pentanoic acid;

(L)-2-(Dibenzofuran-2-sulfonylamino)-3-methyl-pentanoic acid;

(L)-2-(Dibenzofuran-2-sulfonylamino)-3-phenyl-propionic acid;

(L)-2-(Dibenzofuran-2-sulfonylamino)-propionic acid;

(L)-2-(Dibenzofuran-2-sulfonylamino)-3-methyl-butyric acid;

(Dibenzofuran-2-sulfonylamino)-acetic acid;

(L)-2-(Dibenzofuran-2-sulfonylamino)-succinic acid;

(L)-2-(Dibenzofuran-2-sulfonylamino)-3-tritylsulfanyl-propionic acid;

(L)-2-(Dibenzofuran-2-sulfonylamino)-3-mercapto-propionic acid; and (L)-2-(Dibenzofuran-2-sulfonylamino)-3-methyl-pentanoic acid hydroxyamide.

Additional tricyclic sulfonamides are defined by the formula:

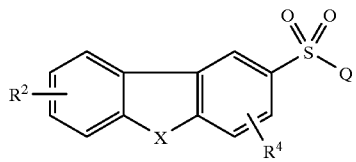

wherein Q is an un-natural amino acid;

X is O, S, S(O)$_n$, CH$_2$, CO, or NH;

R$^2$ and R$^4$ are independently hydrogen, C$_1$–C$_5$ alkyl, —NO$_2$, halogen, —OR$^5$, —CN, —CO$_2$R$^5$, —SO$_3$R$^5$, —CHO, —COR$^5$, —CONR$^5$R$^6$, (CH$_2$)$_n$NR$^5$R$^6$, —CF$_3$, or —NHCOR$^5$;

each R$^5$ and R$^6$ are independently hydrogen or C$_1$–C$_5$ alkyl; and n is 0 to 2, and the pharmaceutically acceptable salts, esters, amides, and prodrugs thereof.

Specific examples of such compounds include:

(S)-2-(Dibenzofuran-2-sulfonylamino)-4-phenyl-butyric acid;

2 (S)-3-[(Dibenzofuran-2-sulfonylamino)-methyl]-5-methyl-hexanoic acid;

(S)-2-(Dibenzofuran-2-sulfonylamino)-4-phenyl-butyric acid; and 2 (S)-3-[(Dibenzofuran-2-sulfonylamino)-methyl]-5-methyl-hexanoic acid.

Another general class of matrix metalloproteinase inhibitors, which are useful to treat and prevent heart failure and ventricular dilatation, are biphenyl butyric acid derivatives, including compounds of the formula:

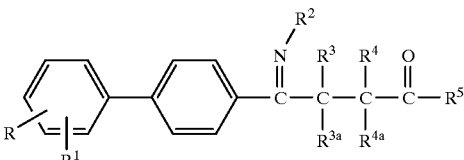

wherein R and R$^1$ are the same or different and are hydrogen, alkyl, halogen, nitro, cyano, trifluoromethyl, —OR$^6$ wherein R$^6$ is hydrogen, alkyl, aryl, arylalkyl, heteroaryl, or cycloalkyl,

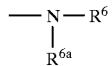

wherein R$^6$ and R$^{6a}$ are the same or different and are as defined above for R$^6$,

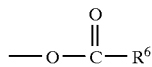

wherein R$^6$ is as defined above,

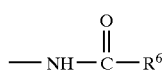

wherein R$^6$ is as defined above,

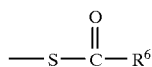

wherein R$^6$ is as defined above,

—SR$^6$ wherein R$^6$ is as defined above,

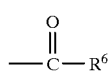

wherein R$^6$ is as defined above,

—CH$_2$—OR$^6$ wherein R$^6$ is as defined above,

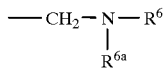

wherein R$^6$ and R$^{6a}$ are the same or different and are as defined above for R$^6$,

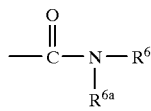

wherein R$^6$ and R$^{6a}$ are the same or different and are as defined above for R$^6$,

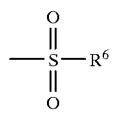

wherein R$^6$ is as defined above, cycloalkyl, or heteroaryl, with the proviso that R and R$^1$ are not both hydrogen;

R$^2$ is —OR$^6$ wherein R$^6$ is as defined above, or

wherein R$^6$ and R$^{6a}$ are the same or different and are as defined above for R$^6$;

R$^3$, R$^{3a}$, R$^4$, and R$^{4a}$ are the same or different and are hydrogen, fluorine, alkyl, —(CH$_2$)$_n$-aryl wherein n is an integer from 1 to 6, —(CH$_2$)$_n$-heteroaryl wherein n is as defined above, —(CH$_2$)$_n$-cycloalkyl wherein n is as defined above, —(CH$_2$)$_p$-X-(CH$_2$)$_q$-aryl wherein X is O, S, SO, SO$_2$, or NH, and p and q are each zero or an integer of 1 to 6, and the sum of p+q is not greater than six, —(CH$_2$)$_p$-X-(CH$_2$)$_q$-heteroaryl wherein X, p, and q are as defined above, or —(CH$_2$)$_n$-R$^7$ wherein R$^7$ is N-phthalimido, N-2,3-naphthyimido, —OR$^6$ wherein R$^6$ is as defined above,

wherein R$^6$ and R$^{6a}$ are the same or different and are as defined above for R$^6$, —SR$^6$ where R$^6$ is as defined above,

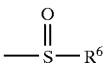

wherein R$^6$ is as defined above,

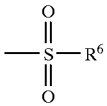

wherein R$^6$ is as defined above,

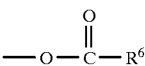

wherein R$^6$ is as defined above,

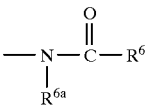

wherein R$^6$ and R$^{6a}$ are the same or different and are as defined above for R$^6$,

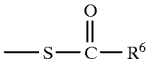

wherein R$^6$ is as defined above,

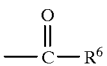

wherein R$^6$ is as defined above,

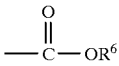

wherein R$^6$ is as defined above, or

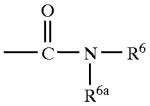

wherein R$^6$ and R$^{6a}$ are the same or different and are defined above for R$^6$, and n is as defined above;

R$^5$ is OH or SH; with the proviso that R$^3$, R$^{3a}$, R$^4$, and R$^{4a}$ are hydrogen; or at least one of R$^3$, R$^{3a}$, R$^4$, or R$^{4a}$ is fluorine; and corresponding isomers thereof; or a pharmaceutically acceptable salt thereof.

Typical compounds from this class that are routinely utilized to treat and prevent heart failure include:

4-(4'-Chloro-biphenyl-4-yl)-4-hydroxyimino-butyric acid;

4-(4'-Bromo-biphenyl-4-yl)-4-hydroxyimino-butyric acid;
4-(4'-Chloro-biphenyl-4-yl)-4-(dimethylhydrazono)-butyric acid;
4-(4'-Fluoro-biphenyl-4-yl)-4-hydroxyimino-butyric acid;
(±)-4-(4'-Chloro-biphenyl-4-yl)-4-hydroxy-butyric acid;
4-(4'-Bromo-2'-fluoro-biphenyl-4-yl)-4-hydroxyimino-butyric acid;
(±)-4-(4'-Chloro-biphenyl-4-yl)-3-fluoro-4-oxo-butyric acid;
4-(2',4'-Dichloro-biphenyl-4-yl)-4-hydroxyimino-butyric acid;
4-(2',4'-Difluoro-biphenyl-4-yl)-4-hydroxyimino-butyric acid;
(±)-4-(4'-Chloro-biphenyl-4-yl)-4-hydroxyimino-2-fluoro-2-(3-phenylpropyl)-butyric acid;
(±)-4-(4'-Chloro-biphenyl-4-yl)-4-hydroxyimino-2-fluoro-2-(2-phenylethyl)-butyric acid;
(±)-4-(4'-Chloro-biphenyl-4-yl)-4-hydroxyimino-2-fluoro-2-(3-phthalimidopropyl)-butyric acid;
(±)-4-(4'-Chloro-biphenyl-4-yl)-4-hydroxyimino-2-fluoro-2-(phenylthiomethyl)-butyric acid;
4-(4'-Chloro-2'-fluoro-biphenyl-4-yl)-4-hydroxyimino-butyric acid;
4-Hydroxyimino-4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxyimino-butyric acid;
(±)-4-(4'-Chloro-biphenyl-4-yl)-4-hydroxyimino-2-fluoro-2-(1H-indol-3-yl)methyl-butyric acid;
(±)-4-(4'-Chloro-biphenyl-4-yl)-4-hydroxyimino-2-fluoro-2-methyl-butyric acid;
(±)-2-[2-(4'-Chloro-biphenyl-4-yl)-2-hydroxyiminoethyl]-2-fluoro-6-phenyl-hexanoic acid;
(±)-4-(4'-Chloro-biphenyl-4-yl)-2-fluoro-2-[2-(1,3-dioxo-1,3-dihydro-benzo[F]isoindol-2-yl)-ethyl]-4-hydroxyimino-butyric acid;
(±)-2-[2-(4'-Chloro-biphenyl-4-yl)-2-hydroxyiminoethyl]-6-(1,3-dioxo-1,3-dihydro-isoindol-2-yl)-2-fluoro-hexanoic acid;
(±)-4-(4'-Chloro-biphenyl-4-yl)-4-hydroxyimino-2-fluoro-2-[2-(phenyl-ethylcarbamoyl)-ethyl]-butyric acid;
4-(4'-Chloro-biphenyl-4-yl)-3,3-difluoro-4-hydroxyimino-butyric acid;
(±)-4-(4'-Chloro-biphenyl-4-yl)-3,3-dimethyl-2-fluoro-4-hydroxyimino-butyric acid;
(±)-4-(4'-Chloro-biphenyl-4-yl)-2,2-dimethyl-3-fluoro-4-hydroxyimino-butyric acid;
4-(4'-Chloro-biphenyl-4-yl)-2,2-difluoro-4-hydroxyimino-butyric acid; and
4-(4'-Chloro-biphenyl-4-yl)-2,2,3,3-tetrafluoro-4-hydroxyimino-butyric acid.

A compound selected from the group consisting of:
4-(4'-Chloro-biphenyl-4-yl)-4-hydroxyimino-butyric acid;
4-(4'-Bromo-biphenyl-4-yl)-4-hydroxyimino-butyric acid;
4-(4'-Chloro-biphenyl-4-yl)-4-(dimethylhydrazono)-butyric acid;
4-(4'-Fluoro-biphenyl-4-yl)-4-hydroxyimino-butyric acid;
(±)-4-(4'-Chloro-biphenyl-4-yl)-4-hydroxy-butyric acid;
4-(4'-Bromo-2'-fluoro-biphenyl-4-yl)-4-hydroxyimino-butyric acid;
(±)-4-(4'-Chloro-biphenyl-4-yl)-3-fluoro-4-oxo-butyric acid;
4-(2',4'-Dichloro-biphenyl-4-yl)-4-hydroxyimino-butyric acid;
4-(2',4'-Difluoro-biphenyl-4-yl)-4-hydroxyimino-butyric acid;
(±)-4-(4'-Chloro-biphenyl-4-yl)-4-hydroxyimino-2-fluoro-2-(3-phenylpropyl)-butyric acid;
(±)-4-(4'-Chloro-biphenyl-4-yl)-4-hydroxyimino-2-fluoro-2-(2-phenylethyl)-butyric acid;
(±)-4-(4'-Chloro-biphenyl-4-yl)-4-hydroxyimino-2-fluoro-2-(3-phthalimidopropyl)-butyric acid;
(±)-4-(4'-Chloro-biphenyl-4-yl)-4-hydroxyimino-2-fluoro-2-(phenylthiomethyl)-butyric acid;
4-(4'-Chloro-2'-fluoro-biphenyl-4-yl)-4-hydroxyimino-butyric acid;
4-Hydroxyimino-4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxyimino-butyric acid;
(±)-4-(4'-Chloro-biphenyl-4-yl)-4-hydroxyimino-2-fluoro-2-(1H-indol-3-yl)methyl-butyric acid;
(±)-4-(4'-Chloro-biphenyl-4-yl)-4-hydroxyimino-2-fluoro-2-methyl-butyric acid;
(±)-2-[2-(4'-Chloro-biphenyl-4-yl)-2-hydroxyiminoethyl]-2-fluoro-6-phenyl-hexanoic acid;
(±)-4-(4'-Chloro-biphenyl-4-yl)-2-fluoro-2-[2-(1,3-dioxo-1,3-dihydro-benzo[F]isoindol-2-yl)-ethyl]-4-hydroxyimino-butyric acid;
(±)-2-[2-(4'-Chloro-biphenyl-4-yl)-2-hydroxyiminoethyl]-6-(1,3-dioxo-1,3-dihydro-isoindol-2-yl)-2-fluoro-hexanoic acid;
(±)-4-(4'-Chloro-biphenyl-4-yl)-4-hydroxyimino-2-fluoro-2-[2-(phenyl-ethylcarbamoyl)-ethyl]-butyric acid;
4-(4'-Chloro-biphenyl-4-yl)-3,3-difluoro-4-hydroxyimino-butyric acid;
(±)-4-(4'-Chloro-biphenyl-4-yl)-3,3-dimethyl-2-fluoro-4-hydroxyimino-butyric acid;
(±)-4-(4'-Chloro-biphenyl-4-yl)-2,2-dimethyl-3-fluoro-4-hydroxyimino-butyric acid;
4-(4'-Chloro-biphenyl-4-yl)-2,2-difluoro-4-hydroxyimino-butyric acid; and
4-(4'-Chloro-biphenyl-4-yl)-2,2,3,3-tetrafluoro-4-hydroxyimino-butyric acid.

Biphenyl sulfonamides are also particularly good in the present method. Such compounds include those of the formula:

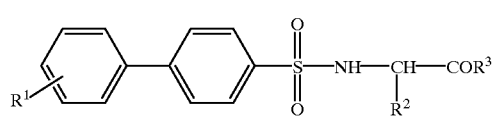

wherein:
$R^1$ is $C_1$–$C_6$ alkyl, halo, nitro, $NR^4R^5$, cyano, $OR^4$, and $COOR^4$;
$R^2$ is $C_1$–$C_6$ alkyl, optionally substituted by phenyl, substituted phenyl, $NR^4R^5$, $OR^6$, carboxy, carboxamido,

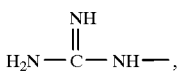

thio, methylthio, indole, imidazole, phthalimido, phenyl, and substituted phenyl;

$R^3$ is OH, $OC_1-C_6$ alkyl, or NHOH;

$R^4$ is hydrogen, $C_1-C_6$ alkyl, or $C_1-C_6$ alkanoyl;

$R^5$ is hydrogen or $C_1-C_6$ alkyl; and $R^6$ is hydrogen, $C_1-C_6$ alkyl, $C_1-C_6$ alkanoyl, phenyl, or substituted phenyl.

Specific compounds which can be employed include a compound of the above formula wherein $R^1$ is at the 4' position.

Another class of matrix metalloproteinase inhibitors useful in the present method are the heterocyclic substituted phenyl butyric acid derivatives, for example those defined by the formula:

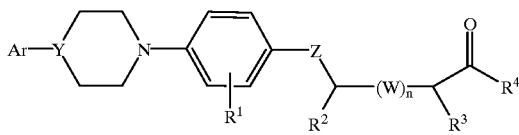

Ar is selected from phenyl,
phenyl substituted with
alkyl,
$NO_2$,
halogen,
$OR^5$ wherein $R^5$ is hydrogen or alkyl,
CN,
$CO_2R^5$ wherein $R^5$ is as defined above,
$SO_3R^5$ wherein $R^5$ is as defined above,
CHO,
$COR^5$ wherein $R^5$ is as defined above,
$CONHR^5$ wherein $R^5$ is as defined above, or
$CONHCOR^5$ wherein $R^5$ is as defined above,
2-naphthyl, or
heteroaryl;

$R^1$ is selected from hydrogen,
methyl,
ethyl,
$NO_2$,
halogen,
$OR^5$ wherein $R^5$ is as defined above,
CN,
$CO_2R^5$ wherein $R^5$ is as defined above,
$SO_3R^5$ wherein $R^5$ is as defined above,
CHO, or
$COR^5$ wherein $R^5$ is as defined above;

$R^2$ and $R^3$ are the same or different and independently selected from hydrogen,
alkyl,
—$(CH_2)_v$-aryl wherein v is an integer from 1 to 5,
—$(CH_2)_v$-heteroaryl wherein v is as defined above,
—$(CH_2)_v$-cycloalkyl wherein v is as defined above,
—$(CH_2)_p$-X-$(CH_2)_q$-aryl wherein X is O or S and p and q is each zero or an integer of 1 to 5, and the sum of p+q is not greater than an integer of 5,
—$(CH_2)_p$-X-$(CH_2)_q$-heteroaryl wherein X, p, and q are as defined above,
—$(CH_2)_t NR^6 R^{6a}$, wherein t is zero or an integer of from 1 to 9 and $R^6$ and $R^{6a}$ are each the same or different and are as defined above for $R^5$,
—$(CH_2)_v SR^5$, wherein v and $R^5$ are as defined above,
—$(CH_2)_v CO_2 R^5$, wherein v and $R^5$ are as defined above, or
—$(CH_2)_v CONR^6 R^{6a}$, wherein $R^6$ and $R^{6a}$ are the same or different and are as defined above for $R^5$ and v is as defined above;

$R^3$ is additionally —$(CH_2)_r R^7$ wherein r is an integer from 1 to 5 and $R^7$ is 1,3-dihydro-1,3-dioxo-2H-isoindol-2-yl, or 1,3,-dihydro-1,3-dioxo-benzo[f]isoindol-2-yl;

Y is CH or N;

Z is

wherein $R^{10}$ is as defined above for $R^2$ and $R^3$, and is independently the same or different from $R^2$ and $R^3$ provided that when Z is

then $R^4$ must be OH,

C=O,

C=$NOR^5$ wherein $R^5$ is as defined above, or

C=N—$NR^6 R^{6a}$ wherein $R^6$ and $R^{6a}$ are the same or different and are as defined above for $R^5$;

W is —$CHR^5$ wherein $R^5$ is as defined above;

n is zero or an integer of 1;

$R^4$ is OH, $NR^6 R^{6a}$ wherein $R^6$ and $R^{6a}$ are the same or different and are as defined above for $R^5$, when $R^4$ is $NR^6 R^{6a}$ then Z must be C=O or $NHOR^9$ wherein $R^9$ is hydrogen, alkyl, or benzyl;

and corresponding isomers thereof; or a pharmaceutically acceptable salt thereof.

Especially preferred MMP inhibitors have the formula

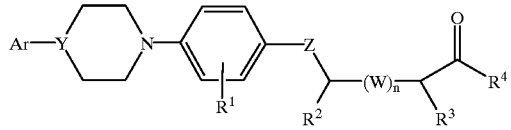

Ar is selected from phenyl,
phenyl substituted with
alkyl,
$NO_2$,
halogen,
$OR^5$ wherein $R^5$ is hydrogen or alkyl,
CN,
$CO_2R^5$ wherein $R^5$ is as defined above,
$SO_3R^5$ wherein $R^5$ is as defined above,
CHO,
$COR^5$ wherein $R^5$ is as defined above, CONHR⁵ wherein R⁵ is as defined above, or
NHCOR⁵ wherein R⁵ is as defined above,
2-naphthyl, or
heteroaryl;
R¹ is selected from hydrogen,
methyl,
ethyl,
NO₂,
halogen,
OR⁵ wherein R⁵ is as defined above,
CN,
CO₂R⁵ wherein R⁵ is as defined above,
SO₃R⁵ wherein R⁵ is as defined above,
CHO, or
COR⁵ wherein R⁵ is as defined above;
R² and R³ are the same or different and independently selected from hydrogen,
alkyl,
—(CH₂)ᵥ-aryl wherein v is an integer from 1 to 5,
—(CH₂)ᵥ-heteroaryl wherein v is as defined above,
—(CH₂)ᵥ-cycloalkyl wherein v is as defined above,
—(CH₂)ₚ-X-(CH₂)q-aryl wherein X is O or S and p and q is each zero or an integer of 1 to 5, and the sum of p+q is not greater than an integer of 5,
—(CH₂)ₚ-X-(CH₂)q-heteroaryl wherein X, p, and q are as defined above,
—(CH₂)ₜNR⁶R⁶ᵃ, wherein t is zero or an integer of from 1 to 9 and R⁶ and R⁶ᵃ are each the same or different and are as defined above for R⁵,
—(CH₂)ᵥSR⁵, wherein v and R⁵ are as defined above,
—(CH₂)ᵥCO₂R⁵, wherein v and R⁵ are as defined above, or
—(CH₂)ᵥCONR⁶R⁶ᵃ, wherein R⁶ and R⁶ᵃ are the same or different and are as defined above for R⁵ and v is as defined above;
R³ is additionally —(CH₂)ᵣR⁷ wherein r is an integer from 1 to 5 and R⁷ is 1,3-dihydro-1,3-dioxo-2H-isoindol-2-yl, or 1,3,-dihydro-1,3-dioxo-benzo[f]isoindol-2-yl;
Y is CH or N;
Z is

wherein R¹⁰ is as defined above for R² and R³, and is independently the same or different from R² and R³ provided that when Z is

then R⁴ must be OH,
C=O,
C=NOR⁵ wherein R⁵ is as defined above, or
C=N—NR⁶R⁶ᵃ wherein R⁶ and R⁶ᵃ are the same or different and are as defined above for R⁵;
W is —CHR⁵ wherein R⁵ is as defined above;
n is zero or an integer of 1;
R⁴ is OH,
NR⁶R⁶ᵃ wherein R⁶ and R⁶ᵃ are the same or different and are as defined above for R⁵, when R⁴ is NR⁶R⁶ᵃ then Z must be C=O or
NHOR⁹ wherein R⁹ is hydrogen, alkyl, or benzyl;
and corresponding isomers thereof; or a pharmaceutically acceptable salt thereof.

Preferred compounds to be employed include:
4-Oxo-4-[4-(4-phenyl-piperidin-1-yl)-phenyl]-butyric acid;
4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxyimino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazin-1-yl)-phenyl]-butyric acid;
(±)3-Methyl-5-oxo-5-[4-(4-phenyl-piperidin-1-yl)-phenyl]-pentanoic acid;
4-Oxo-4-[4-(4-phenyl-piperidin-1-yl)-phenyl]-butyric acid;
4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxyimino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazin-1-yl)-phenyl]-butyric acid; and
(±)3-Methyl-5-oxo-5-[4-(4-phenyl-piperidin-1-yl)-phenyl]-pentanoic acid.

A compound which is 4-oxo-4-[4-(4-phenyl-piperidin-1-yl)-phenyl]-butyric acid.

Similar compounds which are sulfonamide derivatives have the formula:

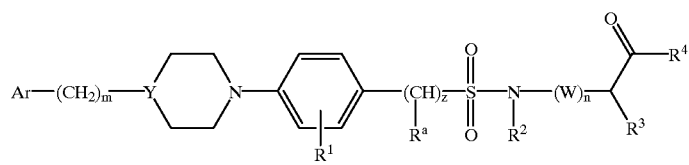

wherein:

Ar is selected from phenyl;

phenyl substituted with alkyl, —$NO_2$, halogen, —$OR^5$, —CN, —$CO_2R^5$, —$SO_2R^5$, —CHO, —$COR^5$, —$CONHR^5$, —$NHR^5$, or —$NHCOR^5$;

heteroaryl; or 2-naphthyl;

$R^1$ is hydrogen, methyl, —$NO_2$, —Cl, —$NH_2$, —$NHCO_2CH_3$, —OH, or —$CO_2H$;

$R^2$ and $R^3$ are the same or different and are independently selected from hydrogen, alkyl, —$(CH_2)_v$-aryl, —$(CH_2)_v$-heteroaryl, —$(CH_2)_v$-cycloalkyl, —$(CH_2)_p$-X-$(CH_2)_q$-aryl, —$(CH_2)_p$-X-$(CH_2)_q$-heteroaryl, —$(CH_2)_t NR^6R^{6a}$, —$(CH_2)_v R^7$, —$(CH_2)_v CO_2R^5$, —$(CH_2)_v CONR^6R^{6a}$, or —$(CH_2)_v SR^5$;

m is zero or 1;

Y is CH or N; provided that when m=1, Y does not =N;

z is zero or 1;

z is zero or 1;

W is —$CHR^8$;

n is zero or 1;

$R^4$ is —OH, —$NR^6R^{6a}$, or —$NHOR^9$;

$R^5$ is hydrogen or alkyl;

v is 1 to 5;

X is O or S;

p and q are independently 1 to 5, provided that p+q is not greater than 5;

t is 1 to 9;

$R^6$ and $R^{6a}$ are each the same or different and are hydrogen or alkyl;

$R^7$ is 1,3-dihydro-1,3-dioxo-2H-isoindol-2-yl, or 1,3-dihydro-1,3-dioxo-benzo[f]isoindol-2-yl;

$R^8$ is hydrogen or alkyl; and $R^9$ is hydrogen, alkyl, or benzyl; or a pharmaceutically acceptable salt thereof.

Specific sulfonamide derivatives to be employed in the present method include:

[4-(4-Phenyl-piperidin-1-yl)-benzenesulfonylamino]-acetic acid;

N-Hydroxy-2-[4-(4-phenyl-piperidin-1-yl)-benzenesulfonylamino]-acetamide;

3-[4-(4-Phenyl-piperidin-1-yl)-benzenesulfonylamino]-propionic acid;

(R)-4-Methyl-2-[4-(4-phenyl-piperidin-1-yl)-benzenesulfonylamino]-pentanoic acid;

(S)-4-Methyl-2-[4-(4-phenyl-piperidin-1-yl)-benzenesulfonylamino]-pentanoic acid;

(S)-3-Phenyl-2-[4-(4-phenyl-piperidin-1-yl)-benzenesulfonylamino]-propionic acid;

(R)-3-Phenyl-2-[4-(4-phenyl-piperidin-1-yl)-benzenesulfonylamino]-propionic acid;

(S)-3-(1H-Indol-3-yl)-2-[4-(4-phenyl-piperidin-1-yl)-benzenesulfonylamino]-propionic acid;

(±)-5-Phenyl-2-[4-(4-phenyl-piperidin-1-yl)-benzenesulfonylamino]-pentanoic acid;

[4-(4-Phenyl-piperazin-1-yl)-benzene-sulfonylamino]-acetic acid;

{Isobutyl-[4-(4-phenyl-piperidin-1-yl)-benzene sulfonyl]amino}-acetic acid;

(S)-4-Phenyl-2-[4-(4-phenyl-piperidin-1-yl)-benzenesulfonylamino]-butyric acid;

(R)-2-[4-(4-Phenyl-piperidin-1-yl)-benzene-sulfonylamino]-3-tritylsulfanyl-propionic acid, sodium salt;

(R)-3-(1H-Indol-3-yl)-2-[4-(4-phenyl-piperidin-1-yl)-benzenesulfonylamino]-propionic acid, disodium salt, monohydrate;

(S)-2-{4-[-4-(4-Hydroxy-phenyl)-piperazin-1-yl]-benzenesulfonylamino}-3-phenyl-propionic acid;

(S)-2-{4-[-4-(4-Chloro-phenyl)-piperazin-1-yl]-benzenesulfonylamino}-3-phenyl-propionic acid, hydrochloride;

(R)-3-Mercapto-2-[4-(4-phenyl-piperidin-1-yl)-benzenesulfonylamino]-propionic acid, trifluoracetic acid salt;

(S)-2-[4-(4-Benzyl-piperidin-1-yl)-benzene-sulfonylamino]-3-phenyl-propionic acid;

(S)-3-(4-Benzyloxy-phenyl)-2-[4-(4-phenyl-piperidin-1-yl)-benzenesulfonylamino]-propionic acid;

(S)-3-(4-Hydroxy-phenyl)-2-[4-(4-phenyl-piperidin-1-yl)-benzenesulfonylamino]-propionic acid;

(S)-3-Phenyl-2-[4-(4-phenyl-piperazin-1-yl)-benzenesulfonylamino]-propionic acid;

(S)-2-{4-[-4-(3-Methoxy-phenyl)-piperazin-1-yl]-benzenesulfonylamino}-3-phenyl-propionic acid;

(S)-2-{4-[-4-(3-Hydroxy-phenyl)-piperazin-1-yl]-benzenesulfonylamino}-3-phenyl-propionic acid hydrobromide;

(S)-2-{4-[-4-(4-Methoxy-phenyl)-piperazin-1-yl]-benzenesulfonylamino}-3-phenyl-propionic acid;

(R)-4-Methyl-2-[4-(4-phenyl-piperidin-1-yl)-benzenesulfonylamino]-pentanoic acid;

(S)-4-Methyl-2-[4-(4-phenyl-piperidin-1-yl)-benzenesulfonylamino]-pentanoic acid;

(S)-3-Phenyl-2-[4-(4-phenyl-piperidin-1-yl)-benzenesulfonylamino]-propionic acid;

(R)-3-Phenyl-2-[4-(4-phenyl-piperidin-1-yl)-benzenesulfonylamino]-propionic acid;

(S)-3-(1H-Indol-3-yl)-2-[4-(4-phenyl-piperidin-1-yl)-benzenesulfonylamino]-propionic acid;

[4-(4-Phenyl-piperidin-1-yl)-benzenesulfonylamino]-acetic acid;

N-Hydroxy-2-[4-(4-phenyl-piperidin-1-yl)-benzenesulfonylamino]-acetamide;

3-[4-(4-Phenyl-piperidin-1-yl)-benzenesulfonylamino]-propionic acid;

(R)-4-Methyl-2-[4-(4-phenyl-piperidin-1-yl)-benzenesulfonylamino]-pentanoic acid;

(S)-4-Methyl-2-[4-(4-phenyl-piperidin-1-yl)-benzenesulfonylamino]-pentanoic acid;

(S)-3-Phenyl-2-[4-(4-phenyl-piperidin-1-yl)-benzenesulfonylamino]-propionic acid;

(R)-3-Phenyl-2-[4-(4-phenyl-piperidin-1-yl)-benzenesulfonylamino]-propionic acid;

(S)-3-(1H-Indol-3-yl)-2-[4-(4-phenyl-piperidin-1-yl)-benzenesulfonylamino]-propionic acid;

(±)-5-Phenyl-2-[4-(4-phenyl-piperidin-1-yl)-benzenesulfonylamino]-pentanoic acid;

[4-(4-Phenyl-piperazin-1-yl)-benzene-sulfonylamino]-acetic acid;

{Isobutyl-[4-(4-phenyl-piperidin-1-yl)-benzene sulfonyl]amino}-acetic acid;

(S)-4-Phenyl-2-[4-(4-phenyl-piperidin-1-yl)-benzenesulfonylamino]-butyric acid;

(R)-2-[4-(4-Phenyl-piperidin-1-yl)-benzene-sulfonylamino]-3-tritylsulfanyl-propionic acid, sodium salt;

(R)-3-(1H-Indol-3-yl)-2-[4-(4-phenyl-piperidin-1-yl)-benzenesulfonylamino]-propionic acid, disodium salt, monohydrate;

(S)-2-{4-[-4-(4-Hydroxy-phenyl)-piperazin-1-yl]-benzenesulfonylamino}-3-phenyl-propionic acid;

(S)-2-{4-[-4-(4-Chloro-phenyl)-piperazin-1-yl]-benzenesulfonylamino}-3-phenyl-propionic acid, hydrochloride;

(R)-3-Mercapto-2-[4-(4-phenyl-piperidin-1-yl)-benzenesulfonylamino]-propionic acid, trifluoracetic acid salt;
(S)-2-[4-(4-Benzyl-piperidin-1-yl)-benzenesulfonylamino]-3-phenyl-propionic acid;
(S)-3-(4-Benzyloxy-phenyl)-2-[4-(4-phenyl-piperidin-1-yl)-benzenesulfonylamino]-propionic acid;
(S)-3-(4-Hydroxy-phenyl)-2-[4-(4-phenyl-piperidin-1-yl)-benzenesulfonylamino]-propionic acid;
(S)-3-Phenyl-2-[4-(4-phenyl-piperazin-1-yl)-benzenesulfonylamino]-propionic acid;
(S)-2-{4-[-4-(3-Methoxy-phenyl)-piperazin-1-yl]-benzenesulfonylamino}-3-phenyl-propionic acid;
(S)-2-{4-[-4-(3-Hydroxy-phenyl)-piperazin-1-yl]-benzenesulfonylamino}-3-phenyl-propionic acid hydrobromide;
(S)-2-{4-[-4-(4-Methoxy-phenyl)-piperazin-1-yl]-benzenesulfonylamino}-3-phenyl-propionic acid;
(R)-4-Methyl-2-[4-(4-phenyl-piperidin-1-yl)-benzenesulfonylamino]-pentanoic acid;
(S)-4-Methyl-2-[4-(4-phenyl-piperidin-1-yl)-benzenesulfonylamino]-pentanoic acid;
(S)-3-Phenyl-2-[4-(4-phenyl-piperidin-1-yl)-benzenesulfonylamino]-propionic acid;
(R)-3-Phenyl-2-[4-(4-phenyl-piperidin-1-yl)-benzenesulfonylamino]-propionic acid; and
(S)-3-(1H-Indol-3-yl)-2-[4-(4-phenyl-piperidin-1-yl)-benzenesulfonylamino]-propionic acid.

Additional specific compounds which can be used include:

2-(Dibenzofuran-2-sulfonylamino)-3-(4-fluoro-phenyl)-propionic acid;
2-(Dibenzofuran-2-sulfonylamino)-3-phenyl-propionic acid;
3-(4-tert-Butoxy-phenyl)-2-(dibenzofuran-2-sulfonylamino)-propionic acid;
(Dibenzofuran-2-sulfonylamino)-phenyl-acetic acid;
3-tert-Butoxy-2-(dibenzofuran-2-sulfonylamino)-propionic acid;
2-(Dibenzofuran-2-sulfonylamino)-3-(1H-imidazol-4-yl)-propionic acid;
2-(Dibenzofuran-2-sulfonylamino)-3-hydroxy-propionic acid;
3-Benzyloxy-2-(dibenzofuran-2-sulfonylamino)-propionic acid;
6-Benzyloxycarbonylamino-2-(dibenzofuran-2-sulfonylamino)-hexanoic acid;
5-Benzyloxycarbonylamino-2-(dibenzofuran-2-sulfonylamino)-pentanoic acid;
(Dibenzofuran-2-sulfonylamino)-(4-methoxy-phenyl)-acetic acid;
3-Chloro-2-(dibenzofuran-2-sulfonylamino)-propionic acid;
3-(4-Benzyloxy-phenyl)-2-(dibenzofuran-2-sulfonylamino)-propionic acid;
2-(Dibenzofuran-2-sulfonylamino)-5-p-tolyl-sulfanylamino-pentanoic acid;
2-(Dibenzofuran-2-sulfonylamino)-4-mercapto-butyric acid;
3-(4-Bromo-phenyl)-2-(dibenzofuran-2-sulfonyl-amino)-propionic acid;
2-(Dibenzofuran-2-sulfonylamino)-butyric acid;
1-(Dibenzofuran-2-sulfonylamino)-cyclopropane-carboxylic acid;
3-(4-Chloro-phenyl)-2-(dibenzofuran-2-sulfonyl-amino)-propionic acid;
2-(Dibenzofuran-2-sulfonylamino)-3-(1H-indol-3-yl)-propionic acid;
2-(4'-Bromo-biphenyl-4-sulfonylamino)-6-(4-fluoro-benzenesulfonylamino)-hexanoic-acid;
2-(4'-Bromo-biphenyl-4-sulfonylamino)-6-(4-methoxy-benzenesulfonylamino)-hexanoic acid;
6-(4-Bromo-benzenesulfonylamino)-2-(4'-bromo-biphenyl-4-sulfonylamino)-hexanoic-acid;
6-(2-Acetylamino-thiazole-5-sulfonylamino)-2-(4'-bromo-biphenyl-4-sulfonylamino)-hexanoic-acid;
6-(4-Acetylamino-benzenesulfonylamino)-2-(4'-bromo-biphenyl-4-sulfonylamino)-hexanoic-acid;
6-Benzenesulfonylamino-2-(4'-bromo-biphenyl-4-sulfonylamino)-hexanoic acid;
2-(4'-Bromo-biphenyl-4-sulfonylamino)-6-(pentane-1-sulfonylamino)-hexanoic acid;
2-(4'-Bromo-biphenyl-4-sulfonylamino)-6-(naphthalene-2-sulfonylamino)-hexanoic-acid;
2-(4'-Bromo-biphenyl-4-sulfonylamino)-6-(naphthalene-1-sulfonylamino)-hexanoic-acid;
2-(4'-Bromo-biphenyl-4-sulfonylamino)-6-(2-phenyl-ethenesulfonylamino)-hexanoic-acid;
2-(4'-Bromo-biphenyl-4-sulfonylamino)-6-phenyl-acetylamino-hexanoic acid;
2-(4'-Bromo-biphenyl-4-sulfonylamino)-6-[2-(4-chloro-phenoxy)-acetylamino]-hexanoic acid;
2-(4'-Bromo-biphenyl-4-sulfonylamino)-6-[2-(4-chloro-phenoxy)-2-methyl-propionylamino]-hexanoic acid;
2-(4'-Bromo-biphenyl-4-sulfonylamino)-6-[2-(pyridin-4-ylsulfanyl)-acetylamino]-hexanoic acid;
2-(4'-Bromo-biphenyl-4-sulfonylamino)-6-[2-(2,4-dichloro-phenoxy)-acetylamino]-hexanoic acid;
2-(4'-Bromo-biphenyl-4-sulfonylamino)-6-(2-thiophen-2-yl-acetylamino)-hexanoic acid;
2-(4'-Bromo-biphenyl-4-sulfonylamino)-6-(3-phenyl-acryloylamino)-hexanoic acid;
2-(4'-Bromo-biphenyl-4-sulfonylamino)-6-(7-phenyl-heptanoylamino)-hexanoic acid;
2-(4'-Bromo-biphenyl-4-sulfonylamino)-6-[2-(2-trifluoromethyl-phenyl)-acetylamino]-hexanoic acid;
2-(4'-Bromo-biphenyl-4-sulfonylamino)-6-(2-phenoxy-butyrylamino)-hexanoic acid;
2-(4'-Bromo-biphenyl-4-sulfonylamino)-6-(2-phenyl-sulfanyl-acetylamino)-hexanoic acid;
2-(4'-Bromo-biphenyl-4-sulfonylamino)-6-(2-phenoxy-acetylamino)-hexanoic acid;
2-(4'-Bromo-biphenyl-4-sulfonylamino)-6-[2-(3,4-dimethoxy-phenyl)-acetylamino]-hexanoic acid;
2-(4'-Bromo-biphenyl-4-sulfonylamino)-6-[2-(4-tert-butyl-phenoxy)-acetylamino]-hexanoic acid;
2-(4'-Bromo-biphenyl-4-sulfonylamino)-6-[3-(3,4-dimethoxy-phenyl)-propionylamino]-hexanoic acid;
2-(4'-Bromo-biphenyl-4-sulfonylamino)-6-(2-cyclopent-1-enyl-acetylamino)-hexanoic acid;
2-(4'-Bromo-biphenyl-4-sulfonylamino)-6-[2-(4-methoxy-phenoxy)-acetylamino]-hexanoic acid;
2-(4'-Bromo-biphenyl-4-sulfonylamino)-6-[2-(naphthalen-1-yloxy)-acetylamino]-hexanoic acid;
2-(4'-Bromo-biphenyl-4-sulfonylamino)-6-[2-(4-nitro-phenoxy)-acetylamino]-hexanoic acid;
2-(4'-Bromo-biphenyl-4-sulfonylamino)-6-[4-(4-chloro-3-methyl-phenoxy)-butyrylamino]-hexanoic acid;
2-(4'-Bromo-biphenyl-4-sulfonylamino)-6-[3-(4-methoxy-phenyl)-propionylamino]-hexanoic acid;
2-(4'-Bromo-biphenyl-4-sulfonylamino)-6-(2-pyridin-3-yl-acetylamino)-hexanoic acid;
6-(2-Benzo[1,3]dioxol-5-yl-acetylamino)-2-(4'-bromo-biphenyl-4-sulfonylamino)-hexanoic acid;
2-(4'-Bromo-biphenyl-4-sulfonylamino)-6-(2-pyridin-2-yl-acetylamino)-hexanoic acid;

2-(4'-Bromo-biphenyl-4-sulfonylamino)-6-[2-(4-tert-butyl-phenoxy)-acetylamino]-hexanoic acid;

2-(4'-Bromo-biphenyl-4-sulfonylamino)-6-[3-(3,4-dimethoxy-phenyl)-propionylamino]-hexanoic acid;

2-(4'-Bromo-biphenyl-4-sulfonylamino)-6-(2-cyclopent-1-enyl-acetylamino)-hexanoic acid;

2-(4'-Bromo-biphenyl-4-sulfonylamino)-6-[2-(4-methoxy-phenoxy)-acetylamino]-hexanoic acid;

2-(4'-Bromo-biphenyl-4-sulfonylamino)-6-[2-(naphthalen-1-yloxy)-acetylamino]-hexanoic acid;

2-(4'-Bromo-biphenyl-4-sulfonylamino)-6-[2-(4-nitro-phenoxy)-acetylamino]-hexanoic acid;

2-(4'-Bromo-biphenyl-4-sulfonylamino)-6-[4-(4-chloro-3-methyl-phenoxy)-butyrylamino]-hexanoic acid;

2-(4'-Bromo-biphenyl-4-sulfonylamino)-6-[3-(4-methoxy-phenyl)-propionylamino]-hexanoic acid;

2-(4'-Bromo-biphenyl-4-sulfonylamino)-6-(2-pyridin-3-yl-acetylamino)-hexanoic acid;

6-(2-Benzo[1,3]dioxol-5-yl-acetylamino)-2-(4'-bromo-biphenyl-4-sulfonylamino)-hexanoic acid;

2-(4'-Bromo-biphenyl-4-sulfonylamino)-6-(2-pyridin-2-yl-acetylamino)-hexanoic acid;

2-(4'-Bromo-biphenyl-4-sulfonylamino)-6-[4-(4-nitro-phenyl)-butyrylamino]-hexanoic acid;

2-(4'-Bromo-biphenyl-4-sulfonylamino)-6-[2-(4-tert-butyl-phenoxy)-acetylamino]-hexanoic acid;

2-(4'-Bromo-biphenyl-4-sulfonylamino)-6-[3-(3,4-dimethoxy-phenyl)-propionylamino]-hexanoic acid;

2-(4'-Bromo-biphenyl-4-sulfonylamino)-6-(2-cyclopent-1-enyl-acetylamino)-hexanoic acid;

2-(4'-Bromo-biphenyl-4-sulfonylamino)-6-[2-(4-methoxy-phenoxy)-acetylamino]-hexanoic acid;

2-(4'-Bromo-biphenyl-4-sulfonylamino)-6-(4-phenyl-butyrylamino)-hexanoic acid;

2-(4'-Bromo-biphenyl-4-sulfonylamino)-6-[4-(4-chloro-3-methyl-phenoxy)-butyrylamino]-hexanoic acid;

2-(4'-Bromo-biphenyl-4-sulfonylamino)-6-[3-(4-chloro-phenyl)-propionylamino]-hexanoic acid;

2-(4'-Bromo-biphenyl-4-sulfonylamino)-6-[3-(4-methoxy-phenyl)-propionylamino]-hexanoic acid;

2-(4'-Bromo-biphenyl-4-sulfonylamino)-6-(2-pyridin-3-yl-acetylamino)-hexanoic acid;

6-(2-Benzo[1,3]dioxol-5-yl-acetylamino)-2-(4'-bromo-biphenyl-4-sulfonylamino)-hexanoic acid;

2-(4'-Bromo-biphenyl-4-sulfonylamino)-6-(2-naphthalen-1-yl-acetylamino)-hexanoic acid;

2-(4'-Bromo-biphenyl-4-sulfonylamino)-6-[3-(4-chloro-phenoxy)-propionylamino]-hexanoic acid;

2-(4'-Bromo-biphenyl-4-sulfonylamino)-6-(6-phenyl-hexanoylamino)-hexanoic acid;

2-(4'-Bromo-biphenyl-4-sulfonylamino)-6-(4-thiophen-2-yl-butyrylamino)-hexanoic acid;

2-(4'-Bromo-biphenyl-4-sulfonylamino)-6-(2,4,6-triisopropyl-benzoylamino)-hexanoic acid;

2-(4'-Bromo-biphenyl-4-sulfonylamino)-6-isobutoxycarbonylamino-hexanoic acid;

2-(4'-Bromo-biphenyl-4-sulfonylamino)-6-(9H-fluoren-9-ylmethoxycarbonylamino)-hexanoic acid;

6-(Adamantan-1-yloxycarbonylamino)-2-(4'-bromo-biphenyl-4-sulfonylamino)-hexanoic acid; and 6-Allyloxycarbonylamino-2-(4'-bromo-biphenyl-4-sulfonylamino)-hexanoic acid.

Numerous succinamide MMP inhibitors are known and can be utilized in the method of this invention. Typical succinamides include:

2S,$N^1$-Dihydroxy-3R-isobutyl-$N^4$-{1S-[2-(2-methoxy-ethoxymethoxy)ethylcarbamoyl]-2,2-dimethyl-propyl}-succinamide;

2S-Allyl-$N^1$-hydroxy-3R-isobutyl-$N^4$-{1S-[2-(2-methoxy-ethoxymethoxy)ethylcarbamoyl]-2-phenyl-ethyl}-succinamide;

2S-Allyl-$N^1$-hydroxy-3R-isobutyl-$N^4$-{1S-[2-(2-methoxy-ethoxymethoxy)ethylcarbamoyl]-2,2-dimethyl-propyl}-succinamide;

2S-Allyl-$N^1$-hydroxy-3R-isobutyl-$N^4$-(1S-{2-[2-(2-methoxy-ethoxy)-ethoxy]-ethylcarbamoyl}-2,2-dimethyl-propyl}-succinamide;

2S-Allyl-$N^4$-{1S-[2,2-di-(methoxymethyl)-propylcarbamoyl}-2,2-dimethyl-propyl]-$N^1$-hydroxy-3R-isobutyl-succinamide;

2S-Allyl-$N^4$-{1S-[2,2-di-(methoxymethyl)-butylcarbamoyl]-2,2-dimethyl-propyl}-$N^1$-hydroxy-3R-isobutyl-succinamide;

$N^4$-Hydroxy-2R-isobutyl-$N^1$-{1S-[2-(2-methoxyethoxy)-ethylcarbamoyl]-2,2-dimethyl-propyl}-3S-(thiophen-2-yl-sulfanylmethyl)-succinamide;

$N^4$-Hydroxy-2R-isobutyl-$N^1$- (1S-{2-[2-(2-methoxyethoxy)-ethoxy]-ethylcarbamoyl}-2,2-dimethyl-propyl)-3S-(thiophen-2-yl-sulfanylmethyl)-succinamide;

$N^1$-{1S-[2,2-Di-(methoxymethyl)-propylcarbamoyl]-2,2-dimethyl-propyl}-$N^4$-hydroxy-3R-isobutyl-3S-(thiophen-2-yl-sulfanylmethyl)-succinamide;

$N^4$-Hydroxy-2R-isobutyl-$N^1$-{1S-[2-(2-methoxyethoxy)-ethylcarbamoyl]-2,2-dimethyl-propyl}-3S-propyl-succinamide;

$N^4$-(1S-Cyclobutylcarbamoyl-2,2-dimethyl-propyl)-2S,$N^1$-dihydroxy-3R-isobutyl-succinamide;

$N^4$-(1S-Cyclopropylcarbamoyl-2,2-dimethyl-propyl)-2S,$N^1$-dihydroxy-3R-isobutyl-succinamide;

$N^4$-(1S-Cyclopentylcarbamoyl-2,2-dimethyl-propyl)-2S,$N^1$-dihydroxy-3R-isobutyl-succinamide;

$N^4$-(1S-Cyclohexylcarbamoyl-2,2-dimethyl-propyl)-2S,$N^1$-dihydroxy-3R-isobutyl-succinamide;

$N^4$-(1S-Cycloheptylcarbamoyl-2,2-dimethyl-propyl)-2S,$N^1$-dihydroxy-3R-isobutyl-succinamide;

$N^4$-(1S-Cyclopropylcarbamoyl-2-mercapto-2-methyl-propyl)-2S,$N^1$-dihydroxy-3R-isobutyl-succinamide;

$N^4$-(1S-Cyclopropylcarbamoyl-2,2-dimethyl-propyl)-2S,$N^1$-dihydroxy-3R-(3-phenyl-propenyl)-succinamide;

$N^4$-(1S-Cyclopropylcarbamoyl-2,2-dimethyl-propyl)-2S,$N^1$-dihydroxy-3R-(3-phenyl-propyl)-succinamide;

$N^4$-[2,2-Dimethyl-1S-(2-phenyl-cyclopropylcarbamoyl)-propyl]-2S,$N^1$-dihydroxy-3R-isobutyl-succinamide;

2S-Allyl-$N^4$-(1-cyclopropylcarbamoyl-2,2-dimethyl-propyl)-$N^1$-hydroxy-3R-isobutyl-succinamide;

2S-Allyl-$N^4$-(1S-cyclopropylcarbamoyl-2-mercapto-2-methyl-propyl)-$N^1$-hydroxy-3R-isobutyl-succinamide;

$N^4$-(1S-Cyclopropylcarbamoyl-2,2-dimethyl-propyl)-$N^1$-hydroxy-3R-isobutyl-2S-(thiophen-2-ylsulfanyl-methyl)-succinamide;

$N^4$-(1S-Cyclopropylcarbamoyl-2,2-dimethyl-propyl)-$N^1$-hydroxy-2S-(4-hydroxy-phenylsulfanylmethyl)-3R-isobutyl-succinamide; and $N^4$-(1S-Cyclopropylcarbamoyl-2,2-dimethyl-propyl)-2S-(1,3-dioxo-1,3-dihydro-isoindol-2-ylmethyl)-$N^1$-hydroxy-3R-isobutyl-succinamide.

Another especially preferred group of MMP inhibitors to be utilized in the method of this invention are the sulfonated amino acid derivatives described in WO 97/27174, incorporated herein by reference. Those compounds have the general structure

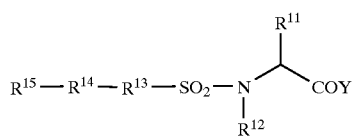

where $R^{11}$ is substituted or unsubstituted lower alkyl, substituted or unsubstituted aryl, substituted or unsubstituted aralkyl, substituted or unsubstituted heteroaryl, or substituted or unsubstituted heteroaryl alkyl;

$R^{12}$ is hydrogen, or a group as defined for $R^{11}$;

$R^{13}$ is a single bond, substituted or unsubstituted arylene, or substituted or unsubstituted heteroarylene;

$R^{14}$ is a single bond, —(CH$_2$)$_{1\text{ or }2}$—, —CH=CH—, —C≡C—, —CO—, —CONH—, —N=N—, NH, N-alkyl, —NHCONH—, —NHCO—, —O—, —S—, —SO$_2$NH—, —SO$_2$NH—N=CH—, or tetrazoldiyl;

$R^{15}$ is substituted or unsubstituted aryl, substituted or unsubstituted heteroaryl, or substituted or unsubstituted non-aromatic heterocyclic group; and Y is NHOH or OH.

Especially preferred compounds to be employed in the method of this invention have the above formula wherein $R^{13}$ is phenylene or substituted phenylene. Typical of such compounds that can be employed have the formula

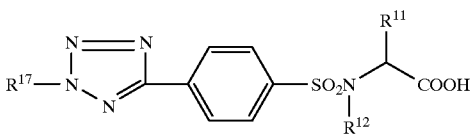

where $R^{11}$ and $R^{12}$ are as defined above, and $R^{17}$ is substituted or unsubstituted aryl or substituted or unsubstituted heteroaryl.

Especially preferred are compounds of the formula

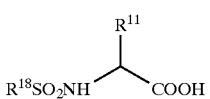

wherein $R^{11}$ and $R^{18}$ are as follows:

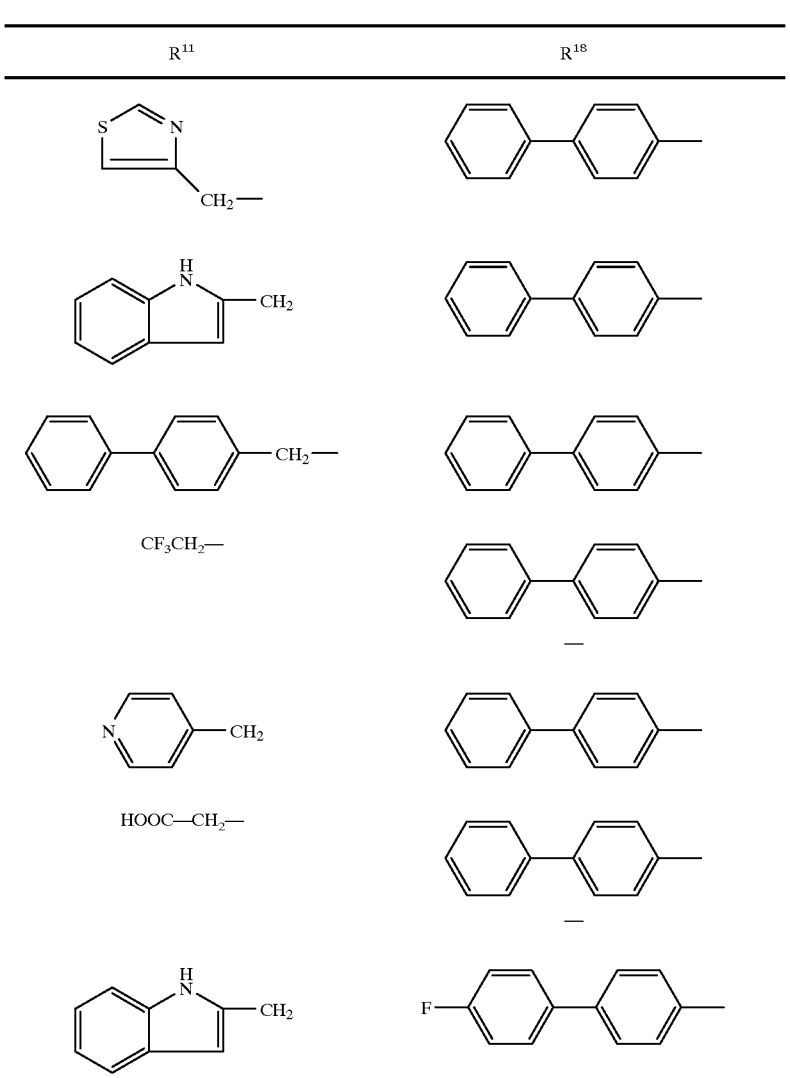

-continued

| $R^{11}$ | $R^{18}$ |
|---|---|
| $(CH_3)_2CH-$ | 4'-methyl-4-biphenylyl (H₃C-C₆H₄-C₆H₄-) |
| $(CH_3)_2CH-$ | 4'-(trifluoromethyl)-4-biphenylyl (F₃C-C₆H₄-C₆H₄-) |
| PhCH₂- | 4'-fluoro-4-biphenylyl (F-C₆H₄-C₆H₄-) |
| $(CH_3)_2CH-$ | 4-phenoxyphenyl (Ph-O-C₆H₄-) |
| indol-3-yl-CH₂- | 4-(4-hydroxyphenoxy)phenyl (HO-C₆H₄-O-C₆H₄-) |
| PhCH₂- | (E)-propenylphenyl (Ph-CH=CH-CH₃... styryl-methyl) |
| indol-3-yl-CH₂- | 2-(benzoxazol-2-yl)phenyl |
| PhCH₂- | 4-(phenylazo)phenyl (Ph-N=N-C₆H₄-) |
| $(CH_3)_2CH-$ | 4-[(4-bromophenyl)sulfonylamino]phenyl (Br-C₆H₄-SO₂-NH-C₆H₄-) |
| $(CH_3)_2CH-$ | 4-[(4-isopropylphenyl)(thien-2-yl)ethynyl... ] (iPr-C₆H₄-C≡C-thiophene-) |
| PhCH₂- | 4-[(4-mercaptophenyl)ethynyl]thien-2-yl (HS-C₆H₄-C≡C-thiophene-) |
| $(CH_3)_2CH-$ | 4-(2-phenyl-2H-tetrazol-5-yl)phenyl |

Especially preferred are the MMP inhibitors currently in clinical development, for example batimastat (2).

MMP compounds in clinical development include batimastat (2) for the treatment of malignant pleural effusion, and marimastat (1) for the treatment of pancreatic cancer. Galardin (3) is for the treatment of corneal ulcers, and a specific MMP-1 inhibitor is RO 31-9790 (4).

Compounds in Clinical Development

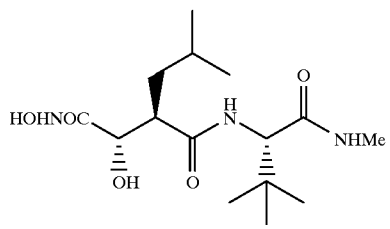
(1)

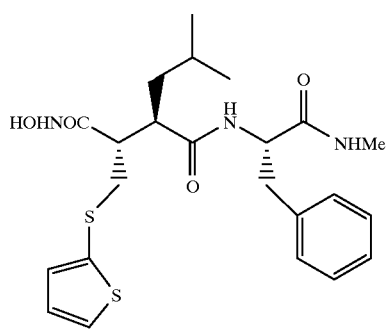
(2)

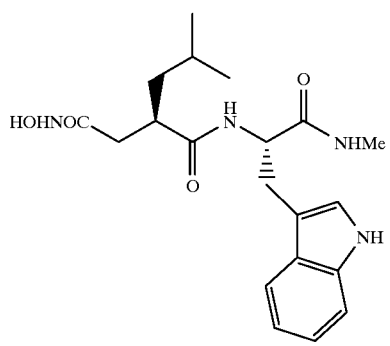
(3)

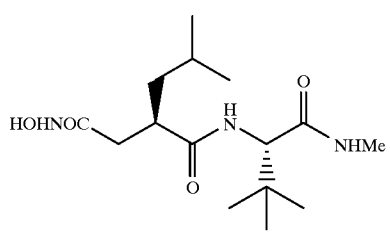
(4)

All that is required to practice the present invention is to administer to a mammal suffering from heart failure or ventricular dilatation, or at risk of developing heart failure or ventricular dilatation, an effective amount of a matrix metalloprotainase inhibitor. Compounds which can inhibit the actions of matrix metalloproteinase enzymes can be identified utilizing routine in vitro and in vivo assays. Several compounds from within the foregoing classes have been evaluated in such standard assays and determined to be potent matrix metalloproteinase inhibitors. The assays measure the amount by which a test compound reduces the hydrolysis of a thiopeptolide substrate caused by a matrix metalloproteinase enzyme. Such assays are described in detail by Ye, et al., in *Biochemistry*, Vol. 31, No 45, 1992, (11231–11235), which is incorporated herein by reference.

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester-Leu-Leu-Gly-O Et. A 100 μL assay mixture will contain 50 mM of 2-morpholinoethane sulfonic acid monohydrate (MES, pH 6.0) 10 mM $CaCl_2$, 100 μM thiopeptolide substrate, and 1 mM 5,5'-dithio-bis-(2-nitro-benzoic acid) (DTNB). The thiopeptolide substrate concentration is varied from 10 to 800 μM to obtain Km and Kcat values. The change in absorbance at 405 nm is monitored on a Thermo Max microplate reader (moleucular Devices, Menlo Park, Calif.) at room temperature (22° C.). The calculation of the amount of hydrolysis of the thiopeptolide substrate is based on $E_{412}=13600$ $m^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table I below presents inhibitory activity for compounds from various classes. In the table, MMP-1 refers to interstitial collagenase; MMP-2 refers to Gelatinase A; MMP-3 refers to stromelysin; MMP-7 refers to matrilysin; and MMP-9 refers to Gelatinase B. Test compounds were evaluated at various concentrations in order to determine their respective $IC_{50}$ values, the micromolar concentration of compound required to cause a 50% inhibition of the hydrolytic activity of the respective enzyme.

TABLE I (IC$_{50}$ μM)

| | MMP1 | MMP2 | MMP3 | MMP7 | MMP9 |
|---|---|---|---|---|---|
| Batimastat is N$^4$-Hydroxy-N$^1$-[2-(methylamine)-2-oxo-1-(phenylmethyl)ethyl]-2-(2-methylpropyl)-3-[(2-thienylthio)methyl]-butanediamide | 0.005 | 0.004 | 0.02 | | |
| CDP-845 (Celltech) | 0.303 | 0.0015 | 0.01 | | |
| CGS 27023A (Ciba-Giegy) | 0.033 | 0.01 | 0.01 | | 0.008 |
| Galardin is N$^4$-Hydroxy-N$^1$-[2-(methylamine)-2-oxo-1-(3-indolylmethyl)ethyl]-2-(2-methylpropyl)-butanediamide | 0.0004 | 0.0005 | 27 | | 0.0002 |
| U24522 (Merck) | | 0.05 | 0.02 | | |
| RO-31-9790 (Roche) | 0.0055 | 0.006 | 0.47 | | |
| 4-Oxo-4-[4-(4-phenyl-piperidin-1-yl)-phenyl]-butyric acid | | 1.3 | 0.14 | | |
| N-Hydroxy-4-oxo-4-[4-(4-phenyl-piperidin-1-yl)-phenyl]-butyramide | | 0.04 | 0.02 | | |
| 4-Oxo-4-[4-(4-phenyl-piperazin-1-yl)-phenyl]-butyric acid | | 1.6 | 0.25 | | |
| [4-(4-Phenyl-piperidin-1-yl)-benzenesulfonylamino]-acetic acid | | 0.21 | 0.02 | | |
| N-Hydroxy-2-[4-(4-phenyl-piperidin-1-yl)-benzenesulfonylamino]-acetamide | | 0.81 | 0.019 | | |
| (S)-3-Phenyl-2-[4-(4-phenyl-piperidin-1-yl)-benzenesulfonylamino]-propionic acid | | 0.22 | 0.014 | | |
| (S)-2-[4-(4-Benzyl-piperidin-1-yl)-benzenesulfonylamino]-3-phenyl-propionic acid | | 0.088 | 0.021 | | |
| (S)-2-{4-[-4-(4-Methoxy-phenyl)-piperazin-1-yl]-benzenesulfonylamino}-3-phenyl-propionic acid | | 0.033 | 0.014 | | |
| (S)-2-(4'-Bromo-biphenyl-4-sulfonylamino)-3-methyl-butyric acid | 3.24 | 0.025 | 0.012 | | |
| (S)-3-Methyl-2-(4'-nitro-biphenyl-4-sulfonylamino)-butyric acid; | | 0.013 | 0.10 | | |
| (S)-2-(4'-Amino-biphenyl-4-sulfonylamino)-3-methyl-butyric acid | | 0.044 | 0.067 | | |
| (S)-2-(4'-Bromo-biphenyl-4-sulfonylamino)-3-phenyl-propionic acid | | 0.026 | 0.026 | | |
| 4-(4'-Chloro-biphenyl-4-yl)-4-hydroxyimino-butyric acid | | 0.39 | 0.12 | | |
| 4-(4'-Bromo-biphenyl-4-yl)-4-hydroxyimino-butyric acid | | 0.058 | 0.11 | | |
| 4-(4'-Chloro-biphenyl-4-yl)-4-(dimethylhydrazono)-butyric acid | | 0.73 | 0.93 | | |
| (±)-4-(4'-Chloro-biphenyl-4-yl)-4-hydroxy-butyric acid | | 0.15 | 0.28 | | |
| (S)-2-(Dibenzofuran-2-sulfonylamino)-4-phenyl-butyric acid | | 0.265 | 0.46 | | |
| (L)-2-(Dibenzofuran-2-sulfonylamino)-4-methyl-pentanoic acid | | 0.32 | 1.18 | | |
| (L)-2-(Dibenzofuran-2-sulfonylamino)-3-phenyl-propionic acid | | 0.89 | 0.72 | | |
| (L)-2-(Dibenzofuran-2-sulfonylamino)-3-methyl-butyric acid | | 0.084 | 0.23 | | |
| (L)-2-(Dibenzofuran-2-sulfonylamino)-3-tritylsulfanyl-propionic acid | | 9.4 | 14.4 | | |
| (L)-2-(Dibenzofuran-2-sulfonylamino)-3-mercapto-propionic acid | | 4.45 | 0.69 | | |
| (S)-4-Dibenzofuran-2-yl-4-oxo-2-(2,2,2-trifluoroacetylamino)-butyric acid | | 0.72 | 1.33 | | |
| (S)-2-Amino-4-dibenzofuran-2-yl-4-oxo-butyric acid | | 3.8 | 33.0 | | |
| (S)-2-Acetylamino-4-dibenzofuran-2-yl-4-oxo-butyric acid | | 0.16 | 1.55 | | |
| (S)-4-Dibenzofuran-2-yl-4-oxo-2-phenylacetylamino-butyric acid | | 0.084 | 0.33 | | |
| (S)-4-Dibenzofuran-2-yl-4-oxo-2-(3-phenyl-propionylamino)-butyric acid | | 0.096 | 0.28 | | |

As noted above, any matrix metalloproteinase inhibitor can be used to treat or prevent ventricular dilatation and congestive heart failure according to this invention. Typical inhibitors have been evaluated in three models of heart failure, namely the spontaneously hypertensive heart failure (SHHF) model, the pacing-induced heart failure model, and the coronary artery ligation model (the MI-rat).

The SHHF rat is an inbred line which exhibits the same pathology (e.g., atrial thrombi, cyanosis, cardiac functional deficits, ventricular dilatation, dyspnea, pleural effusions, mortality) as human heart failure patients. These animals are hypertensive, hyperlipidemic, have noninsulin dependent diabetes, and are obese. All these characteristics are identified risk factors for heart failure in humans. One hundred percent of SHHF rats develop heart failure. In addition, the transition from asymptomatic to overt heart failure in obese male SHHF rats is clearly defined to a narrow window of time between 8 to 9 months of age (asymptomatic), and to 12 to 13 months (overt heart failure). Therefore, a 4-month drug treatment study in SHHF rats spanning the transition from asymptomatic to overt heart failure would determine drug efficacy against the progression of heart failure.

The pacing-induced heart failure model relies upon the fact that chronic rapid pacing causes a well defined, predictable, and progressive ventricular dilatation, contractile dysfunction, and neurohumoral system activation in dogs, pigs, rabbits, and rats. Moreover, the fibrillar collagen weave supporting adjacent myocytes is reduced with the development of pacing induced CHF. These functional and neurohumoral changes are similar to the clinical spectrum of ventricular dilatation and heart failure in humans. The induction of overt heart failure occurs within a 3-week period. In addition, ventricular dilatation has been shown to precede the development of left ventricular dysfunction which indicates that cardiac remodeling is an important component in this animal model of heart failure. Pacing-induced tachycardia in animals provides a rapid technique for generating a syndrome resembling heart failure in humans.

A study was performed in four pigs in which atrial pacemakers were implanted. Heart failure was induced by chronic rapid pacing (i.e., increasing heart rate to 240 beats per minute). Echocardiographic assessment of cardiac function, chamber dimensions, and structure was performed prior to the initiation of pacing, and following 1 and 3 weeks of rapid pacing. Previous studies have shown that 1 week of rapid atrial pacing represents an early timepoint in the development of heart failure in which cardiac dilation is evident, but there is no significant effect on left ventricular (LV) systolic function. Two pigs were dosed with the MMP-inhibitor 2-(4'-bromobiphenyl-4-sulfonylamino)-3-methylbutyric acid (Compound A) (20 mg/kg/day) which was given once a day orally. This dosage was selected based upon pharmacokinetic data in which this dosage regimen would provide minimal steady state plasma levels of 10 $\mu$M Compound A. One pig dosed with Compound A was sacrificed at the end of 1 week of pacing, and the second pig was paced for a full 3 weeks. At the end of 3 weeks, pigs were euthanized and the heart removed. Cardiac myocytes were isolated from a portion of the left ventricle to measure changes in cell length. Previous studies have shown that cardiac myocyte cell length increases significantly in both human patients with heart failure as well as pigs with pacing-induced heart failure.

MMP-Inhibitor efficacy in treating heart failure was defined as stopping cardiac dilation, preserving cardiac function, and reducing cardiac myocyte lengthening. Cardiac dilation was assessed by measuring changes in the end-diastolic dimension between the left ventricular free wall and left ventricular septum. Cardiac function was also measured using m-mode echocardiography by calculating the percent fraction shortening, or in other words, how well the left ventricle of the heart pumped blood into the circulation. Cellular remodelling was measured by isolating cardiac myocytes using a standard collagenase digestion procedure and measuring cell length using digital photomicroscopy. To confirm plasma drug levels of the MMP-inhibitor, plasma was collected prior to dosing on each day of the pacing protocol.

During the treatment period, trough drug levels of Compound A were 10.5 to 2.2 $\mu$M, a level great enough to inhibit all MMPs tested. Results are shown in the table below.

TABLE II

| | Baseline | Paced 7 Days | Paced 21 Days |
|---|---|---|---|
| Heart Rate (BPM) | | | |
| Paced | 108 ± 3 | 132 ± 2 | |
| Paced + Compound A | 105 ± 4 | 120 ± 3 | |
| End-Diastolic Dimension (cm) | | | |
| Paced | 3.3 ± 0.2 | 4.6 ± 0.3 | 6.0 ± 0.2 |
| Paced + Compound A | 3.4 ± 0.2 | 3.6 ± 0.2 | 4.3 |
| Fractional Shortening (%) | | | |
| Paced | 38 ± 2 | 30 ± 3 | 14 ± 3 |
| Paced + Compound A | 36 ± 3 | 33 ± 3 | 22 |
| LV Stress (g/cm2) | | | |
| Paced | 42 ± 4 | 76 ± 6 | |
| Paced + Compound A | 46 ± 3 | 50 ± 4 | |
| Cardiac Myocyte Length ($\mu$ms) | | | |
| SHAM | | | 130 |
| Paced + Compound A | | | 170 |
| Paced | | | 155 |

Following the first week of pacing, the Paced only group which received no drug was observed to have a left ventricular end-diastolic dimension increased from control values by 40% and peak left ventricular wall stress by 81%. In the group receiving the MMP-inhibitor, left ventricular end-diastolic volume and left ventricular wall stress remained unchanged from control values. Cardiac function as measured by fractional shortening was unchanged in either group following 1 week of pacing as expected at this early timepoint. These results show that MMP-inhibition blocks cardiac dilation at an early timepoint during the development of heart failure, and dramatically reduces end-diastolic wall stress. Following 3 weeks of pacing, cardiac dilation increased (left ventricular end-diastolic dimension by 82%) in the Paced only group, but only 26% in the pig treated with the MMP-inhibitor. Cardiac function was preserved in the group treated with the MMP-inhibitor showing a 39% decrease versus a 63% decrease in the Paced only group. Determination of cardiac myocyte cell length showed that cell length increased by 31% in the Paced only group, but only 19% in the MMP-inhibitor treated group. These results show that MMP-inhibition decreased ventricular dilatation, improved cardiac function, and slowed cellular remodelling in a pacing-induced model of congestive heart failure.

In a similar study, three Yorkshire pigs (22–25 kg, male, Hambone Farms, S.C.) were chronically instrumented in order to measure arterial blood pressure in the conscious state. The pigs were anesthetized with isoflurane (3%/1.5 L/min) and a mixture of nitrous oxide and oxygen (50:50), intubated with a cuffed endotracheal tube and ventilated at a flow rate of 22 mL/kg/minute, and a respiratory rate of 15/minute. A left thoracotomy was performed, and the thoracic aorta at the location of the hemi-azygous crossover exposed. A catheter connected to a vascular process port (Model GPV, 9F, Access Technologies, Skokie, Ill.) was placed in the aorta and sutured in place. The access port was buried in a subcutaneous pocket over the thoracolumbar fascia. Following a recovery period of 7 to 10 days, the animal was returned to the laboratory for baseline studies. For these studies, the animals were sedated with diazepam (20 mg, PO, Valium, Hoffmann-La Roche, Nutley, N.J.) and placed in a custom designed sling which allowed the animal to rest comfortably. All studies were performed in the conscious state without additional use of sedation. The vascular access port was entered using a 12-gauge Huber needle (Access Technologies, Skokie, Ill.) and basal, resting arterial pressure and heart rate were recorded. Pressures from the fluid filled aortic catheter were obtained using an externally calibrated transducer (Statham P23ID, Gould, Oxnard, Calif.). Following baseline studies, the pigs were then used for initial MMP inhibition dosage studies.

The MMP inhibitor chosen for these studies was Compound A as above. A single oral dose of 10 mg/kg of Compound A was administered in one pig, and a second pig was simultaneously administered a single 10 mg/kg dose of the MMP inhibitor intravenously. Plasma samples were serially collected from the chronically placed arterial access ports. Plasma levels of the MMP inhibitor were determined by the degree of hydrolysis of the MMP substrate thiopeptolide Ac-Pro-Leu-Gly-thioester-Leu-Leu-Gly=OEt. The oral administration of Compound A reached nearly 100% bioavailability by 4 hours and exhibited potent MMP inhibitory activity as evidenced by an approximate 50% reduction in activity against the gelatinases and the catalytic domain of stromelysin. A pharmacokinetic profile was constructed using these initial data, and it was predicted that an oral delivery of 20 mg/kg/day of Compound A would provide significant MMP plasma inhibitory activity at trough levels. Accordingly, the 3 pigs underwent 20 mg/kg QD-AM of treatment with Compound A for 5 days. In order to confirm adequate MMP inhibitory activity, plasma was collected prior to the AM dose with each day of treatment. During this treatment period, significant plasma MMP inhibitory activity was observed. Specifically, based upon an artificial MMP substrate, the plasma collected after 3 days of MMP inhibition treatment reduced in vitro MMP activity by over 100%. There were no significant changes in heart rate, blood pressure, or observable abnormalities upon physical exam in any of the pigs undergoing this period of MMP inhibition. Thus, a practical dosing regiment of Compound A was established which provided stable plasma MMP inhibitory activity in the animal model to be used in the present study.

Experimental Protocol and Animal Model Preparation

Following the MMP inhibition dose selection studies, the effects of concomitant treatment with MMP inhibition with chronic rapid pacing was examined. Twenty weight matched pigs (22–23 kg) were randomly assigned to 3 groups: (1) rapid atrial pacing (240 bpm) for 3 weeks (n=8), (2) concomitant MMP inhibition (Compound A 20 mg/kg/day) and rapid pacing (n=7), and (3) and (5) sham controls (n=5). The drug treatment was begun 3 days prior to the initiation of pacing and continued for the entire 21-day pacing protocol.

Pacemakers were implanted or sham procedures performed with the animals anesthetized as described in the preceding section. In addition to the placement of the aortic access port, a shielded stimulating electrode was sutured onto the left atrium, connected to a modified programmable pacemaker (8329, Medtronic, Inc., Minneapolis, Minn.), and buried in a subcutaneous pocket. The pericardium was approximated, the thoracotomy closed, and the pleural space evacuated of air. Ten to 14 days following recovery from the surgical procedure, baseline studies were performed, and the protocols described above were begun. Cardiac auscultation and an electrocardiogram were performed frequently during the pacing protocol in order to ensure proper operation of the pacemaker and the presence of 1:1 conduction. In this porcine preparation, atrio-ventricular conduction can be maintained at this pacing rate and therefore provide a homogeneous pattern of ventricular myocardial electrical activation. The sham operated controls were cared for in identical fashion with the exception of the pacing protocol. All animals were treated and cared for in accordance with the National Institutes of Health "Guide for the Care and Use of Laboratory Animals" (National Research Council, Washington, 1996).

LV Function and Hemodynamic Measurements

LV size and function were measured at weekly intervals in all of the pigs undergoing rapid pacing. For these studies, the animals were brought to the laboratory and the pacemaker deactivated. All measurements were performed at an ambient resting heart rate within 30 to 40 minutes following pacemaker deactivation. Two-dimensional and M-mode echocardiographic studies (ATL Ultramark VI, 2.25 MHz transducer, Bothell, Wash.) were used to image the LV from a right parasternal approach. LV fractional shortening was calculated as (end-diastolic dimension/end-systolic dimension)/end-diastolic dimension and was expressed as a percent. Peak circumferential global average wall stress was computed using a spherical model of reference: $\sigma(gm/cm^2)= (PD/4h(1+h/D))\times 1.36$; where P=aortic systolic pressure measured from the access port, D=minor axis dimension at end-diastole, and h=wall thickness. The mean velocity of circumferential fiber shortening (Vcf) was calculated using the LV echocardiographic dimension measurements and the arterial pressure trace. The LV ejection time, used in the calculation of Vcf, was rate-corrected to a heart rate of 60 bpm by multiplying by the square root of the RR interval.

Terminal Study: Myocardial Sampling and Myocyte Isolation

Following completion of the 21-day protocol, a final set of LV function measurements were performed and plasma collected. Following steady-state LV function measurements, 35 cc of blood was drawn from the arterial access port into chilled tubes containing EDTA (1.5 mg/mL). The blood samples were immediately centrifuged (2000 g, 10 min, 4° C.), the plasma decanted into separate tubes, frozen in a dry ice/methanol bath, and stored at −80° C. until the time of assay. The animals were then anesthetized as described in the preceding section, a sternotomy performed, and the heart quickly extirpated and placed in a phosphate buffered ice slush. The great vessels, atria, and right ventricle were carefully trimmed away, and the LV weighed. The region of the LV free wall incorporating the circumflex artery (5×5 cm) was excised and prepared for myocyte isolation. The region of the left ventricular free wall comprising the left anterior descending artery (3×5 cm) was cannulated and prepared for perfusion fixation.

Neurohormonal Measurements

The plasma samples were assayed for renin activity, catecholamine levels, and plasma MMP inhibition levels. Plasma renin activity (PRA) was determined by computing angiotensin I production using a radioimmunoassay (NEA-026, New England Nuclear, Boston, Mass.). Plasma norepinephrine was measured using high-performance liquid chromatography and normalized to pg/mL of plasma. All assays were performed in duplicate.

LV Myocyte Contractile Function

Myocytes were isolated from the LV free wall as follows. The left circumflex coronary artery was perfused with a collagenase solution (0.5 mg/mL, Worthington, type II; 146 U/mg) for 35 minutes. The tissue was then minced into 2 mm sections and gently agitated. After 15 minutes, the supernatant was removed, filtered, and the cells allowed to settle. The myocyte pellet ($5 \times 10^4$ cells/mL) was then resuspended in standard cell culture media (M199, Gibco Laboratories, Grand Island, N.Y.). Using this myocyte isolation method, a high yield (85±5%) of viable myocytes were obtained in all LV preparations used in this study. Viable myocytes were defined as those cells which retained a rod shape, were calcium tolerant, responded to electrical stimulation, and excluded trypan blue. Isolated myocyte function was examined using a thermostatically controlled chamber (37° C.) containing a volume of 2.5 mL and two stimulating platinum electrodes to image the isolated myocytes on an inverted microscope (Axiovert IM35, Zeiss Inc., Germany). A 20× long working distance Hoffmann Modulation Contrast objective (Modulation Optics Inc., Greenvale, N.Y.) was used to image the myocytes. Myocyte contractions were elicited by field stimulating the tissue chamber at 1 Hz (S11, Grass Instruments, Quincy, Mass.) using current pulses of 5 msec duration and voltages 10% above contraction threshold. Myocyte motion signals were captured and input through an edge detector system (Crescent Electronics, Sandy, Utah). The distance between the left and right myocyte edges was converted into a voltage signal, digitized, and input to a computer (80386; ZBV2526, Zenith Data Systems, St. Joseph, Mich.) for analysis. Parameters computed from the digitized contraction profiles include percent shortening, velocity of shortening, velocity of relengthening, time to peak contraction, and duration of contraction. In addition to basal measurements of contractility, myocyte function was determined following β-adrenergic receptor stimulation with 25 nM isoproterenol, or in the presence of 8 mM extracellular $Ca^{+2}$ yield a near maximal contractile response in normal porcine myocyte preparations.

LV Myocardial Fibrillar Collagen Structure

The cannulated left anterior descending artery was perfused with 150 cc of 10% buffered formalin at a perfusion pressure of 75 mmHg. Full thickness sections of the perfused LV myocardium were then immersed in fresh fixative overnight. The specimens were then dehydrated through a series of graded ethanols, cleared in xylenes, and embedded in paraplast. Slices of 4 μm in thickness were cut from the blocks and mounted on glass slides. The sections were then rehydrated and stained using the picro-sirius histochemical technique. This method is used routinely to provide a strong histochemical signal for the LV myocardial collagen matrix. The sections were then digitized at a final magnification of 320× and analyzed using an image analysis system (Sigma Scan/Image, Jandel, San Rafael, Calif.). The percent area of extracellular staining was computed from 15 random fields within the midmyocardium in order to exclude large epicardial arteries and veins and any cutting or compression artifact.

Data Analysis

Indices of LV and myocyte function were compared between the three treatment groups using multi-way analysis of variance (ANOVA). For comparisons of LV function with each week of pacing, an ANOVA for repeated measures was used. If the ANOVA revealed significant differences, pairwise tests of individual group means were compared using Bonferroni probabilities. For comparisons of neurohormonal profiles, the Student-Neuman-Kuells test was employed. The categorical scores obtained from the histomorphometric studies were compared between groups using the Chi-Square analysis. All statistical procedures were performed using the BMDP statistical software package (BMDP Statistical Software Inc., Los Angeles, Calif.). Results are presented as mean ± standard error of the mean (SEM). Values of $p<0.05$ were considered to be statistically significant. Data from the foregoing experiment are presented in Tables III and IV.

TABLE III

LV Geometry, LV Function, Systemic Hemodynamics, and Plasma Neurohormones With Chronic Rapid Pacing Effects of Chronic Matrix Metalloproteinase Inhibition

| | Baseline | Rapid Pacing[a] | Rapid Pacing + MMPi[b] |
|---|---|---|---|
| Heart Rate (bpm) | 113 ± 3 | 176 ± 5* | 149 ± 3*+ |
| Mean Arterial Pressure (mmHg) | 94 ± 1 | 81 ± 3* | 83 ± 2* |
| LV Size and Function | | | |
| End-Diastolic Dimension (cm) | 3.6 ± 0.1 | 5.7 ± 0.1* | 4.7 ± 0.2*+ |
| Wall Thickness (CM) | 0.86 ± 0.01 | 0.49 ± 0.02* | 0.80 ± 0.22*+ |
| Peak Wall Stress (g/cm²) | 138 ± 3 | 373 ± 13* | 185 ± 11*+ |
| Fractional Shortening (%) | 46 ± 1 | 18 ± 3* | 26 ± 3*+ |
| Vcf ($s^{-1}$)[c] | 2.1 ± 0.1 | 1.1 ± 0.2* | 1.4 ± 0.2* |
| $VCF_c$ ($s^{-1c}$)[d] | 2.9 ± 0.2 | 1.9 ± 0.3* | 2.3 ± 0.2* |
| Plasma Neurohormones | | | |
| Renin Activity (ng/mL/hr) | 4.8 ± 0.6 | 15.6 ± 5.2* | 10.4 ± 1.1* |
| Norepinephrine (pg/mL) | 288 ± 45 | 1091 ± 248* | 1073 ± 241* |
| Sample Size (n) | 15 | 8 | 7 |

Values presented as Mean ± SEM
*$p < 0.05$ vs Baseline;
+$p < 0.05$ vs Rapid Pacing only
[a]Rapid Pacing: 3 weeks of supraventricular pacing at 240 bpm
[b]Rapid Pacing + MMPi: Rapid pacing with concomitant treatment with Compound A (20 mg/kg QD)
[c]Vcf: Velocity of circumferential fiber shortening
[d]$Vcf_c$: Velocity of circumferential fiber shortening corrected for heart rate

TABLE IV

Isolated Myocyte Contractile Function With Pacing Induced Congestive Heart Failure Effects of Chronic Matrix Metalloproteinase Inhibition

| | Baseline | 25 nM Isoproterenol | 7 mM Calcium |
|---|---|---|---|
| Resting Length (μm) | | | |
| Control | 125 ± 4 | 120 ± 4 | 118 ± 5 |
| Rapid Pacing[a] | 180 ± 3* | 169 ± 2** | 165 ± 7** |
| Rapid Pacing + MMPi[b] | 169 ± 4* | 161 ± 3*+ | 156 ± 5*+ |
| Percent Shortening (%) | | | |
| Control | 5.8 ± 0.2 | 11.7 ± 0.9** | 9.5 ± 0.4** |
| Rapid Pacing[a] | 2.3 ± 0.1* | 4.7 ± 0.3*, ** | 4.9 ± 0.8*, ** |
| Rapid Pacing + MMPi[b] | 2.2 ± 0.1* | 5.1 ± 0.5*, ** | 5.6 ± 0.5*, ** |
| Shortening Velocity (μm/s) | | | |
| Control | 66 ± 1 | 204 ± 17* | 119 ± 9* |
| Rapid Pacing[a] | 33 ± 2* | 94 ± 9*, ** | 69 ± 10*, ** |
| Rapid Pacing + MMPi[b] | 31 ± 2* | 108 ± 11*, ** | 84 ± 7*, ** |

TABLE IV-continued

Isolated Myocyte Contractile Function With Pacing
Induced Congestive Heart Failure Effects of Chronic
Matrix Metalloproteinase Inhibition

|  | Baseline | 25 nM Isoproterenol | 7 mM Calcium |
|---|---|---|---|
| Relengthening Velocity ($\mu$m/s) | | | |
| Control | 67 ± 4 | 169 ± 15** | 124 ± 11** |
| Rapid Pacing[a] | 29 ± 2* | 62 ± 5*, ** | 64 ± 9*, ** |
| Rapid Pacing + MMPi[b] | 26 ± 2* | 80 ± 11*, ** | 78 ± 5*, ** |
| Time to Peak Contraction (ms) | | | |
| Control | 235 ± 10 | 183 ± 4** | 262 ± 13 |
| Rapid Pacing[a] | 267 ± 8* | 198 ± 4*, ** | 274 ± 10 |
| Rapid Pacing + MMPi[b] | 244 ± 7+ | 175 ± 2+, ** | 240 ± 3+ |
| Time to 50% Relaxation (ms) | | | |
| Control | 90 ± 4 | 71 ± 5** | 86 ± 7 |
| Rapid Pacing[a] | 134 ± 5* | 124 ± 5* | 127 ± 14* |
| Rapid Pacing + MMPi[b] | 131 ± 5* | 104 ± 6*, **, + | 102 ± 5+, ** |
| Total Duration (ms) | | | |
| Control | 501 ± 17 | 380 ± 15** | 472 ± 18 |
| Rapid Pacing[a] | 533 ± 13 | 488 ± 15*, ** | 556 ± 28* |
| Rapid Pacing + MMPi[b] | 498 ± 9 | 433 ± 12*, **, + | 476 ± 10+ |

Values presented as Mean ± SEM
Sample Sizes: Control, n = 7 pigs; Rapid Pacing, n = 6 pigs; Rapid Pacing + MMPi, n = 5 pigs.
*$p < 0.05$ vs Control
**$p < 0.05$ vs Baseline
+$p < 0.05$ vs Rapid Pacing
[a]Rapid Pacing: 3 weeks of supraventricular pacing at 240 bpm
[b]Rapid Pacing + MMPi: Rapid pacing with concomitant treatment with Compound A (20 mg/kg QD)

Other potential models of heart failure are (1) coronary artery ligation (2) microembolization, (3) adriamycin-induced, (4) cardiomyopathic hamster, and (5) transgenic mice. The first three models generate heart failure producing cardiac necrosis and possibly apoptosis (i.e., programmed cell death). Coronary artery ligation and microembolization have the advantage of having a well established stimulus, myocardial ischemia, and they produce a progressive decline in left ventricular function which is amenable to both progression and regression studies. The disadvantages of coronary ligation are that infarct size must be quantified prior to drug treatment. Microembolization induced heart failure relies on producing a series of cardiac ischemic episodes over several months. This technique has the disadvantage of being time- and labor-intensive as well as being confined to large animals. Adriamycin induces myocardial necrosis, upregulates MMPs, and causes cardiac dilation and left ventricular dysfunction. The necrosis and heart failure appears to be produced by bursts of oxygen radical production within the heart. This technique is relatively easy and reliable, generates overt heart failure within about a month, and can be performed in a variety of species.

The cardiomyopathic hamster is a well-characterized animal model of heart failure. This strain of hamsters all develop and eventually die from heart failure. However, the transition to overt heart failure varies widely between animals. In addition, the time between asymptomatic and overt heart failure is relatively long at 6 months making drug studies problematic. This model can have utility as a tertiary screen for drug-effects on mortality.

A well-characterized transgenic mouse model of heart failure is not currently available. Any model should recapitulate the biventricular structural and functional changes in human heart failure instead of merely involving depressed left ventricular function. In addition, mice should ultimately exhibit the same clinical phenomenology as human heart failure patients (e.g., fluid retention, dyspnea, atrial thrombi, etc). Although most efforts have focussed on knockout mice, an overexpressor mouse might be more successful such as a stromelysin or collagenase. In addition, a Cre-Lox system in which overexpression could be turned on selectively might avoid developmental abnormalities, and provide a more defined pathology.

Two studies were performed to assess MMP-inhibition in the ischemic model of heart failure (MI-rat). In the first study, a dose-response relationship was generated on Compound A. In the second study, Compound B (S-2-(9H-fluorene-2-sulfonylamino)-4-phenyl-butyric acid) was tested at a single dose.

Methods: Male rats were obtained from Charles River. The rats were infarcted at 6 weeks of age at Charles River.

Groups: In the dose-response study of Compound A, 6 groups of rats (N=18 per group) were tested: (1) Sham controls, (2) non-drug treated group, and (3–6) test Compound A was administered at doses achieving 0.1, 1, 10, and 100 $\mu$M plasma levels. Drugs were administered in chow such that the investigators were blinded to group assignment. A biweekly record of health status, body weight, and food consumption was maintained.

In the Compound B efficacy study, 3 groups of rats (N=20 per group) were tested: (1) Sham controls, (2) non-drug treated group, and (3) Compound B treated.

Drug Administration Study: In the dose-response study of Compound A, rats were dosed with 0.005, 0.05, 0.5, and 5 mg/kg/day in chow. Dosing began at 2 weeks post-MI and continued for 6 weeks.

In the efficacy study of Compound B, drug was administered in chow at a dose of 2.5 mg/kg/day, which was predicted to produce a plasma level of 100 $\mu$M. This dose has been shown to inhibit all MMPs tested in rats. Dosing began at 2 weeks post-MI and continued for 6 weeks.

Terminal Cardiovascular Test: Rats were anesthetized with isoflurane (3–4%) for assessing cardiovascular function. Isoflurane was administered using a mask until the rats were anesthetized and a tracheotomy performed. The rats were then respired using a ventilator (ADS 1000, Engler Engineering Corp., Hialeah, Fla.). A Millar pressure transducer was advanced into the left ventricle (LV) via the right carotid to measure LV end-diastolic pressure (EDP) and end-systolic pressure (ESP), and heart rate (HR). Data was recorded using a digital data acquisition system (Gould Instrument Systems, Inc., Valley View, Ohio). In addition, the left carotid and abdominal aorta just below the diaphragm was isolated to generate isovolumic beats. Baseline measurements of cardiovascular function were made by decreasing the amount of isoflurane to between 1% and 2% until LVESP was approximately 120 mm Hg, and a 10-second average was taken. Two or three series of isovolumic beats were then generated as a further measure of LV contractile function. The level of isoflurane was decreased to 0.5% to increase sympathetic drive, and LV function was assessed at an LVESP of 145 mm Hg based on a 10-second average.

The isoflurane level was then increased to 2%; the Millar was removed from the carotid and replaced with a PE-50 cannula. A 5 mL blood sample was taken using the PE-50 cannula and an ice-cold syringe. Blood was then put into an ice-cold EDTA tube, and centrifuged at 5000 RPM for 10 minutes at 4° C. Plasma was aliquoted, then stored at −80° C. until assays were performed to assess plasma drug levels and other factors.

The heart was arrested with KCl. One lobe of the lung was excised, blotted dry, and snap frozen in liquid $N_2$. The heart was excised, and a glass cannula was inserted into the LV via the aorta. A ligature was securely tied around the atrio-ventricular groove which sealed the LV. The heart was suspended in air beneath the cannula, and cardiac dilation was measured by generating LV pressure-volume (PV) curves. Two or three PV curves were generated by evacuating the LV of saline and then filling the LV at a fixed rate using a programmable pump set at a 1 mL/min flow rate, and recording LV pressure using a digital data acquisition system.

The heart was taken off the cannula, and the atria quickly removed. The right ventricle was excised and snap frozen in liquid $N_2$. A 2 to 3 mm cross-section of the heart (at the level of the right ventricular papillary muscles) was taken and immersion fixed in buffered formalin. The remainder of the LV tissue was frozen in liquid $N_2$. The formalin fixed LV specimens were used for histology and infarct size quantification. Frozen and fixed LV and RV tissue were weighed in pre-tared containers to get chamber weights.

This data demonstrates that MMP-inhibition limits the progression of heart failure.

The compounds to be employed in the present invention can be prepared and administered in a wide variety of oral and parenteral dosage forms for treating and preventing heart failure. The compounds can be administered by injection, that is, intravenously, intramuscularly, intracutaneously, subcutaneously, intraduodenally, or intraperitoneally. Also, the compounds can be administered by inhalation, for example, intranasally. Additionally, the compounds can be administered transdermally. It will be obvious to those skilled in the art that the following dosage forms may comprise as the active component, either a compound as a free base, acid, or a corresponding pharmaceutically acceptable salt of such compound. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspend-

|  | | | Compound A Dose (mg/kg/day, in chow) | | | |
|---|---|---|---|---|---|---|
|  | SHAM | Vehicle | 0.005 | 0.05 | 0.5 | 5 |
| Plasma Level ($\mu$M) |  |  | 2 ± 1 | 16 ± 4 | 55 ± 3 | 201 ± 7 |
| LVV at LVEDP | 224 ± 22 | 1038 ± 69* | 650 ± 96*,H | 622 ± 72*,H | 751 ± 65*,H | 647 ± 66*,H |
| dp/dt MAX (mm Hg/sec) | 8452 ± 197* | 4966 ± 197* | 5900 ± 474* | 6553 ± 331*,H | 5997 ± 351*,H | 6357 ± 237*,H |
| LVEDP (mm Hg) | 4 ± 1 | 24 ± 3* | 20 ± 4 | 16 ± 3* | 20 ± 3* | 16 ± 3* |
| N | 14 | 15 | 13 | 15 | 16 | 18 |

*$p < 0.05$ SHAM
H$p < 0.05$ Vehicle

There was a stepwise increase in plasma drug concentrations across the 4 dose groups. Compound A significantly reduced LV dilation at every dose, and significantly improved LV function as measured by dP/dt MAX at the 3 highest doses. These results demonstrate the efficacy of Compound A in a model of HF which shares the same primary etiology as human HF.

The efficacy of another MMP-inhibitor, Compound B, was evaluated in the same MI-rat model described above. Compound B (2.5 mg/kg/day, in chow) administration was initiated 2 weeks post-MI, and rats were dosed for 6 weeks. Compound B was present in sufficient blood levels at this dosing to be effective as an MMP inhibitor. Efficacy against heart failure was evaluated at 8 weeks post-MI in terms of a reduction in LV dilation and normalization of LV systolic function. Results are shown below:

|  | SHAM | Vehicle | Compound B |
|---|---|---|---|
| LVV at LVEDP | 207 ± 23 | 1038 ± 69* | 555 ± 103*,H |
| dP/dt MAX (mm Hg/sec) | 8330 ± 173 | 4966 ± 197*,H | 6939 ± 314*,H |
| LVEDP (mm Hg) | 4.1 ± 0.6 | 24.4 ± 2.8* | 11.5 ± 2.6*,H |
| N | 18 | 15 | 11 |

* $p < 0.05$ SHAM
H$p < 0.05$ Vehicle

Compound B was also effective in reducing cardiac dilation (52%) compared to the vehicle control and significantly improved LV function as measured by dP/dt MAX.

ing agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit-dose preparation may be varied or adjusted from 1 to 1000 mg, preferably 10 to 100 mg according to the particular application and the potency of the active component. The composition can, if desired, also contain other compatible therapeutic agents.

The compounds utilized in the pharmaceutical method of this invention are administered at a dose that is effective to inhibit the hydrolytic activity of one or more matrix metalloproteinase enzymes. Such effective amounts are thus those which prevent or treat CHF and ventricular dilatation. The compounds can also be used prophalactically at the same dose levels. The initial dosage of about 1 mg to about 100 mg per kilogram daily will be effective to prevent and treat heart failure. A daily dose range of about 5 to about 75 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg.

The following examples illustrate typical formulations that can be utilized in the invention.

| Ingredient | Amount (mg) |
| --- | --- |
| 2-(4'-bromobiphenyl-4-sulfonylamino)-3-methyl-butyric acid | 25 |
| Lactose | 50 |
| Corn starch (for mix) | 10 |
| Corn starch (paste) | 10 |
| Magnesium stearate (1%) | 5 |
| Total | 100 |

The biphenylsulfonamide, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis and arthritis.

| Preparation for Oral Solution | |
| --- | --- |
| Ingredient | Amount |
| (R)-2-(4'-Cyanobiphenyl-4-sulfonylamino)-3-phenyl-propionic acid sodium salt | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the biphenylsulfonamide is dissolved therein. The saccharin, sodium benzoate, flavor, and dye are added and dissolved. The volume is adjusted to 100 mL with distilled water. Each milliliter of syrup contains 4 mg of invention compound.

Parenteral Solution

In a solution of 700 mL of propylene glycol and 200 mL of water for injection is suspended 20 g of (S)-2-(4'-amino-biphenyl-4-sulfonylamino)-3-(3-ethoxyphenyl)-propionic acid. After suspension is complete, the pH is adjusted to 6.5 with 1 N sodium hydroxide, and the volume is made up to 1000 mL with water for injection. The formulation is sterilized, filled into 5.0 mL ampoules each containing 2.0 mL, and sealed under nitrogen.

We claim:

1. A method for treating or preventing congestive heart failure and ventricular dilatation in a mammal comprising administering an effective amount of a matrix metalloproteinase inhibitor.

2. A method according to claim 1 utilizing a compound of the formula

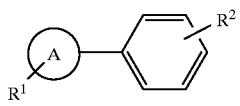

wherein:

A is phenyl or

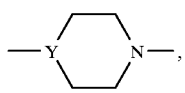

where Y is CH or N;

$R^1$ is alkyl, aryl, halo, amino, substituted or disubstituted amino, or alkoxy;

$R^2$ is carboxyalkyl ketone or oxime, carboxyalkylsulfonamide or

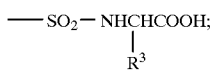

and $R^3$ is alkyl, substituted alkyl, amino, substituted or disubstituted amino, or aryl, and pharmaceutically acceptable salts thereof.

3. A method of claim 2 utilizing a compound of the formula

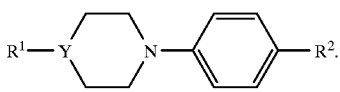

4. A method according to claim 2 employing a compound of the formula

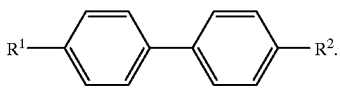

5. A method according to claim 4 employing a compound of the formula

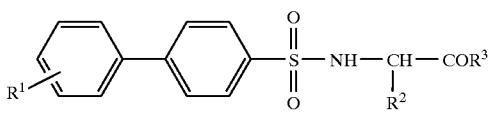

wherein:

$R^1$ is $C_1$–$C_6$ alkyl, halo, nitro, $NR^4R^5$, cyano, $OR^4$, and $COOR^4$;

$R^2$ is $C_1$–$C_6$ alkyl, optionally substituted by phenyl, substituted phenyl, $NR^4R^5$, $OR^6$, carboxy, carboxamido,

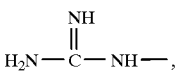

thio, methylthio, indole, imidazole, phthalimido, phenyl, and substituted phenyl;

$R^3$ is OH, $OC_1$–$C_6$ alkyl, or NHOH;

$R^4$ is hydrogen, $C_1$–$C_6$ alkyl, or $C_1$–$C_6$ alkanoyl;

$R^5$ is hydrogen or $C_1$–$C_6$ alkyl; and $R^6$ is hydrogen, $C_1$–$C_6$ alkyl, $C_1$–$C_6$ alkanoyl, phenyl, or substituted phenyl.

6. A method according to claim 5 employing a compound of the formula

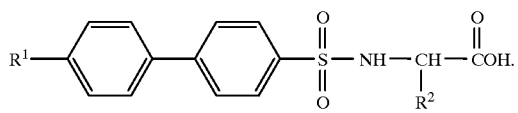

7. A method according to claim 6 employing 2-(4'-bromobiphenyl-4-sulfonylamino)-3-methyl-butyric acid.

8. A method according to claim 2 employing a compound of the formula

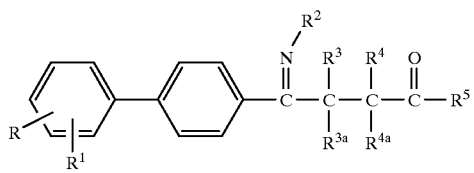

wherein R and $R^1$ are the same or different and are hydrogen, alkyl, halogen, nitro, cyano, trifluoromethyl, —$OR^6$ wherein $R^6$ is hydrogen, alkyl, aryl, arylalkyl, heteroaryl, or cycloalkyl,

wherein $R^6$ and $R^{6a}$ are the same or different and are as defined above for $R^6$,

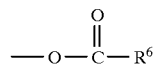

wherein $R^6$ is as defined above,

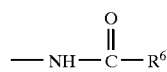

wherein $R^6$ is as defined above,

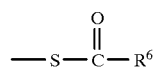

wherein $R^6$ is as defined above,

—$SR^6$ wherein $R^6$ is as defined above,

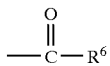

wherein $R^6$ is as defined above,

—$CH_2$—$OR^6$ wherein $R^6$ is as defined above,

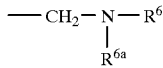

wherein $R^6$ and $R^{6a}$ are the same or different and are as defined above for $R^6$,

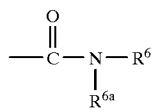

wherein $R^6$ and $R^{6a}$ are the same or different and are as defined above for $R^6$,

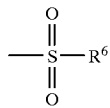

wherein $R^6$ is as defined above, cycloalkyl, or heteroaryl, with the proviso that R and $R^1$ are not both hydrogen;

$R^2$ is —$OR^6$ wherein $R^6$ is as defined above, or

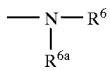

wherein $R^6$ and $R^{6a}$ are the same or different and are as defined above for $R^6$;

$R^3$, $R^{3a}$, $R^4$, and $R^{4a}$ are the same or different and are hydrogen, fluorine, alkyl, —$(CH_2)_n$-aryl wherein n is an integer from 1 to 6, —$(CH_2)_n$-heteroaryl wherein n is as defined above, —$(CH_2)_n$-cycloalkyl wherein n is as defined above, —$(CH_2)_p$-X-$(CH_2)_q$-aryl wherein X is O, S, SO, $SO_2$, or NH, and p and q are each zero or an integer of 1 to 6, and the sum of p+q is not greater than six, —$(CH_2)_p$-X-$(CH_2)_q$-heteroaryl wherein X, p, and q are as defined above, or —$(CH_2)_n$—$R^7$ wherein $R^7$ is N-phthalimido, N-2,3-naphthyimido, —$OR^6$ wherein $R^6$ is as defined above,

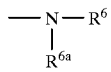

wherein $R^6$ and $R^{6a}$ are the same or different and are as defined above for $R^6$, —$SR^6$ where $R^6$ is as defined above,

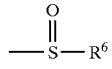

wherein $R^6$ is as defined above,

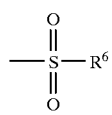

wherein $R^6$ is as defined above,

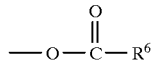

wherein $R^6$ is as defined above,

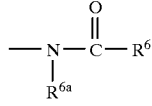

wherein $R^6$ and $R^{6a}$ are the same or different and are as defined above for $R^6$,

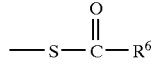

wherein $R^6$ is as defined above,

wherein $R^6$ is as defined above,

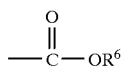

wherein $R^6$ is as defined above,

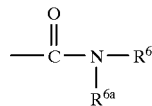

wherein $R^6$ and $R^{6a}$ are the same or different and are as defined above for $R^6$, and n is as defined above;

$R^5$ is OH or SH; with the proviso that $R^3$, $R^{3a}$, $R^4$, and $R^{4a}$ are hydrogen or at least one of $R^3$, $R^{3a}$, $R^4$, or $R^{4a}$ is fluorine; and corresponding isomers thereof; or a pharmaceutically acceptable salt thereof.

9. A method according to claim 8 employing a compound of the formula

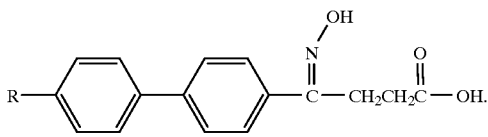

10. A method according to claim 9 employing 4-(4'-chlorobiphenyl-4-yl)-4-hydroxyimino-butyric acid.

11. A method according to claim 1 employing a compound of the formula

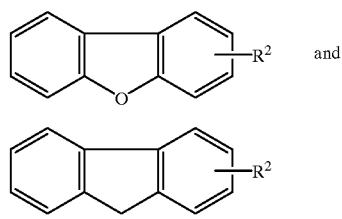

wherein
$R^2$ is

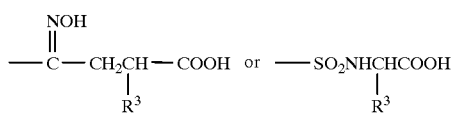

and
$R^3$ is alkyl, halo, alkoxy, acyl, or aryl.

12. A method according to claim 11 employing a compound of the formula

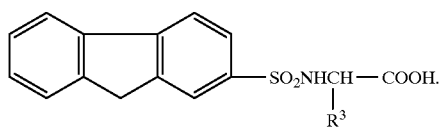

13. A method according to claim 12 employing (S)-2-(9H-fluorene-2-sulfonylamino)-4-phenyl-butyric acid.

14. A method of treating and preventing ventricular dilatation in a mammal comprising administering an effective amount of a matrix metalloproteinase inhibitor.

15. A method according to claim 14 employing a compound of the formula

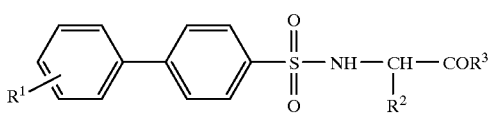

wherein:

$R^1$ is $C_1$–$C_6$ alkyl, halo, nitro, $NR^4R^5$, cyano, $OR^4$, and $COOR^4$;

$R^2$ is $C_1$–$C_6$ alkyl, optionally substituted by phenyl, substituted phenyl, $NR^4R^5$, $OR^6$, carboxy, carboxamido,

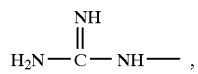

thio, methylthio, indole, imidazole, phthalimido, phenyl, and substituted phenyl;

$R^3$ is OH, $OC_1$–$C_6$ alkyl, or NHOH;

$R^4$ is hydrogen, $C_1$–$C_6$ alkyl, or $C_1$–$C_6$ alkanoyl;

$R^5$ is hydrogen or $C_1$–$C_6$ alkyl; and $R^6$ is hydrogen, $C_1$–$C_6$ alkyl, $C_1$–$C_6$ alkanoyl, phenyl, or substituted phenyl.

16. A method according to claim 15 employing 2-(4'-bromobiphenyl-4-sulfonylamino)-3-methyl-butyric acid.

17. A method according to claim 14 employing a compound of the formula

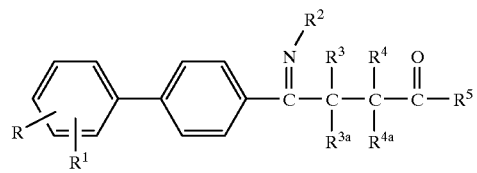

wherein R and $R^1$ are the same or different and are hydrogen,
alkyl,
halogen,
nitro,
cyano,
trifluoromethyl,
—$OR^6$ wherein $R^6$ is hydrogen,
  alkyl,
  aryl,
  arylalkyl,
  heteroaryl, or
  cycloalkyl,

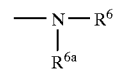

wherein $R^6$ and $R^{6a}$ are the same or different and are as defined above for $R^6$,

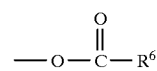

wherein $R^6$ is as defined above,

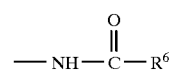

wherein $R^6$ is as defined above,

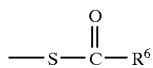

wherein $R^6$ is as defined above,
—$SR^6$ wherein $R^6$ is as defined above,

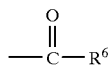

wherein $R^6$ is as defined above,
—$CH_2$—$OR^6$ wherein $R^6$ is as defined above,

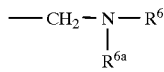

wherein $R^6$ and $R^{6a}$ are the same or different and are as defined above for $R^6$,

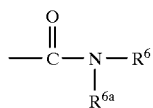

wherein $R^6$ and $R^{6a}$ are the same or different and are as defined above for $R^6$,

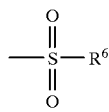

wherein $R^6$ is as defined above,
cycloalkyl, or
heteroaryl, with the proviso that R and $R^1$ are not both hydrogen;
$R^2$ is —$OR^6$ wherein $R^6$ is as defined above, or

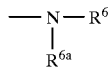

wherein $R^6$ and $R^{6a}$ are the same or different and are as defined above for $R^6$;
$R^3$, $R^{3a}$, $R^4$, and $R^{4a}$ are the same or different and are hydrogen,
fluorine,
alkyl,
—$(CH_2)_n$-aryl wherein n is an integer from 1 to 6,
—$(CH_2)_n$-heteroaryl wherein n is as defined above,
—$(CH_2)_n$-cycloalkyl wherein n is as defined above,
—$(CH_2)_p$-X-$(CH_2)_q$-aryl wherein X is O, S, SO, $SO_2$, or NH, and p and q are each zero or an integer of 1 to 6, and the sum of p+q is not greater than six, —$(CH_2)_p$-X-$(CH_2)_q$-heteroaryl wherein X, p, and q are as defined above, or —$(CH_2)_n$—$R^7$ wherein $R^7$ is N-phthalimido, N-2,3-naphthyimido, —$OR^6$ wherein $R^6$ is as defined above,

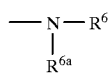

wherein $R^6$ and $R^{6a}$ are the same or different and are as defined above for $R^6$, —$SR^6$ where $R^6$ is as defined above,

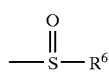

wherein $R^6$ is as defined above,

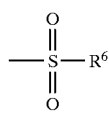

wherein $R^6$ is as defined above,

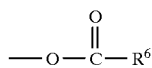

wherein $R^6$ is as defined above,

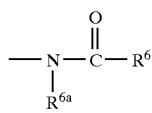

wherein $R^6$ and $R^{6a}$ are the same or different and are as defined above for $R^6$,

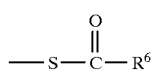

wherein $R^6$ is as defined above,

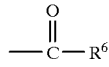

wherein $R^6$ is as defined above,

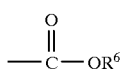

wherein $R^6$ is as defined above, or

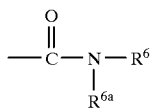

wherein $R^6$ and $R^{6a}$ are the same or different and are as defined above for $R^6$, and n is as defined above;

$R^5$ is OH or SH; with the proviso that $R^3$, $R^{3a}$, $R^4$, and $R^{4a}$ are hydrogen or at least one of $R^3$, $R^{3a}$, $R^4$, or $R^{4a}$ is fluorine; and corresponding isomers thereof; or a pharmaceutically acceptable salt thereof.

18. A method according to claim 17 employing 4-(4'-chlorobiphenyl-4-yl)-4-hydroxyimino-butyric acid.

19. A method according to claim 1 employing a compound of the formula

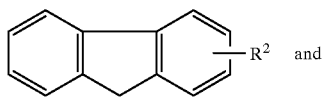 and

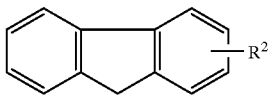

wherein $R^2$ is 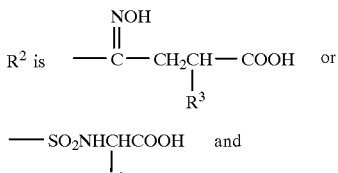 or

—SO$_2$NHCHCOOH    and
    |
    $R^3$ $R^3$ is alkyl, halo, alkoxy, acyl, or aryl.

20. A method according to claim 19 employing (S)-2-(9H-fluorene-2-sulfonylamino)-4-phenyl-butyric acid.

21. A method for treating or preventing congestive heart failure and ventricular dilatation in a mammal comprising administering an effective amount of a compound selected from batimastat, marimastat, galardin, RO 31-9790, CDP-845, CGS 27023A, or U24522.

* * * * *